(12) United States Patent
Babaoglu et al.

(10) Patent No.: US 9,108,953 B2
(45) Date of Patent: Aug. 18, 2015

(54) QUINOLINE DERIVATIVES AS BROMODOMAIN INHIBITORS

(71) Applicant: Gilead Sciences, Inc., Foster City, CA (US)

(72) Inventors: Kerim Babaoglu, Lansdale, PA (US); Britton K. Corkey, Redwood City, CA (US); Robert H. Jiang, Cupertino, CA (US); David Sperandio, Palo Alto, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/549,848

(22) Filed: Nov. 21, 2014

(65) Prior Publication Data

US 2015/0148344 A1 May 28, 2015

Related U.S. Application Data

(60) Provisional application No. 61/909,157, filed on Nov. 26, 2013.

(51) Int. Cl.
*C07D 413/04* (2006.01)
*C07D 413/14* (2006.01)
*C07D 451/04* (2006.01)

(52) U.S. Cl.
CPC ............ *C07D 413/04* (2013.01); *C07D 413/14* (2013.01); *C07D 451/04* (2013.01)

(58) Field of Classification Search
None
See application file for complete search history.

(56) References Cited

U.S. PATENT DOCUMENTS

| 6,162,804 | A | 12/2000 | Bilodeau et al. |
|---|---|---|---|
| 2007/0275984 | A1 | 11/2007 | Imogai et al. |
| 2009/0176776 | A1 | 7/2009 | Schmitz et al. |
| 2010/0204265 | A1 | 8/2010 | Baskaran et al. |
| 2012/0121540 | A1 | 5/2012 | Schmitz et al. |
| 2012/0208814 | A1* | 8/2012 | Demont et al. ............ 514/235.2 |
| 2012/0232074 | A1 | 9/2012 | Bouillot et al. |
| 2014/0187533 | A1 | 7/2014 | Pajouhesh et al. |

FOREIGN PATENT DOCUMENTS

WO  WO-2004/098494 A2  11/2004

OTHER PUBLICATIONS

Bamborogh, P. et al. (2012) "Fragment-Based Discovery of Bromodomain Inhibitors Part 2: Optimization of Phenylisoxazole Sulfonamides", J. Med. Chem., 55: 587-596.
Chung, C. et al. (2012) "Fragment-Based Discovery of Bromodomain Inhibitors Part 1: inhibitor Binding Modes and Implications for Lead Discovery", J. Med. Chem., 55: 576-586.
Hewings, D.S. et al. (2011) "3,5-Dimethylisoxazoles Act as Acetyl-Lysine-Mimetic Bromodomain Ligands" J. Med. Chem., 54: 6761-6770.
Mirguet, O. et al. (2013) "Discovery of Epigenetic Regulator I-BET762: Lead Optimization to Afford a Clinical Candidate Inhibitor of the BET Bromodomains", J. Med. Chem., 56: 7501-7515.

* cited by examiner

*Primary Examiner* — Timothy R Rozof

(57) ABSTRACT

This application relates to chemical compounds which may act as inhibitors of, or which may otherwise modulate the activity of, a bromodomain-containing protein, including bromodomain-containing protein 4 (BRD4), and to compositions and formulations containing such compounds, and methods of using and making such compounds. Compounds include compounds of Formula I

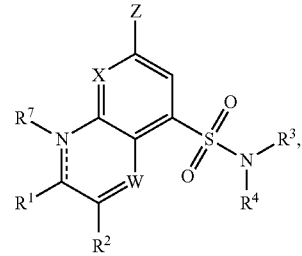

Formula I wherein $R^1$, $R^2$, $R^3$, $R^4$, $R^7$, W, X, and Z are as described herein.

18 Claims, No Drawings

QUINOLINE DERIVATIVES AS BROMODOMAIN INHIBITORS

This application claims the benefits of U.S. Provisional Application 61/909,157, filed on Nov. 26, 2013, the entire disclosure of which is incorporated herein by reference.

FIELD

This application relates to chemical compounds which may act as inhibitors of, or which may otherwise modulate the activity of, a bromodomain-containing protein, including bromodomain-containing protein 4 (BRD4), and to compositions and formulations containing such compounds, and methods of using and making such compounds.

BACKGROUND

The bromodomain and extraterminal (BET) family of proteins (BET proteins) are readers of the epigenetic code that couple acetylation of lysine residues on histones to changes in chromatin structure and gene expression. The BET family includes BRD2, BRD3, BRD4, and BRDT, all of which are widely expressed across diverse tissues, with the exception of the BRDT, whose expression is restricted to the testes. See Wu, S. Y. & Chiang, C. M., J. Biol. Chem., 282: 13141-13145 (2007). Each BET family member contains tandem bromodomains in the N-terminal regions that specifically bind acetyated lysine residues in histones H3 and H4. Id. Once bound to histones, BET proteins recruit protein complexes that modulate gene transcription either directly, such as transcriptional activators or repressors, or indirectly such as chromatin remodeling complexes. BRD4 is the most well studied member of the BET family and is known to preferentially recognize tetra-acetyated histone H4 epigenetic marks. See Filippakopoulos, P., et al., Cell, 149: 214-231 (2012). BRD4 recruits the p-TEFb complex to nucleosomes, which in turn phosphorylates the C-terminal tail of RNA polymerase II and increases the transcriptional elongation of neighboring genes. See Yang, Z., et al., Mol. Cell. Biol., 28: 967-976 (2008); Urano, E., et al., FEBS Lett., 582: 4053-4058 (2008).

The epigenetic code, including histone acetylation, is highly perturbed in many pathological disease states, resulting in the aberrant expression of genes that control cell fate, cell differentiation, cell survival, and inflammatory processes. See, e.g., Cohen, I., et al., Genes Cancer, 2: 631-647 (2011); Brooks, W. H., et al., J. Autoimmun., 34: J207-219 (2010); Wierda, R. J., et al., J. Cell Mol. Med., 14: 1225-1240 (2010); Shirodkar, A. V. & Marsden, P. A., Curr. Opin. Cardiol., 26: 209-215 (2011); Villeneuve, L. M., et al., Clin. Exp. Pharmacol. Physiol., 38: 401-409 (2011). BET proteins including BRD4 have been identified as important mediators of altered gene expression profiles found in numerous diseases including cancer, diabetes, obesity, atherosclerosis, cardiovascular and renal disorders, and viral infection. See Muller, S., et al., Expert Rev. Mol. Med., 13: e29 (2011); Zhou, M., et al., J. Viral.; 83: 1036-1044 (2009); Chung, C. W., et al., J. Med. Chem., 54: 3827-3838 (2011). Inhibitors and modulators of BET proteins, including BRD4, are therefore needed.

SUMMARY

Compounds and pharmaceutically acceptable salts thereof which may inhibit bromodomain-containing protein 4 (BRD4) are described herein. Compositions, including pharmaceutical compositions, and kits that include the compounds are also provided, as are methods of using and making the compounds. The compounds provided herein may find use in treating diseases, disorders, or conditions that are mediated by BRD4.

One aspect provides for a compound of Formula I

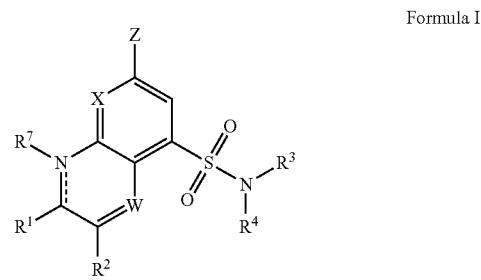

Formula I wherein:
R$^1$ is selected from the group consisting of hydrogen, halo, C$_{1-4}$ haloalkyl, unsubstituted or substituted C$_{1-4}$ alkyl, unsubstituted or substituted C$_{3-8}$ cycloalkyl, unsubstituted or substituted C$_{3-8}$ heterocycloalkyl, NR$^{1a}$R$^{1b}$, OR$^{1c}$, and oxo;
  wherein each R$^{1a}$ and R$^{1b}$ is independently selected from the group consisting of hydrogen, unsubstituted or substituted C$_{1-4}$ alkyl, unsubstituted or substituted C$_{3-8}$ cycloalkyl, and unsubstituted or substituted C$_{3-8}$ heterocycloalkyl;
  or R$^{1a}$ and R$^{1b}$ and the nitrogen atom to which they are attached join to form unsubstituted or substituted C$_{3-12}$ heterocycloalkyl, wherein the unsubstituted or substituted C$_{3-12}$ heterocycloalkyl has 1 to 3 heteroatoms selected from the group consisting of O, N, and S;
  wherein R$^{1c}$ is unsubstituted or substituted C$_{1-4}$ alkyl;
R$^2$ is selected from the group consisting of hydrogen, halo, C$_{1-4}$ haloalkyl, cyano, NR$^{2a}$R$^{2b}$, carboxyl, C(O)NR$^{2a}$R$^{2b}$, OR$^{2c}$, unsubstituted or substituted C$_{1-6}$ alkyl, unsubstituted or substituted C$_{3-12}$ cycloalkyl, unsubstituted or substituted C$_{3-12}$ heterocycloalkyl, unsubstituted or substituted C$_{3-12}$ aryl, and unsubstituted or substituted C$_{3-12}$ heteroaryl;
  wherein each R$^{2a}$, R$^{2b}$ and R$^{2c}$ is independently selected from the group consisting of hydrogen, C$_{1-4}$ haloalkyl, unsubstituted or substituted C$_{1-6}$ alkyl, unsubstituted or substituted C$_{3-12}$ cycloalkyl, and unsubstituted or substituted C$_{3-12}$ heterocycloalkyl;
  or R$^{2a}$ and R$^{2b}$ and the nitrogen atom to which they are attached join to form unsubstituted or substituted C$_{3-12}$ heterocycloalkyl or unsubstituted or substituted C$_{3-12}$ heteroaryl; wherein the unsubstituted or substituted C$_{3-12}$ heterocycloalkyl or the unsubstituted or substituted C$_{3-12}$ heteroaryl has 1 to 3 heteroatoms selected from the group consisting of O, N, and S;
W is N or CR$^w$;
  wherein R$^w$ is independently selected from the group consisting of hydrogen, C$_{1-4}$ haloalkyl, unsubstituted or substituted C$_{1-4}$ alkyl, and unsubstituted or substituted C$_{1-4}$ alkoxy;
X is N or CR$^X$;
  wherein Rx is independently selected from the group consisting of hydrogen, halogen, C$_{1-4}$ haloalkyl, unsubstituted or substituted C$_{1-4}$ alkyl, and unsubstituted or substituted C$_{1-4}$ alkoxy;

$R^3$ is selected from the group consisting of hydrogen, and unsubstituted or substituted $C_{1-4}$ alkyl;

$R^4$ is selected from the group consisting of hydrogen, $C_{1-8}$ haloalkyl, unsubstituted or substituted $C_{1-8}$ alkyl, unsubstituted or substituted $C_{3-8}$ cycloalkyl, unsubstituted or substituted $C_{3-12}$ heterocycloalkyl, and unsubstituted or substituted $C_{3-12}$ heteroaryl;

or $R^3$ and $R^4$ and the nitrogen atom to which they are attached join to form unsubstituted or substituted $C_{3-42}$ heterocycloalkyl or unsubstituted or substituted $C_{3-12}$ heteroaryl;

wherein the unsubstituted or substituted $C_{3-12}$ heterocycloalkyl or the unsubstituted or substituted $C_{3-12}$ heteroaryl has 1 to 3 heteroatoms selected from the group consisting of O, N, and S;

$R^7$ is hydrogen or absent; and

Z is selected from the group consisting of unsubstituted or substituted isoxazolyl, and unsubstituted or substituted pyrazolyl, or a pharmaceutically acceptable salt thereof.

In certain aspects the compound is a compound of Formula IA:

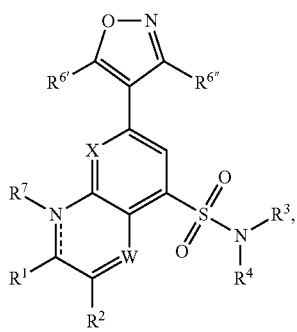

Formula IA wherein $R^1$, $R^2$, W, X, $R^3$, $R^4$, and $R^7$ are as defined in Formula I; and each $R^{6'}$ and $R^{6''}$ is independently selected from the group consisting of unsubstituted $C_{1-4}$ alkyl, $CH_2OR^{6a}$, and $CH_2NR^{6b}R^{6c}$;

wherein each $R^{6a}$, $R^{6b}$, and $R^{6c}$ is independently selected from the group consisting of hydrogen, $C_{1-4}$ haloalkyl, unsubstituted $C_{1-4}$ alkyl, and acetyl, or a pharmaceutically acceptable salt thereof.

In certain aspects the compound is a compound of Formula IB:

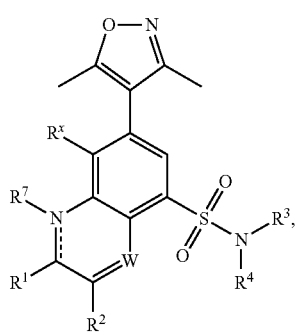

Formula IB wherein:

$R^1$, $R^2$, W, X, $R^3$, $R^4$, and $R^7$ are as defined in Formula I; and $R^x$ is selected from the group consisting of hydrogen, halo, and unsubstituted $C_{1-4}$ alkyl, or a pharmaceutically acceptable salt thereof.

In certain aspects the compound is a compound of Formula IC:

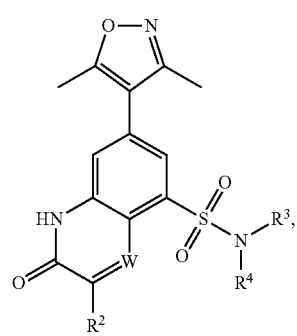

Formula IC wherein:

$R^2$ and W are as defined in Formula I;

$R^3$ is hydrogen; and $R^4$ is selected from the group consisting of unsubstituted or substituted $C_{1-4}$ alkyl, $C_{1-8}$ haloalkyl, and unsubstituted or substituted $C_{3-8}$ cycloalkyl, or a pharmaceutically acceptable salt thereof.

In certain aspects the compound is a compound of Formula ID:

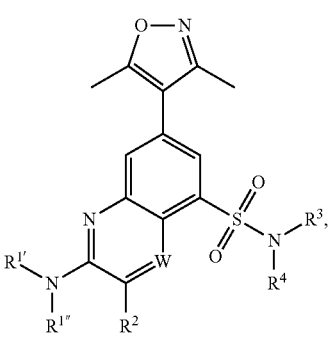

Formula ID wherein $R^2$, W, $R^3$ and $R^4$ are as defined in Formula I; and each $R^{1'}$ and $R^{1''}$ is independently selected from the group consisting of hydrogen, unsubstituted or substituted $C_{1-4}$ alkyl, unsubstituted or substituted $C_{3-8}$ cycloalkyl, and unsubstituted or substituted $C_{3-8}$ heterocycloalkyl;

or $R^{1'}$ and $R^{1''}$ and the nitrogen atom to which they are attached join to form unsubstituted or substituted $C_{3-12}$ heterocycloalkyl; wherein the unsubstituted or substituted $C_{3-12}$ heterocycloalkyl has 1 to 3 heteroatoms selected from O, N, and S, or a pharmaceutically acceptable salt thereof.

In certain aspects the compound is a compound of Formula I':

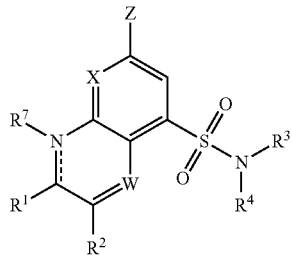

wherein:
R¹ is selected from the group consisting of hydrogen, halo, $C_{1-4}$ haloalkyl, $C_{1-4}$ alkyl, $C_{3-8}$ cycloalkyl, $C_{3-8}$ heterocycloalkyl, $NR^{1a}R^{1b}$, $OR^{1c}$, and oxo;
  wherein each $R^{1a}$ and $R^{1b}$ is independently selected from the group consisting of hydrogen, $C_{1-4}$ alkyl, $C_{3-8}$ cycloalkyl, and $C_{3-8}$ heterocycloalkyl;
  or $R^{1a}$ and $R^{1b}$ and the nitrogen atom to which they are attached join to form $C_{3-12}$ heterocycloalkyl, wherein the $C_{3-12}$ heterocycloalkyl has 1 to 3 heteroatoms selected from the group consisting of oxygen, nitrogen and sulfur;
  wherein $R^{1c}$ is $C_{1-4}$ alkyl;
R² is selected from the group consisting of hydrogen, halo, $C_{1-4}$ haloalkyl, cyano, $NR^{2a}R^{2b}$, carboxyl, $C(O)NR^{2a}R^{2b}$, $OR^{2c}$, $C_{1-6}$ alkyl, $C_{3-12}$ cycloalkyl, $C_{3-12}$ heterocycloalkyl, $C_{3-12}$ aryl, and $C_{3-12}$ heteroaryl;
  wherein each $R^{2a}$, $R^{2b}$ and $R^{2c}$ is independently selected from the group consisting of hydrogen, $C_{1-4}$ haloalkyl, $C_{1-6}$ alkyl, $C_{3-12}$ cycloalkyl, and $C_{3-12}$ heterocycloalkyl;
  or $R^{2a}$ and $R^{2b}$ and the nitrogen atom to which they are attached join to form $C_{3-12}$ heterocycloalkyl or $C_{3-12}$ heteroaryl, wherein each $C_{3-12}$ heterocycloalkyl and $C_{3-12}$ heteroaryl independently has 1 to 3 heteroatoms selected from the group consisting of oxygen, nitrogen and sulfur;
W is N or $CR^w$;
  wherein $R^w$ is independently selected from the group consisting of hydrogen, $C_{1-4}$ haloalkyl, $C_{1-4}$ alkyl, and $C_{1-4}$ alkoxy;
X is N or $CR^x$;
  wherein $R^x$ is independently selected from the group consisting of hydrogen, $C_{1-4}$ haloalkyl, $C_{1-4}$ alkyl, and $C_{1-4}$ alkoxy;
R³ is selected from the group consisting of hydrogen and $C_{1-4}$ alkyl;
R⁴ is selected from the group consisting of hydrogen, $C_{1-8}$ haloalkyl, $C_{1-8}$ alkyl, $C_{3-8}$ cycloalkyl, $C_{3-12}$ heterocycloalkyl, and $C_{3-12}$ heteroaryl;
or R³ and R⁴ and the nitrogen atom to which they are attached join to form $C_{3-12}$ heterocycloalkyl or $C_{3-12}$ heteroaryl, wherein each $C_{3-12}$ heterocycloalkyl and $C_{3-12}$ heteroaryl independently has 1 to 3 heteroatoms selected from the group consisting of oxygen, nitrogen and sulfur;
R⁷ is hydrogen or absent; and
Z is isoxazolyl or pyrazolyl, wherein each isoxazolyl and pyrazolyl is independently unsubstituted or substituted with 1 or 2 substituents selected from the group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ hydroxyalkoxy, —$CH_2$—$C_3$-$C_6$ cycloalkyl, —$C(O)NH_2$, —$C(O)NH$—$C_1$-$C_6$ alkyl, and —$C(O)N(C_1$-$C_6$ alkyl$)_2$;

wherein each $C_{1-4}$ alkyl, $C_{1-6}$ alkyl, $C_{1-8}$ alkyl, and $C_{1-4}$ alkoxy is independently unsubstituted or substituted with 1 to 5 substituents selected from the group consisting of $C_2$-$C_6$-alkenyl, $C_2$-$C_6$-alkynyl, $C_1$-$C_6$-alkoxy, $C_3$-$C_{10}$-cycloalkyl, $C_4$-$C_{10}$-cycloalkenyl, acyl, amino, azido, cyano, halogen, $C_1$-$C_4$-haloalkyl, hydroxy, oxo, carboxy, thiol, $C_6$-$C_{10}$-aryl, $C_6$-$C_{10}$-aryloxy, 5- to 10-membered heteroaryl, 5- to 10-membered heteroaryloxy, 4- to 10-membered heterocycloalkyl, 4- to 10-membered heterocycloalkoxy, nitro, —SO-alkyl, —SO-cycloalkyl, —SO-(4- to 10-membered heterocycloalkyl), —SO—($C_6$-$C_{10}$-aryl), —SO-(5- to 10-membered heteroaryl), —$SO_2$—($C_1$-$C_6$-alkyl), —$SO_2$—($C_3$-$C_{10}$-cycloalkyl), —$SO_2$-(4- to 10-membered heterocycloalkyl), —$SO_2$—($C_6$-$C_{10}$-aryl), and —$SO_2$-(5- to 8-membered heteroaryl); and
wherein each $C_{3-8}$ cycloalkyl, $C_{3-12}$ cycloalkyl, $C_{3-8}$ heterocycloalkyl, $C_{3-12}$ heterocycloalkyl, $C_{3-12}$ aryl, and $C_{3-12}$ heteroaryl is independently unsubstituted or substituted with 1 to 5 substituents independently selected from the group consisting of $C_1$-$C_6$-alkyl, $C_2$-$C_6$-alkenyl, $C_2$-$C_6$-alkynyl, $C_1$-$C_6$-alkoxy, $C_3$-$C_8$-cycloalkyl, $C_4$-$C_8$-cycloalkenyl, acyl, acylamino, acyloxy, amino, aminocarbonyl, $C_1$-$C_6$-alkoxycarbonylamino, azido, cyano, halogen, $C_1$-$C_4$-haloalkyl, hydroxy, oxo, thiocarbonyl, carboxy, $C_1$-$C_6$-carboxyalkyl, $C_6$-$C_{10}$-arylthio, heteroarylthio, heterocyclylthio, thiol, $C_6$-$C_{10}$-aryl, $C_6$-$C_{10}$-aryloxy, 5- to 10-membered heteroaryl, aminosulfonyl, aminocarbonyl amino, 5- to 10-membered heteroaryloxy, 3- to 8-membered heterocycloalkyl, 3- to 8-membered heterocycloalkoxy, hydroxyamino, alkoxyamino, nitro, —SO—($C_1$-$C_6$-alkyl), —SO—($C_6$-$C_{10}$-aryl), —SO-(5- to 10-membered heteroaryl), —$SO_2$—($C_1$-$C_6$-alkyl), —$SO_2$—($C_6$-$C_{10}$-aryl), and —$SO_2$-(5- to 10-membered heteroaryl); and
or a pharmaceutically acceptable salt thereof.

In certain aspects the compound is a compound of Formula IE or IF:

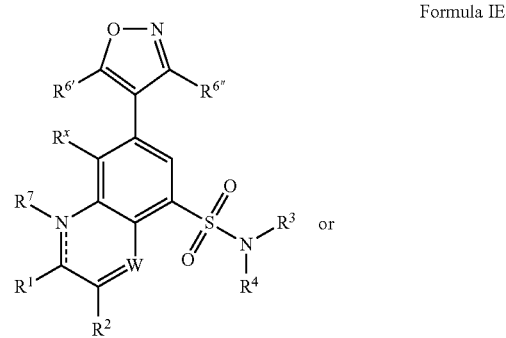

Formula IE

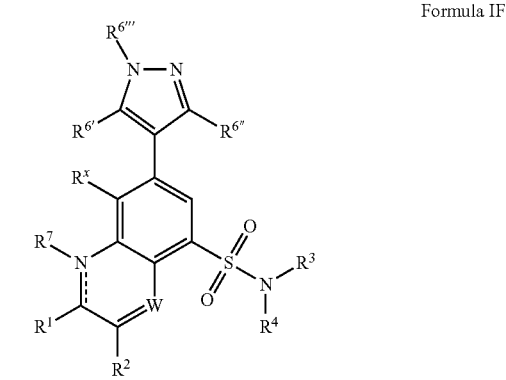

Formula IF wherein:
W is CR$^W$ or N;
R$^w$ is selected from the group consisting of hydrogen, C$_{1-4}$ haloalkyl, C$_{1-4}$ alkyl, and C$_{1-4}$ alkoxy, wherein the C$_{1-4}$ alkyl and C$_{1-4}$ alkoxy are independently unsubstituted or substituted with 1 to 4 substituents independently selected from the group consisting of halogen, —OH, =O, CN, NH$_2$, C$_2$-C$_6$ alkenyl, C$_2$-C$_6$ alkynyl, C$_1$-C$_3$ haloalkyl, and C$_{1-4}$ alkoxy;

R$^x$ is selected from the group consisting of hydrogen, halogen, C$_{1-4}$ haloalkyl, C$_{1-4}$ alkyl, and C$_{1-4}$ alkoxy, wherein the C$_{1-4}$ alkyl and C$_{1-4}$ alkoxy are independently unsubstituted or substituted with 1 to 4 substituents independently selected from the group consisting of halogen, —OH, =O, CN, NH$_2$, C$_2$-C$_6$ alkenyl, C$_2$-C$_6$ alkynyl, C$_1$-C$_3$ haloalkyl, and C$_{1-4}$ alkoxy;

R$^1$ is selected from the group consisting of hydrogen, =O, C$_1$-C$_3$ haloalkyl, halogen, C$_3$-C$_6$-cycloalkyl, NR$^{1a}$R$^{1b}$, OR$^{1c}$,

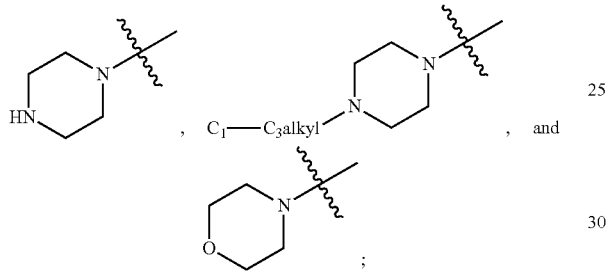

wherein each R$^{1a}$, R$^{1b}$, and R$^{1c}$ is independently selected from the group consisting of hydrogen, unsubstituted C$_{1-4}$ alkyl, or C$_{1-4}$ alkyl substituted with C$_3$-C$_8$ cycloalkyl;

R$^2$ is selected from the group consisting of hydrogen, halogen, CN, C$_3$-C$_8$ cycloalkyl, C$_1$-C$_6$ hydroxyalkyl, NR$^{2a}$R$^{2b}$, carboxyl, C(O)NR$^{2a}$R$^{2b}$, OR$^{2c}$, 4- to 8-membered heterocycloalkyl having 1 or 2 ring heteroatoms selected from the group consisting of oxygen and nitrogen, and 5- or 6-membered heteroaryl having 1 or 2 ring nitrogen atoms, wherein each C$_3$-C$_8$ cycloalkyl, 4- to 8-membered heterocycloalkyl, and 5- or 6-membered heteroaryl is independently unsubstituted or substituted with 1 to 3 substituents selected from the group consisting of OH, halogen, C$_1$-C$_6$ alkoxy, C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

wherein each R$^{2a}$, R$^{2b}$, and R$^{2c}$ is independently hydrogen or C$_1$-C$_6$ alkyl, wherein the C$_1$-C$_6$ alkyl is unsubstituted or substituted with 1 to 3 substituents selected from the group consisting of OH, halogen, C$_1$-C$_6$ alkoxy, C$_1$-C$_4$ haloalkyl, C$_3$-C$_6$ cycloalkyl, —O—C$_3$-C$_6$ cycloalkyl, —NH$_2$, —NH(C$_1$-C$_6$ alkyl), —N(C$_1$-C$_6$ alkyl)$_2$, —NH—(C$_1$-C$_4$ haloalkyl), —N(C$_1$-C$_4$ haloalkyl)$_2$, 4- to 8-membered heterocycloalkyl having 1 or 2 ring heteroatoms selected from the group consisting of oxygen or nitrogen, and 5- or 6-membered heteroaryl having 1 or 2 ring nitrogen atoms, wherein the 4- to 8-membered heterocycle and 5- or 6-membered heteroaryl is unsubstituted or substituted with 1 to 3 substituents selected from the group consisting of OH, =O, halogen, C$_1$-C$_6$ alkyl, C$_1$-C$_6$ alkoxy, C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

R$^3$ is hydrogen or C$_1$-C$_3$ alkyl;

R$^4$ is:

a) hydrogen, b) C$_1$-C$_8$ alkyl, wherein the C$_1$-C$_8$ alkyl is unsubstituted or substituted with 1 to 3 substituents selected from the group consisting of =O, OH, CN, halogen, C$_1$-C$_6$ alkoxy, C$_1$-C$_4$ haloalkyl, C$_3$-C$_6$ cycloalkyl, —O—(C$_3$-C$_6$ cycloalkyl), —NH$_2$, —NH(C$_1$-C$_6$ alkyl), —N(C$_1$-C$_6$ alkyl)$_2$, —NH—(C$_1$-C$_4$ haloalkyl), —N(C$_1$-C$_4$ haloalkyl)$_2$, phenyl, 4- to 8-membered heterocycloalkyl having 1 or 2 ring heteroatoms selected from the group consisting of oxygen, sulfur, and nitrogen, and 5- or 6-membered heteroaryl having 1 or 2 ring heteroatoms selected from the group consisting of oxygen, sulfur and nitrogen, wherein each C$_3$-C$_6$ cycloalkyl, —O—(C$_3$-C$_6$ cycloalkyl), phenyl, 4- to 8-membered heterocyclic, and 5- or 6-membered heteroaryl is independently unsubstituted or substituted with 1 to 3 substituents selected from the group consisting of OH, =O, CN, halogen, C$_1$-C$_6$ alkyl, C$_1$-C$_6$ alkoxy, —(C$_1$-C$_6$ alkyl)-O—(C$_1$-C$_6$ alkyl), C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

c) C$_3$-C$_7$ cycloalkyl, wherein the C$_3$-C$_7$ cycloalkyl is unsubstituted or substituted with 1 to 3 substituents selected from the group consisting of:

i) OH, =O, CN, halogen, C$_1$-C$_6$ alkyl, C$_1$-C$_6$ alkoxy, —(C$_1$-C$_6$ alkyl)-O—(C$_1$-C$_6$ alkyl), C$_1$-C$_4$ haloalkyl, —O—C$_1$-C$_4$ haloalkyl, NH$_2$, and —NH(C$_1$-C$_6$ alkyl), —N(C$_1$-C$_6$ alkyl)$_2$, —NHC(O)OH, —NHCO$_2$—C$_1$-C$_6$ alkyl, —O-benzyl, ii) —CO$_2$H, —C(O)NH(C$_1$-C$_6$ alkyl), —C(O)N(C$_1$-C$_6$ alkyl)$_2$, wherein C$_1$-C$_6$ alkyl is unsubstituted or substituted with 1 to 3 substituents selected from the group consisting of OH, halogen, —NH$_2$, —NH(C$_1$-C$_6$ alkyl), and —N(C$_1$-C$_6$ alkyl)$_2$;

iii) —C(O)NH—C$_3$-C$_6$ cycloalkyl, —C(O)N(C$_1$-C$_3$ alkyl)-C$_3$-C$_6$ cycloalkyl,

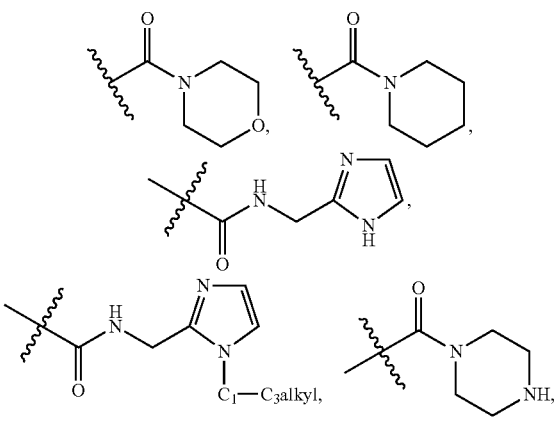

-continued

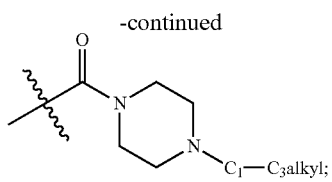

iv) phenyl, wherein the phenyl is unsubstituted or substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH;

d) 5- to 7-membered heterocycloalkyl or heteroaryl having 1 or 2 ring atoms selected from the group consisting of nitrogen and oxygen, wherein each heterocycloalkyl and heteroaryl is independently unsubstituted or substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH;

or $R^3$ and $R^4$ and the nitrogen to which they are bound are joined to form a 4- to 6-membered heterocycloalkyl having 1 or 2 ring nitrogen atoms, wherein 4- to 6-membered heterocycloalkyl is unsubstituted or substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH;

$R^{6'}$ is hydrogen, $C_1$-$C_6$ alkyl, —$CH_2OH$, or $C_3$-$C_6$ cycloalkyl;

$R^{6''}$ hydrogen, $C_1$-$C_6$ alkyl, or $C_3$-$C_6$ cycloalkyl;

$R^{6'''}$ is hydrogen, $C_1$-$C_6$ alkyl, or $C_3$-$C_6$ cycloalkyl; and $R^7$ is hydrogen or absent;

or a pharmaceutically acceptable salt thereof.

In some embodiments, the compound is selected from Compound Nos. 1-100, or a pharmaceutically acceptable salt thereof.

Also provided is a pharmaceutical composition comprising: at least one compound of Formula I, IA, IB, IC, ID, I', IE or IF, or a pharmaceutically acceptable salt thereof, and at least one pharmaceutically acceptable vehicle. Examples of pharmaceutically acceptable vehicles may be selected from carriers, adjuvants, and excipients.

Also provided is a method of treating a subject, who has or is suspected of having a disease or condition responsive or believed to be responsive to the inhibition of a bromodomain, comprising administering a therapeutically effective amount of a compound of Formula I, IA, IB, IC, ID, I', IE or IF, or a pharmaceutically acceptable salt thereof. In some embodiments, the bromodomain is bromodomain-containing protein 4 (BRD4). In some embodiments, the subject is a human.

Another aspect provides for a method of treating a subject having a disease or condition responsive to the inhibition of a bromodomain-containing protein, comprising administering a therapeutically effective amount of a compound of Formula (I), or a pharmaceutically acceptable salt thereof. In some aspects, the bromodomain-containing protein is BRD4. In some aspects, the disease or condition is an autoimmune disease, an inflammatory disease, a neurodegenerative disease, a cancer, a cardiovascular disorder, a renal disorder, a viral infection, or obesity. In certain embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors. In some aspects the disease or condition is a solid tumor of the colon, rectum, prostate, lung, pancreas, liver, kidney, cervix, stomach, ovaries, breast, skin, brain, meninges, or central nervous system (including a neuroblastoma or a glioblastoma). In some aspects, the disease or condition is a lymphoma. In some aspects, the disease or condition is a B-cell lymphoma. In some aspects, the disease or condition is Burkitt's lymphoma. In some aspects, the disease or condition is diffuse large B-cell lymphoma. In some aspects, the disease or condition is multiple myeloma. In some aspects the disease or condition is a carcinoma. In some aspects the disease or condition is NUT midline cardinoma.

In some aspects the subject is a human. In some aspects, the compound is administered intravenously, intramuscularly, parenterally, nasally, or orally. In one embodiment, the compound is administered orally.

Also provided is a method of inhibiting a bromodomain, comprising contacting the bromodomain with a compound of Formula I, IA, IB, IC, ID, I', IE or IF, or a pharmaceutically acceptable salt thereof.

Also provided is the use of a compound of Formula I, IA, IB, IC, ID, I', IE or IF, or a pharmaceutically acceptable salt thereof, in the manufacture of a medicament for the treatment of a disease or condition responsive to bromodomain inhibition.

Also provided are kits that include a compound of Formula I, IA, IB, IC, ID, I', IE or IF, or a pharmaceutically acceptable salt thereof. In one embodiment, the kit further includes instructions for use. In one aspect, a kit includes a compound of Formula I, IA, IB, IC, ID, I', IE or IF, or a pharmaceutically acceptable salt thereof, and instructions for use of the compounds in the treatment of the diseases or conditions described above.

Also provided are articles of manufacture that include a compound of Formula I, IA, IB, IC, ID, I', IE or IF, or a pharmaceutically acceptable salt thereof. In one embodiment, the container may be a vial, jar, ampoule, preloaded syringe, or an intravenous bag.

DETAILED DESCRIPTION

The following description sets forth exemplary methods and parameters. It should be recognized, however, that such description is not intended as a limitation on the scope of the present disclosure but is instead provided as a description of exemplary embodiments.

As used herein, when any variable occurs more than one time in a chemical formula, its definition on each occurrence is independent of its definition at every other occurrence. In accordance with the usual meaning of "a" and "the" in patents, reference, for example, to "a" protein or "the" protein is inclusive of one or more proteins.

As used in the present specification, the following words and phrases are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom.

A dashed line indicates an optional bond.

The term "alkyl" refers to a monoradical branched or unbranched saturated hydrocarbon chain. In some embodiments, alkyl groups may have 1 to 20 carbon atoms (a $C_{1-20}$ alkyl or a $C_1$-$C_{20}$ alkyl), or 1 to 8 carbon atoms (a $C_{1-8}$ alkyl or a $C_1$-$C_8$ alkyl), or 1 to 4 carbon atoms (a $C_{1-4}$ alkyl or a $C_1$-$C_4$ alkyl). When an alkyl residue having a specific number of carbons is named, all geometric isomers having that number of carbons are intended to be encompassed and described; thus, for example, "butyl" is meant to include n-butyl, see-butyl, iso-butyl, and tert-butyl; "propyl" includes n-propyl and iso-propyl. Examples of alkyl include methyl, ethyl, n-propyl, iso-propyl, n-butyl, iso-butyl, t-butyl, n-hexyl, n-decyl, and tetradecyl.

The term "substituted alkyl" refers to an alkyl group having one or more substituents. In some embodiments, alkyl groups may have 1 to 5 substituents, or 1 to 4 substituents, or 1 to 3 substituents, or 1 or 2 substituents, or 1 substituent. Suitable substituents of the alkyl group may include, for example, alkenyl (e.g., $C_2$-$C_6$ alkenyl), alkynyl (e.g., $C_2$-$C_6$ alkynyl), alkoxy (e.g., $C_1$-$C_6$ alkoxy), cycloalkyl (e.g., $C_3$-$C_8$ cycloalkyl), cycloalkenyl (e.g., $C_3$-$C_8$ cycloalkenyl), acyl, amino, azido, cyano, halogen, haloalkyl (e.g., $C_1$-$C_4$ haloalkyl), hydroxy, oxo, carboxy, thiol, aryl, aryloxy, heteroaryl, heteroaryloxy, heterocycloalkyl, heterocycloalkoxy, nitro, —SO-alkyl, —SO-cycloalkyl, —SO-heterocycloalkyl, —SO-aryl, —SO-heteroaryl, —$SO_2$-alkyl, —$SO_2$-cycloalkyl, —$SO_2$-heterocycloalkyl, —$SO_2$-aryl and —$SO_2$-heteroaryl. In certain embodiments, the substituents of an alkyl group may be further substituted with 1 to 3 substituents, 1 or 2 substituents, or 1 substituent, and such further substituents may include, for example, alkyl (e.g., $C_1$-$C_6$ alkyl), cycloalkyl (e.g., $C_3$-$C_8$ cycloalkyl), heterocycloalkyl (e.g., $C_3$-$C_8$ heterocycloalkyl), aryl (e.g., $C_6$-$C_{10}$ aryl), heteroaryl (e.g., 8- to 10-membered heteroaryl), halogen, haloalkyl (e.g., $C_1$-$C_4$ haloalkyl), hydroxyl, amino, oxo, alkoxy (e.g., $C_1$-$C_6$ alkoxy), and carboxy. For example, an alkyl group may be substituted with an alkoxy group, and such alkoxy group may be further substituted with a hydroxyl group

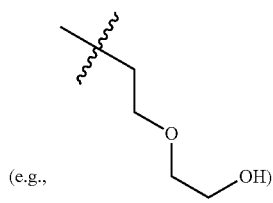

(e.g., )

or an amino group

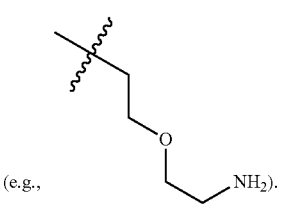

(e.g., ).

"Cycloalkyl" refers to a saturated hydrocarbon ring group, having the specified number of carbon atoms. In some embodiments, cycloalkyl has from 3 to 20 ring carbon atoms (i.e., $C_{3-20}$ cycloalkyl), or 3 to 12 ring carbon atoms (i.e., $C_{3-12}$ cycloalkyl), or 3 to 8 ring carbon atoms (i.e., $C_{3-8}$ cycloalkyl). The cycloalkyl may be monocyclic or bicyclic. Some examples of cycloalkyl groups include cyclopropyl, cyclobutyl, cyclopentyl, and cyclohexyl. In certain embodiments, cycloalkyl may also include bridged and caged saturated ring groups, such as norbornane and bicyclo[3.1.0]hexane. In other embodiments, cycloalkyl may also include spirocycles, including for example, Spiro[2.4]heptane.

"Heterocycloalkyl" refers to a saturated hydrocarbon ring group, having the specified number of ring atoms, with one or more heteroatoms independently selected from nitrogen, oxygen and sulfur. In some embodiments, heterocycloalkyl has from 3 to 20 ring atoms (i.e., $C_{3-20}$ heterocycloalkyl), or 3 to 12 ring atoms (i.e., $C_{3-12}$ heterocycloalkyl), or 3 to 8 ring atoms (i.e., $C_{3-8}$ heterocycloalkyl). In other embodiments, heterocycloalkyl has 1 to 5 heteroatoms, 1 to 4 heteroatoms, 1 to 3 heteroatoms, 1 or 2 heteroatoms, or 1 heteroatom selected form nitrogen, sulfur or oxygen in at least one ring. In certain embodiments, the heteroatom is selected from nitrogen or oxygen. Examples of heterocycloalkyl groups may include pyrrolidinyl, piperidinyl, piperazinyl, oxetanyl, dioxolanyl, azetidinyl, and morpholinyl. In certain embodiments, heterocycloalkyl may also include bridged and caged saturated ring groups such as azabicyclo[3.2.1]octanyl. In other embodiments, heterocycloalkyl may also include spirocycles.

"Alkenyl" refers to an unsaturated hydrocarbon group having at least one site of olefinic unsaturation (i.e., having at least one moiety of the formula C=C). In some embodiments, alkenyl has from 2 to 8 carbon atoms ($C_2$-$C_8$ alkenyl or $C_{2-8}$ alkenyl), 2 to 6 carbon atoms ($C_2$-$C_6$ alkenyl or $C_{2-6}$ alkenyl), or 2 to 4 carbon atoms ($C_2$-$C_4$ alkenyl or $C_{2-4}$ alkenyl), or 2 or 3 carbon atoms ($C_2$-$C_3$ alkenyl or $C_{2-3}$ alkenyl). Examples of alkenyl groups may include ethenyl (or vinyl, i.e., —CH=$CH_2$), 1-propylene (or allyl, i.e., —$CH_2$CH=$CH_2$), and isopropylene (—C($CH_3$)=$CH_2$).

"Cycloalkenyl" refers to a non-aromatic hydrocarbon ring group having at least one point of unsaturation and 4, 5, 6, or 7 ring carbon atoms. Examples of cycloalkenyl groups include cyclobutyl, cyclopentyl, cyclohexenyl, cyclohexa-1,3,-dienyl, and cycloheptenyl rings. In some embodiments, alkenyl may have from 1 to 5 substituents, or 1 to 4 substituents, or 1 to 3 substituents, or 1 or 2 substituents, or 1 substituent. Suitable substituents of the alkenyl group may include, for example, alkyl (e.g., $C_1$-$C_6$ alkyl), alkoxy (e.g., $C_1$-$C_6$ alkoxy), cycloalkyl (e.g., $C_3$-$C_8$ cycloalkyl), cycloalkenyl (e.g., $C_3$-$C_8$ cycloalkenyl), acyl, amino, azido, cyano, halogen, haloalkyl (e.g., $C_1$-$C_4$ haloalkyl), hydroxy, oxo, carboxy, thiol, aryl (e.g., $C_6$-$C_{10}$ aryl), aryloxy (e.g., $C_6$-$C_{10}$ aryloxy), heteroaryl (e.g., $C_6$-$C_{10}$ heteroaryl), heteroaryloxy (e.g., $C_6$-$C_{10}$ heteroaryloxy), heterocycloalkyl, heterocycloalkoxy, nitro, —SO-alkyl, —SO-cycloalkyl, —SO-heterocycloalkyl, —SO-aryl, —SO-heteroaryl, —$SO_2$-alkyl, —$SO_2$-cycloalkyl, —$SO_2$-heterocycloalkyl, —$SO_2$-aryl and —$SO_2$-heteroaryl. In certain embodiments, the substituents of an alkenyl group may be further substituted with 1 to 3 substituents, 1 or 2 substituents, or 1 substituent, and such further substituents may include, for example, alkyl (e.g., $C_1$-$C_6$ alkyl), cycloalkyl (e.g., $C_3$-$C_8$ cycloalkyl), heterocycloalkyl (e.g., $C_3$-$C_8$ heterocycloalkyl), aryl (e.g., $C_6$-$C_{10}$ aryl), 8- to 10-membered heteroaryl, halogen, haloalkyl (e.g., $C_1$-$C_4$ haloalkyl), hydroxyl, amino, oxo, alkoxy (e.g., $C_1$-$C_6$ alkoxy), and carboxy. For example, an alkenyl group may be substituted with an alkoxy group, and such alkoxy group may be further substituted with a hydroxyl group or an amino group.

"Alkynyl" refers to an unsaturated hydrocarbon group having at least one site of acetylenic unsaturation (i.e., having at least one moiety of the formula C≡C). In some embodiments, alkynyl has from 2 to 8 carbon atoms ($C_2$-$C_8$ alkynyl or $C_{2-8}$ alkynyl), or 2 to 6 carbon atoms ($C_2$-$C_6$ alkynyl or $C_{2-6}$ alkynyl), or 2 to 4 carbon atoms ($C_2$-$C_4$ alkynyl or $C_{2-4}$ alkynyl), or 2 or 3 carbon atoms ($C_2$-$C_3$ alkynyl or $C_{2-3}$ alkynyl). In some embodiments, alkynyl groups may have from 1 to 5 substituents, or 1 to 4 substituents, or 1 to 3 substituents, or 1 or 2 substituents, or 1 substituent. Suitable substituents of the alkynyl group may include, for example, alkyl (e.g., $C_1$-$C_6$ alkyl), alkoxy (e.g., $C_1$-$C_6$ alkoxy), cycloalkyl (e.g., $C_3$-$C_8$ cycloalkyl), cycloalkenyl (e.g., $C_3$-$C_8$ cycloalkenyl), acyl, amino, azido, cyano, halogen, haloalkyl (e.g., $C_1$-$C_4$ haloalkyl), hydroxy, oxo, carboxy, thiol, aryl (e.g., $C_6$-$C_{10}$ aryl), aryloxy, heteroaryl (e.g., $C_6$-$C_{10}$ heteroaryl), heteroaryloxy (e.g., $C_6$-$C_{10}$ heteroaryloxy), heterocycloalkyl, heterocycloalkoxy, nitro, —SO-alkyl, —SO-cycloalkyl, —SO-heterocycloalkyl, —SO-aryl, —SO-heteroaryl, —$SO_2$-alkyl, —$SO_2$-cycloalkyl, —$SO_2$-heterocycloalkyl, —$SO_2$-aryl and —$SO_2$-heteroaryl. In certain embodiments, the substituents of an alkynyl group may be further substituted with 1 to 3 substituents, 1 or 2 substituents, or 1 substituent, and such further substituents may include, for example, alkyl (e.g., $C_1$-$C_6$ alkyl), cycloalkyl (e.g., $C_3$-$C_8$ cycloalkyl), heterocycloalkyl (e.g., $C_3$-$C_8$ heterocycloalkyl), aryl (e.g., $C_6$-$C_{10}$ aryl), 8- to 10-membered heteroaryl, halogen, haloalkyl (e.g., $C_1$-$C_4$ haloalkyl), hydroxyl, amino, oxo, alkoxy (e.g., $C_1$-$C_6$ alkoxy), and carboxy. For example, an alkynyl group may be substituted with an alkoxy group, and such alkoxy group may be further substituted with hydroxyl or amino.

The terms "halogen" and "halo" refer to fluoro, bromo, chloro, and iodo.

"Haloalkyl" refers to an unbranched or branched alkyl group as defined above, wherein one or more hydrogen atoms are substituted with a halogen. Where a residue is substituted with more than one halogen, it may be referred to by using a prefix corresponding to the number of halogen moieties attached. For example, dihaloaryl, dihaloalkyl, and trihaloaryl refer to aryl and alkyl substituted with two ("di") or three ("tri") halo groups. In some embodiments, haloalkyl groups may have 1 to 20 carbons (a $C_{1-20}$ haloalkyl or a $C_1$-$C_{20}$ haloalkyl), or 1 to 8 carbons (a $C_{1-8}$ haloalkyl or a $C_1$-$C_8$ haloalkyl), 1 to 6 carbons (a $C_{1-6}$ haloalkyl or a $C_1$-$C_8$ haloalkyl), 1 to 4 carbons (a $C_{1-4}$ haloalkyl or a $C_1$-$C_4$ haloalkyl), or 1 to 3 carbons (a $C_{1-3}$ haloalkyl or a $C_1$-$C_3$ haloalkyl), in which one or more hydrogen atoms of the alkyl chain are substituted with a halogen. Examples of haloalkyl groups may include —$CH_2F$, —$CHF_2$, —$CF_3$, and —$CH_2CH_2F$. An alkyl group in which each hydrogen atom is replaced with a halo group is referred to as a "perhaloalkyl." One example of a perhaloalkyl group is trifluoromethyl (—$CF_3$). Similarly, "haloalkoxy" refers to an alkoxy group in which one or more hydrogen atoms are substituted with a halogen in the hydrocarbon making up the alkyl moiety of the alkoxy group. Haloalkoxy groups may have 1 to 20 carbons (a $C_{1-20}$ haloalkoxy or a $C_1$-$C_{20}$ haloalkoxy), or 1 to 8 carbons (a $C_{1-8}$ haloalkoxy or a $C_1$-$C_8$ haloalkoxy), 1 to 6 carbons (a $C_{1-6}$ haloalkoxy or a $C_1$-$C_8$ haloalkoxy), 1 to 4 carbons (a $C_{1-4}$ haloalkoxy or a $C_1$-$C_4$ haloalkoxy), or 1 to 3 carbons (a $C_{1-3}$ haloalkoxy or a $C_1$-$C_3$ haloalkoxy). Examples of a haloalkoxy group include difluoromethoxy (—$OCHF_2$) or trifluoromethoxy (—$OCF_3$).

"Alkoxy" refers to the group —OR, where R is alkyl attached through the oxygen bridge. Alkoxy groups include, for example, methoxy, ethoxy, propoxy, butoxy, pentoxy, and hexoxy. The term "substituted alkoxy" refers to alkoxy wherein the alkyl constituent is substituted, including for example, —O-(substituted alkyl), wherein "substituted alkyl" is as described herein.

"Aryl" refers to an aromatic carbocyclic group having a single ring, multiple rings, or multiple condensed (fused) rings. In certain embodiments, aryl has 3 to 20 ring carbon atoms (i.e., $C_{3-20}$ aryl), 3 to 12 carbon ring atoms (i.e., $C_{3-12}$ aryl), 3 to 8 carbon ring atoms (i.e., $C_{3-8}$ aryl), or 6 to 10 carbon ring atoms (i.e., $C_{6-10}$ aryl). Examples of aryl groups include phenyl, biphenyl, fluorenyl, naphthyl, and anthryl. In certain embodiments, if one or more aryl groups are fused with a heteroaryl ring, the resulting ring system is heteroaryl.

"Heteroaryl" refers to an aromatic group with a single ring, multiple rings, or multiple fused rings, with one or more heteroatoms selected from nitrogen, oxygen, and sulfur within at least one ring. In certain embodiments, heteroaryl has 3 to 20 ring atoms (i.e., $C_{3-20}$ heteroaryl), 3 to 12 ring atoms (i.e., $C_{3-12}$ heteroaryl), 3 to 8 ring atoms (i.e., $C_{3-8}$ heteroaryl), or 6 to 10 ring atoms (i.e., $C_{6-10}$ heteroaryl). In other embodiments, heteroaryl has 1 to 5 heteroatoms, 1 to 4 heteroatoms, 1 to 3 heteroatoms, 1 or 2 heteroatoms, or 1 heteroatom chosen from nitrogen, oxygen, and sulfur in at least one ring. Examples of heteroaryl groups include pyridyl, pyrazinyl, pyrimidinyl, pyrazolinyl, imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, and pyrazolyl.

The terms "substituted cycloalkyl", "substituted heterocycloalkyl", "substituted aryl" and "substituted heteroaryl" refer to a cycloalkyl group, a heterocycloalkyl group, an aryl group and a heteroaryl group, respectively, having one or more substituents. In some embodiments, cycloalkyl, heterocycloalkyl, aryl and heteroaryl may have 1 to 5 substituents, or 1 to 4 substituents, or 1 to 3 substituents, or 1 or 2 substituents, or 1 substituent. Suitable substituents of the cycloalkyl, heterocycloalkyl, aryl and heteroaryl groups may include, for example, $C_1$-$C_6$ alkyl (e.g., $C_1$-$C_6$ alkyl), alkenyl (e.g., $C_2$-$C_6$ alkenyl), alkynyl (e.g., $C_2$-$C_6$ alkynyl), alkoxy (e.g., $C_1$-$C_6$ alkoxy), cycloalkyl (e.g., $C_3$-$C_8$ cycloalkyl), cycloalkenyl (e.g., $C_3$-$C_8$ cycloalkenyl), acyl, acylamino, acyloxy, amino, aminocarbonyl, alkoxycarbonylamino, azido, cyano, halogen, haloalkyl (e.g., $C_1$-$C_4$ haloalkyl), hydroxy, oxo, thiocarbonyl, carboxy, carboxyalkyl, arylthio, heteroarylthio, heterocylylthio, thiol, aryl, aryloxy, heteroaryl, aminosulfonyl, aminocarbonyl amino, heteroaryloxy, heterocycloalkyl, heterocycloalkoxy, hydroxyamino, alkoxyamino, nitro, —SO-alkyl, —SO-aryl, —SO-heteroaryl, —$SO_2$-alkyl, —$SO_2$-aryl and —$SO_2$-heteroaryl. In certain embodiments, the substituents of a cycloalkyl, heterocycloalkyl, aryl or heteroaryl group may be further substituted with 1 to 3 substituents, 1 or 2 substituents, or 1 substituent, and such further substituents may include, for example, alkyl, cycloalkyl, heterocycloalkyl, aryl, heteroaryl, halogen, haloalkyl, hydroxyl, amino, oxo, alkoxy, and carboxy.

"Amino" refers to —$NH_2$.

"Substituted amino" refers to the group —NHR or —NRR where each R may be independently chosen from, for example, hydroxy, alkyl, cycloalkyl, acyl, aminocarbonyl, aryl, heteroaryl, heterocycloalkyl, alkoxycarbonyl, sulfinyl and sulfonyl, provided that only one R may be hydroxyl. In certain embodiments, the substituents of the amino group may be further substituted with 1 to 3 substituents, 1 or 2 substituents, or 1 substituent, and such further substituents may include, for example, halogen, haloalkyl, alkyl, cycloalkyl, heterocycloalkyl, aryl, heteroaryl, carboxy, hydroxyl, oxo, alkoxy, and amino.

"Substituted isoxazolyl" and "substituted pyrazolyl" refer, respectively, to isoxazolyl and pyrazolyl groups substituted with 1 or 2 substituents. In some embodiments, the substituents for isoxazolyl and pyrazolyl may include, for example, $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ hydroxyalkoxy, —$CH_2$—$C_3$-$C_6$ cycloalkyl, —C(O)$NH_2$, —C(O)NH—$C_1$-$C_6$ alkyl, and —C(O)N($C_1$-$C_6$ alkyl)$_2$.

"Aminocarbonyl" refers to the group —C(O)NRR where each R may independently be any of the substituents for substituted amino as described above.

"Ester" refers to the group —C(O)OR, where R may be alkyl, cycloalkyl, heterocycloalkyl, aryl, and heteroaryl. In certain embodiments, the R groups may be further substituted with 1 to 3 substituents, 1 or 2 substituents, or 1 substituent, and such further substituents may include, for example, alkyl, cycloalkyl, heterocycloalkyl, aryl, heteroaryl, alkoxy, halogen, haloalkyl, hydroxyl, oxo, and amino.

"Acyl" denotes a group —C(O)R; "acylamino" refers to group —NRC(O)R; and "acyloxy" refers to group —OC(O)R. In some embodiments, R at each instance may independently be hydrogen, alkyl, cycloalkyl, heterocycloalkyl, aryl, and heteroaryl. In certain embodiments, the R groups may be further substituted with 1 to 3 substituents, 1 or 2 substituents, or 1 substituent, and such further substituents may include, for example, alkyl, cycloalkyl, heterocycloalkyl, aryl, heteroaryl, alkoxy, halogen, haloalkyl, hydroxyl, oxo, and amino.

"Carbonyl" refers to the group —C(O), which may also be expressed as —C=O.

"Oxo" refers to the moiety =O.

"Cyano" refers to the group —CN.

"Nitro" refers to the group —$NO_2$.

"Sulfonyl" refers to —$SO_2$R where R may be chosen from alkyl, alkenyl, alkynyl, cycloalkyl, heterocycloalkyl, aryl, heteroaryl. In certain embodiments, the R groups may be further substituted with 1 to 3 substituents, 1 or 2 substituents, or 1 substituent, and such further substituents may include, for example, alkyl, cycloalkyl, heterocycloalkyl, aryl, heteroaryl, alkoxy, halogen, haloalkyl, hydroxyl, oxo, and amino.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group. A moiety lacking the term "substituted" is intended to be an unsubstituted moiety.

Ranges of the numbers in as group as defined herein are understood to specifically include all whole numbers in the given range. Examples include the number ranges provided for terms such as "substituents", "heteroatoms", "carbons", "carbon atoms", "ring atoms", "ring carbon atoms", and "carbon ring atoms". Ranges of 1 to 3 include 1, 2, or 3 members; 1 to 4 includes 1, 2, 3, or 4 members; 1 to 5 includes 1, 2, 3, 4, or 5 members; 3 to 8 includes 3, 4, 5, 6, 7, or 8 members; 3 to 12 includes 3, 4, 5, 6, 7, 8, 9, 10, 11, or 12 members; and 3 to 20 includes 3, 4, 5, 6, 7, 8, 9, 10, 11, 12, 13, 14, 15, 16, 17, 18, 19, or 20 members.

Additionally, the compounds described herein may possess one or more chiral centers, and can be produced as individual enantiomers or diastereoisomers, or as a mixture thereof. The number of stereoisomers present in any given compound of a given Formula depends upon the number of asymmetric centers present. For example, there are 2n stereoisomers possible where n is the number of asymmetric centers. The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

One aspect provides for a compound of Formula I

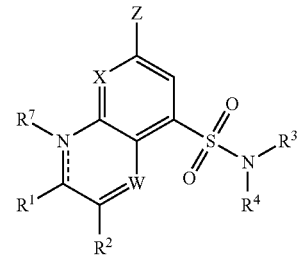

Formula I wherein:
R$^1$ is selected from the group consisting of hydrogen, halo, $C_{1-4}$ haloalkyl, unsubstituted or substituted $C_{1-4}$ alkyl, unsubstituted or substituted $C_{3-8}$ cycloalkyl, unsubstituted or substituted $C_{3-8}$ heterocycloalkyl, NR$^{1a}$R$^{1b}$, OR$^{1c}$, and oxo;
  wherein each R$^{1a}$ and R$^{1b}$ is independently selected from the group consisting of hydrogen, unsubstituted or substituted $C_{1-4}$ alkyl, unsubstituted or substituted $C_{3-8}$ cycloalkyl, and unsubstituted or substituted $C_{3-8}$ heterocycloalkyl;
  or R$^{1a}$ and R$^{1b}$ and the nitrogen atom to which they are attached join to form unsubstituted or substituted $C_{3-12}$ heterocycloalkyl, wherein the unsubstituted or substituted $C_{3-12}$ heterocycloalkyl has 1 to 3 heteroatoms selected from O, N, and S;
  wherein R$^{1c}$ is unsubstituted or substituted $C_{1-4}$ alkyl;
R$^2$ is selected from the group consisting of hydrogen, halo, $C_{1-4}$ haloalkyl, cyano, NR$^{2a}$R$^{2b}$, carboxyl, C(O)NR$^{2a}$R$^{2b}$, OR$^{2c}$, unsubstituted or substituted $C_{1-6}$ alkyl, unsubstituted or substituted $C_{3-12}$ cycloalkyl, unsubstituted or substituted $C_{3-12}$ heterocycloalkyl, unsubstituted or substituted $C_{3-12}$ aryl, and unsubstituted or substituted $C_{3-12}$ heteroaryl;
  wherein each R$^{2a}$, R$^{2b}$ and R$^{ee}$ is independently selected from the group consisting of hydrogen, $C_{1-4}$ haloalkyl, unsubstituted or substituted $C_{1-6}$ alkyl, unsubstituted or substituted $C_{3-12}$ cycloalkyl, and unsubstituted or substituted $C_{3-12}$ heterocycloalkyl;
  or R$^{2a}$ and R$^{2b}$ and the nitrogen atom to which they are attached join to form unsubstituted or substituted $C_{3-12}$ heterocycloalkyl or unsubstituted or substituted $C_{3-12}$ heteroaryl; wherein the unsubstituted or substituted $C_{3-12}$ heterocycloalkyl or the unsubstituted or substituted $C_{3-12}$ heteroaryl has 1 to 3 heteroatoms selected from O, N, and S;
W is N or CR$^w$;

wherein $R^w$ is independently selected from the group consisting of hydrogen, $C_{1-4}$ haloalkyl, unsubstituted or substituted $C_{1-4}$ alkyl, and unsubstituted or substituted $C_{1-4}$ alkoxy;

X is N or $CR^x$;
  wherein $R^x$ is independently selected from the group consisting of hydrogen, halogen, $C_{1-4}$ haloalkyl, unsubstituted or substituted $C_{1-4}$ alkyl, and unsubstituted or substituted $C_{1-4}$ alkoxy;

$R^3$ is selected from the group consisting of hydrogen, and unsubstituted or substituted $C_{1-4}$ alkyl;

$R^4$ is selected from the group consisting of hydrogen, $C_{1-8}$ haloalkyl, unsubstituted or substituted $C_{1-8}$ alkyl, unsubstituted or substituted $C_{3-8}$ cycloalkyl, unsubstituted or substituted $C_{3-12}$ heterocycloalkyl, and unsubstituted or substituted $C_{3-12}$ heteroaryl;

or $R^3$ and $R^4$ and the nitrogen atom to which they are attached join to form unsubstituted or substituted $C_{3-12}$ heterocycloalkyl or unsubstituted or substituted $C_{3-12}$ heteroaryl;
  wherein the unsubstituted or substituted $C_{3-12}$ heterocycloalkyl or the unsubstituted or substituted $C_{3-12}$ heteroaryl has 1 to 3 heteroatoms selected from O, N, and S;

$R^7$ is hydrogen or absent; and

Z is selected from the group consisting of unsubstituted or substituted isoxazolyl, and unsubstituted or substituted pyrazolyl, or a pharmaceutically acceptable salt thereof.

In some embodiments of Formula I, $R^1$ is selected from the group consisting of:
hydrogen;
halo;
$C_{1-4}$ haloalkyl;
unsubstituted $C_{1-4}$ alkyl;
substituted $C_{1-4}$ alkyl with 1 to 3 substituents independently selected from the group consisting of halo and unsubstituted $C_{3-6}$ cycloalkyl;
unsubstituted $C_{3-8}$ cycloalkyl;
substituted $C_{3-8}$ cycloalkyl with 1 to 3 substituents independently selected from the group consisting of halo and unsubstituted $C_{1-4}$ alkyl;
unsubstituted $C_{3-8}$ heterocycloalkyl;
substituted $C_{3-8}$ heterocycloalkyl with 1 to 3 substituents independently selected from the group consisting of halo and unsubstituted $C_{1-4}$ alkyl;
$NR^{1a}R^{1b}$;
$OR^{1c}$; and
oxo.

In some embodiments of Formula I, $R^1$ is selected from the group consisting of
hydrogen;
halo;
$C_{1-4}$ haloalkyl;
unsubstituted $C_{1-4}$ alkyl;
$NR^{1a}R^{1b}$;
$OR^{1c}$; and
oxo.

In certain embodiments of Formula I, each $R^{1a}$ and $R^{1b}$ is independently selected from the group consisting of
hydrogen;
unsubstituted $C_{1-4}$ alkyl;
substituted $C_{1-4}$ alkyl with 1 to 3 substituents independently selected from the group consisting of halo and unsubstituted $C_{3-6}$ cycloalkyl;
unsubstituted $C_{3-8}$ cycloalkyl;

substituted $C_{3-8}$ cycloalkyl with 1 to 3 substituents independently selected from the group consisting of halo and unsubstituted $C_{1-4}$ alkyl;
unsubstituted $C_{3-8}$ heterocycloalkyl; and
substituted $C_{3-8}$ heterocycloalkyl with 1 to 3 substituents independently selected from the group consisting of halo and unsubstituted $C_{1-4}$ alkyl.

In other embodiments of Formula I, $R^{1a}$ and $R^{1b}$ and the nitrogen atom to which they are attached join to form $C_{3-12}$ heterocycloalkyl;
  wherein the $C_{3-12}$ heterocycloalkyl has 1 to 3 heteroatoms selected from O and N; and
  wherein the $C_{3-12}$ heterocycloalkyl is unsubstituted, or substituted with 1 to 3 unsubstituted $C_{1-4}$ alkyl substituents.

In certain embodiments of Formula I, $R^{1c}$ is:
unsubstituted $C_{1-4}$ alkyl; or
substituted $C_{1-4}$ alkyl with an unsubstituted $C_{3-6}$ cycloalkyl substituent.

In some embodiments of Formula I, $R^1$ is selected from the group consisting of: hydrogen, oxo, $CHF_2$, chloro, methoxy, unsubstituted amino,

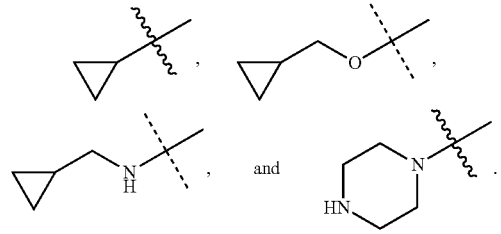

In one embodiment of Formula I, $R^1$ is hydrogen or oxo.

In some embodiments of Formula I, $R^2$ is selected from the group consisting of:
hydrogen;
halo;
$C_{1-4}$ haloalkyl,
cyano;
$NR^{2a}R^{2b}$;
carboxyl;
$C(O)NR^{2a}R^{2b}$;
$OR^{2c}$;
unsubstituted $C_{1-6}$ alkyl;
substituted $C_{1-6}$ alkyl with 1 to 3 substituents independently selected from the group consisting of unsubstituted or substituted $C_{3-12}$ cycloalkyl, and unsubstituted or substituted $C_{3-12}$ heterocycloalkyl;
unsubstituted $C_{3-12}$ cycloalkyl;
substituted $C_{3-12}$ cycloalkyl with 1 to 3 substituents independently selected from the group consisting of halo and unsubstituted $C_{1-4}$ alkyl;
unsubstituted $C_{3-12}$ heterocycloalkyl;
substituted $C_{3-12}$ heterocycloalkyl with 1 to 3 substituents independently selected from the group consisting of halo, unsubstituted $C_{1-4}$ alkyl, and unsubstituted $C_{3-6}$ cycloalkyl;
unsubstituted $C_{3-12}$ aryl;
substituted $C_{3-12}$ aryl with 1 to 3 substituents independently selected from the group consisting of halo, unsubstituted $C_{1-4}$ alkyl, and unsubstituted $C_{3-6}$ cycloalkyl;
unsubstituted $C_{3-12}$ heteroaryl; and
substituted $C_{3-12}$ heteroaryl with 1 to 3 substituents independently selected from the group consisting of halo, unsubstituted $C_{1-4}$ alkyl, and unsubstituted $C_{3-6}$ cycloalkyl.

In one embodiment of Formula I, $R^2$ is hydrogen.

In certain embodiments of Formula I, each $R^{2a}$, $R^{2b}$ and $R^{2c}$ is independently selected from the group consisting of:

hydrogen;

$C_{1-4}$ haloalkyl;

unsubstituted $C_{1-6}$ alkyl;

substituted $C_{1-6}$ alkyl with 1 to 3 substituents independently selected from the group consisting of hydroxyl, unsubstituted or substituted amino, unsubstituted or substituted $C_{1-4}$ alkoxy, unsubstituted $C_{3-12}$ cycloalkyl, unsubstituted $C_{3-12}$ heterocycloalkyl, unsubstituted $C_{3-12}$ aryl, and unsubstituted $C_{3-12}$ heteroaryl;

unsubstituted $C_{3-12}$ cycloalkyl;

substituted $C_{3-12}$ cycloalkyl with 1 to 3 unsubstituted $C_{1-4}$ alkyl substituents;

unsubstituted $C_{3-12}$ heterocycloalkyl; and substituted $C_{3-12}$ heterocycloalkyl with 1 to 3 unsubstituted $C_{1-4}$ alkyl substituents.

In other embodiments of Formula I, $R^{2a}$ and $R^{2b}$ and the nitrogen atom to which they are attached join to form $C_{3-12}$ heterocycloalkyl or $C_{3-12}$ heteroaryl;

wherein the $C_{3-12}$ heterocycloalkyl or the $C_{3-12}$ heteroaryl has 1 to 3 heteroatoms selected from O and N; and wherein the $C_{3-12}$ heterocycloalkyl or the $C_{3-12}$ heteroaryl is unsubstituted, or substituted with 1 to 3 substituents independently from unsubstituted $C_{1-4}$ alkyl and oxo.

In some embodiments of Formula I, $R^2$ is selected from the group consisting of: hydrogen, bromo, cyano, unsubstituted amino,

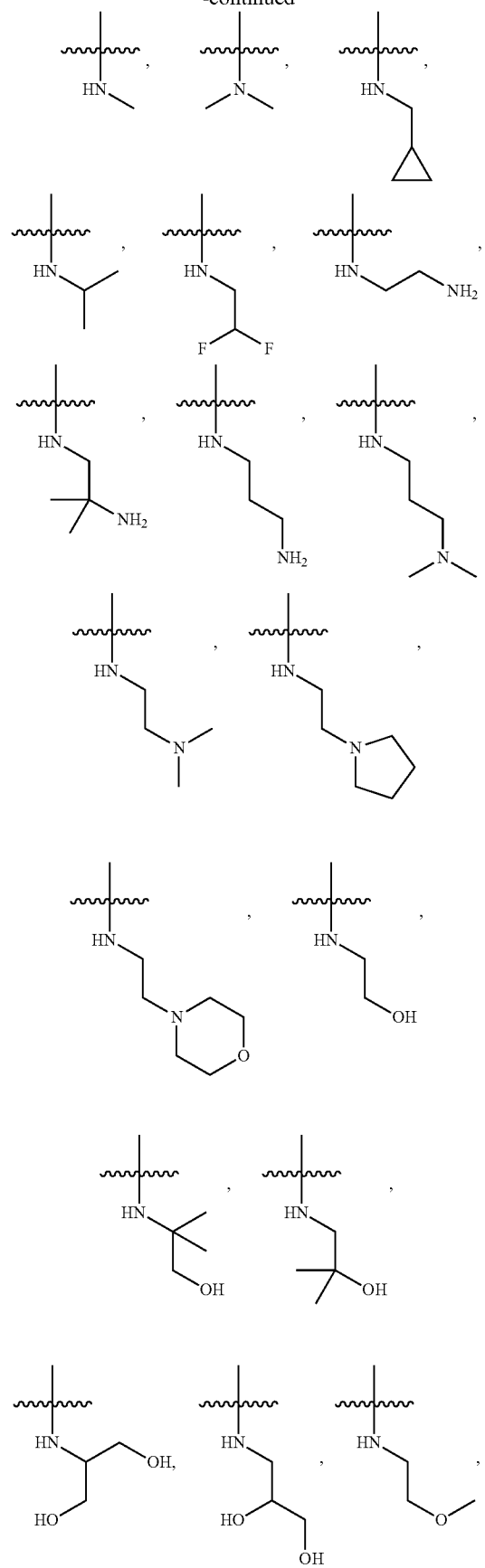

-continued

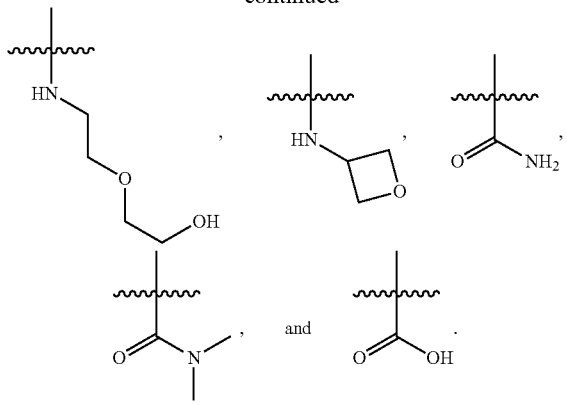

In some embodiments of Formula I, $R^3$ is hydrogen or methyl.

In some embodiments of Formula I, $R^4$ is selected from the group consisting of unsubstituted or substituted $C_{3-8}$ cycloalkyl, and unsubstituted or substituted $C_{3-12}$ heterocycloalkyl.

In certain embodiments of Formula I, $R^4$ is selected from the group consisting of:
hydrogen;
$C_{1-8}$ haloalkyl;
unsubstituted $C_{1-8}$ alkyl;
substituted $C_{1-8}$ alkyl with 1 to 3 substituents independently selected from the group consisting of halo, unsubstituted amino, hydroxyl, carboxyl, $C(O)NR^{4a}R^{4b}$, $NHC(O)R^{4c}$, $NHC(O)OR^{4c}$, unsubstituted or substituted $C_{3-6}$ cycloalkyl, and unsubstituted or substituted. $C_{3-12}$ aryl;
unsubstituted $C_{3-8}$ cycloalkyl;
substituted $C_{3-8}$ cycloalkyl with 1 to 3 substituents independently selected from the group consisting of halo, $C_{1-4}$ haloalkyl, cyano, unsubstituted or substituted $C_{1-4}$ alkyl, unsubstituted or substituted $C_{3-12}$ aryl, $C(O)NR^{4a}R^{4b}$, $NR^{4a}R^{4b}$, $NHC(O)R^{4c}$, $NHC(O)OR^{4c}$, and $OR^{4c}$;
unsubstituted $C_{3-12}$ heterocycloalkyl;
substituted $C_{3-12}$ heterocycloalkyl with 1 to 3 substituents independently selected from the group consisting of halo, $C_{1-4}$ haloalkyl, cyano, unsubstituted or substituted $C_{1-4}$ alkyl, unsubstituted or substituted $C_{3-6}$ cycloalkyl, unsubstituted or substituted $C_{3-12}$ aryl, $C(O)NR^{4a}R^{4b}$, $NR^{4a}R^{4b}$, $NHC(O)R^{4c}$, $NHC(O)OR^{4c}$, and $OR^{4c}$;
unsubstituted $C_{3-12}$ heteroaryl; and
substituted $C_{3-12}$ heteroaryl with 1 to 3 substituents independently selected from the group consisting of halo, $C_{1-4}$ haloalkyl, cyano, unsubstituted or substituted $C_{1-4}$ alkyl, unsubstituted or substituted. $C_{3-6}$ cycloalkyl, unsubstituted or substituted $C_{3-12}$ aryl, $C(O)NR^{4a}R^{4b}$, $NR^{4a}R^{4b}$, $NHC(O)R^{4c}$, $NHC(O)OR^{4c}$, and $OR^{4c}$;
wherein each $R^{4a}$, $R^{4b}$ and $R^{4c}$ is independently selected from the group consisting of hydrogen, unsubstituted or substituted $C_{1-4}$ alkyl, unsubstituted or substituted $C_{3-6}$ cycloalkyl, and unsubstituted or substituted $C_{3-6}$ heterocycloalkyl;
or $R^{4a}$ and $R^{4b}$ can be taken together with the nitrogen to which they are attached to form a heterocycloalkyl containing 1 or 2 heteroatoms selected from N or O.

In other embodiments of Formula I, $R^4$ is selected from the group consisting of unsubstituted or substituted cyclopropyl, unsubstituted or substituted cyclobutyl, unsubstituted or substituted cyclopentyl, unsubstituted or substituted cyclohexyl, unsubstituted or substituted pyrrolidinyl, unsubstituted or substituted bicycloheptanyl, and unsubstituted or substituted azabicyclooctanyl.

In some embodiments of Formula I,

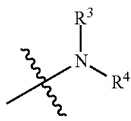

is selected from the group consisting of:

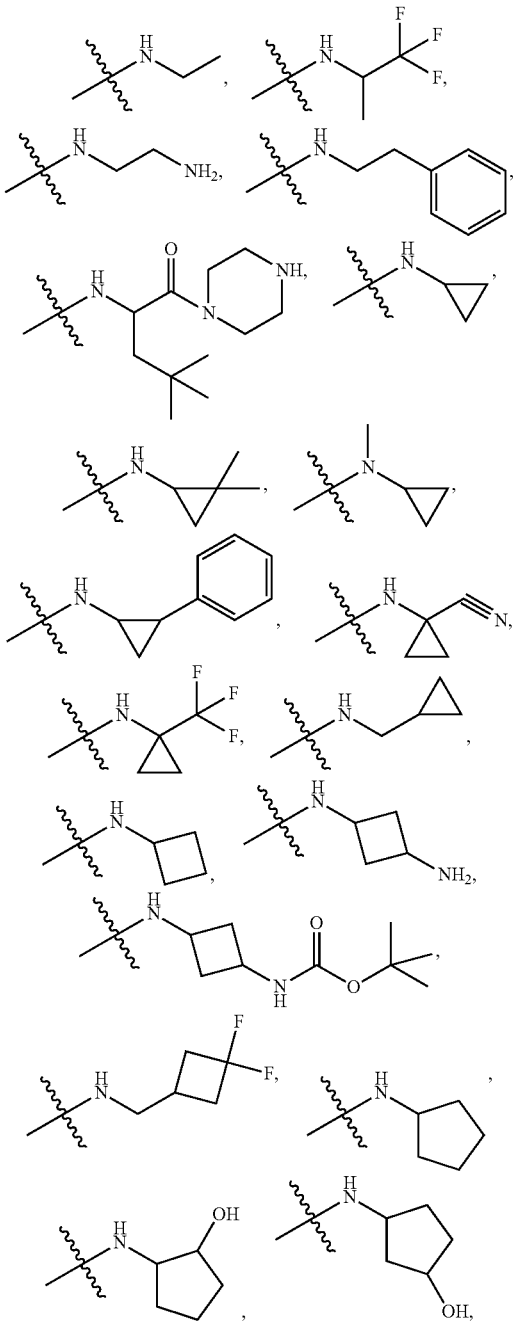

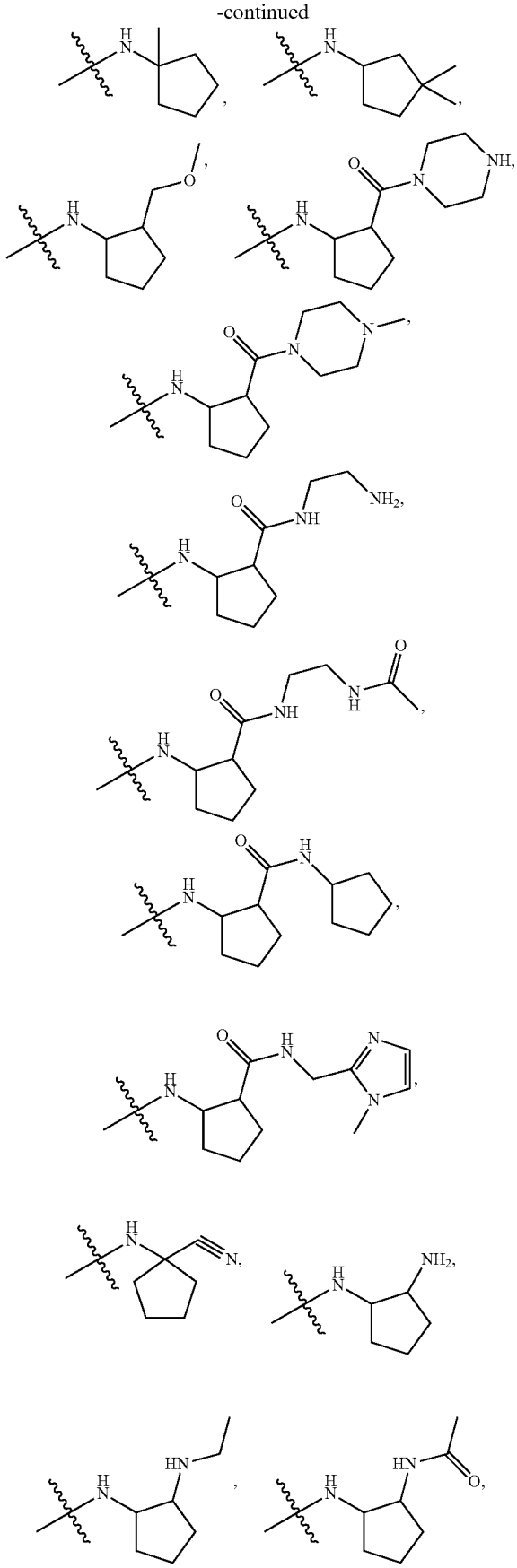

In other embodiments of Formula I, $R^3$ and $R^4$ and the nitrogen atom to which they are attached join to form $C_{3-12}$ heterocycloalkyl or $C_{3-12}$ heteroaryl;

wherein the $C_{3-12}$ heterocycloalkyl or the $C_{3-12}$ heteroaryl has 1 to 3 heteroatoms selected from O and N; and wherein the $C_{3-12}$ heterocycloalkyl or the $C_{3-12}$ heteroaryl is unsubstituted, or substituted with 1 to 3 substituents independently from halo, unsubstituted $C_{1-4}$ alkyl, and oxo.

In one embodiment of Formula I, W is $CR^w$, wherein $R^w$ is hydrogen.

In another embodiment of Formula I, X is $CR^X$. In certain embodiments, $R^x$ is hydrogen or chloro.

In some embodiments of Formula I, Z is selected from the group consisting of:

unsubstituted isoxazolyl;

isoxazolyl substituted with 1 or 2 unsubstituted $C_{1-4}$ alkyl substituents;

unsubstituted pyrazolyl; and pyrazolyl substituted with 1 or 2 unsubstituted $C_{1-4}$ alkyl substituents.

$R^7$ is hydrogen or absent. In compounds of Formula I wherein the dashed line is a bond, $R^7$ is absent. For example, in compounds wherein $R^1$ is not oxo (that is, $R^1$ is a group described for compounds of Formula I above, except for oxo), the dashed line is a bond and $R^7$ is absent. In compounds of Formula I wherein the dashed line is not a bond, $R^7$ is hydrogen. For example, in compounds wherein $R^1$ is oxo, the dashed line is not a bond and $R^7$ is hydrogen.

Provided is also a compound of Formula IA:

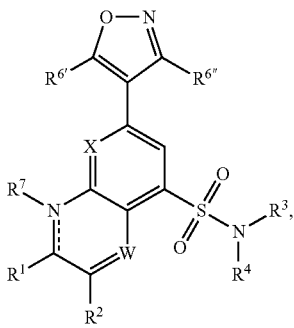

Formula IA wherein:
R$^1$, R$^2$, W, X, R$^3$, R$^4$, and R$^7$ are as defined in Formula I; and
each R$^{6'}$ and R$^{6''}$ is independently selected from the group consisting of unsubstituted C$_{1-4}$ alkyl, CH$_2$OR$^{6a}$, and CH$_2$NR$^{6b}$R$^{6c}$;
wherein each R$^{6a}$, R$^{6b}$, and R$^{6c}$ is independently selected from the group consisting of hydrogen, C$_{1-4}$ haloalkyl, unsubstituted C$_{1-4}$ alkyl, and acetyl,
or a pharmaceutically acceptable salt thereof.

In one embodiment of Formula IA, each R$^{6'}$ and R$^{6''}$ is methyl.

Provided is also a compound of Formula IB:

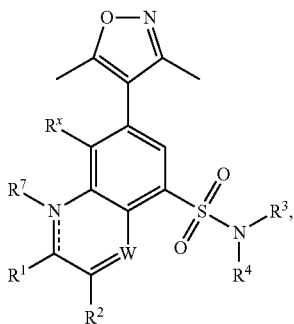

Formula IB wherein:
R$^1$, R$^2$, W, X, R$^3$, R$^4$, and R$^7$ are as defined in Formula I; and
R$^x$ is selected from the group consisting of hydrogen, halo, and unsubstituted C$_{1-4}$ alkyl,
or a pharmaceutically acceptable salt thereof.

Provided is also a compound of Formula IC:

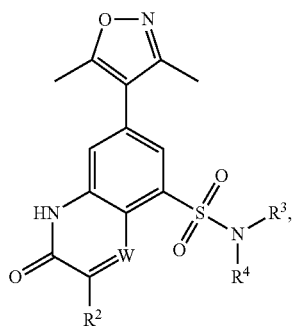

Formula IC wherein:
R$^2$ and W are as defined in Formula I;
R$^3$ is hydrogen; and
R$^4$ is selected from the group consisting of unsubstituted or substituted C$_{1-4}$ alkyl, C$_{1-8}$ haloalkyl, and unsubstituted or substituted C$_{3-8}$ cycloalkyl,
or a pharmaceutically acceptable salt thereof.

In some embodiments, W is CR$^W$, wherein R$^W$ is hydrogen.

Provided is also a compound of Formula ID:

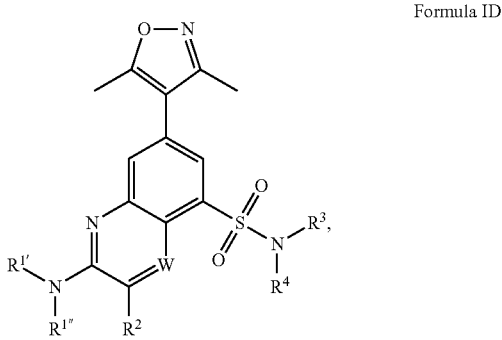

Formula ID wherein:
R$^2$, W, R$^3$ and R$^4$ are as defined in Formula I; and
each R$^{1'}$ and R$^{1''}$ is independently selected from the group consisting of hydrogen, unsubstituted or substituted C$_{1-4}$ alkyl, unsubstituted or substituted C$_{3-8}$ cycloalkyl, and unsubstituted or substituted C$_{3-8}$ heterocycloalkyl;
or R$^{1'}$ and R$^{1''}$ and the nitrogen atom to which they are attached join to form unsubstituted or substituted C$_{3-12}$ heterocycloalkyl; wherein the unsubstituted or substituted C$_{3-12}$ heterocycloalkyl has 1 to 3 heteroatoms selected from O, N, and S,
or a pharmaceutically acceptable salt thereof.

In some embodiments of Formula ID, R$^{1'}$ and R$^{1''}$ and the nitrogen atom to which they are attached join to form unsubstituted or substituted C$_{3-12}$ heterocycloalkyl, and wherein the unsubstituted or substituted C$_{3-12}$ heterocycloalkyl has 1 to 3 heteroatoms selected from N and O.

In some embodiments of Formula ID, R$^{1'}$ and R$^{1''}$ and the nitrogen atom to which they are attached join to form unsubstituted C$_{3-12}$ heterocycloalkyl, or substituted C$_{3-12}$ heterocycloalkyl with 1 to 3 substituents independently from the group consisting of halo, unsubstituted C$_{1-4}$ alkyl, and oxo. In certain embodiments, R$^{1'}$ and R$^{1''}$ and the nitrogen atom to which they are attached join to form unsubstituted or substituted piperazinyl, or unsubstituted or substituted morpholinyl.

Provided is also a compound of Formula I':

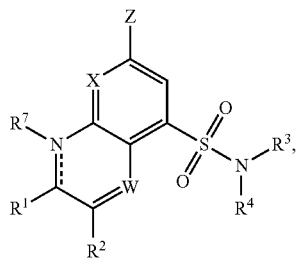

Formula I' wherein:
R$^1$ is selected from the group consisting of hydrogen, halo, C$_{1-4}$ haloalkyl, C$_{1-4}$ alkyl, C$_{3-8}$ cycloalkyl, C$_{3-8}$ heterocycloalkyl, NR$^{1a}$R$^{1b}$, OR$^{1c}$, and oxo;

wherein each $R^{1a}$ and $R^{1b}$ is independently selected from the group consisting of hydrogen, $C_{1-4}$ alkyl, $C_{3-8}$ cycloalkyl, and $C_{3-8}$ heterocycloalkyl;
or $R^{1a}$ and $R^{1b}$ and the nitrogen atom to which they are attached join to form $C_{3-12}$ heterocycloalkyl, wherein the $C_{3-12}$ heterocycloalkyl has 1 to 3 heteroatoms selected from the group consisting of oxygen, nitrogen and sulfur;
wherein $R^{1c}$ is $C_{1-4}$ alkyl;
$R^2$ is selected from the group consisting of hydrogen, halo, $C_{1-4}$ haloalkyl, cyano, $NR^{2a}R^{2b}$, carboxyl, $C(O)NR^{2a}R^{2b}$, $OR^{2c}$, $C_{1-6}$ alkyl, $C_{3-12}$ cycloalkyl, $C_{3-12}$ heterocycloalkyl, $C_{3-12}$ aryl, and $C_{3-12}$ heteroaryl;
wherein each $R^{2a}$, $R^{2b}$ and $R^{2c}$ is independently selected from the group consisting of hydrogen, $C_{1-4}$ haloalkyl, $C_{1-6}$ alkyl, $C_{3-12}$ cycloalkyl, and $C_{3-12}$ heterocycloalkyl;
or $R^{2a}$ and $R^{2b}$ and the nitrogen atom to which they are attached join to form $C_{3-12}$ heterocycloalkyl or $C_{3-12}$ heteroaryl, wherein each $C_{3-12}$ heterocycloalkyl and $C_{3-12}$ heteroaryl independently has 1 to 3 heteroatoms selected from the group consisting of oxygen, nitrogen and sulfur;
W is N or $CR^w$;
wherein $R^w$ is independently selected from the group consisting of hydrogen, $C_{1-4}$ haloalkyl, $C_{1-4}$ alkyl, and $C_{1-4}$ alkoxy;
X is N or $CR^x$;
wherein $R^x$ is independently selected from the group consisting of hydrogen, $C_{1-4}$ haloalkyl, $C_{1-4}$ alkyl, and $C_{1-4}$ alkoxy;
$R^3$ is selected from the group consisting of hydrogen and $C_{1-4}$ alkyl;
$R^4$ is selected from the group consisting of hydrogen, $C_{1-8}$ haloalkyl, $C_{1-8}$ alkyl, $C_{3-8}$ cycloalkyl, $C_{3-12}$ heterocycloalkyl, and $C_{3-12}$ heteroaryl;
or $R^3$ and $R^4$ and the nitrogen atom to which they are attached join to form $C_{3-12}$ heterocycloalkyl or $C_{3-12}$ heteroaryl, wherein each $C_{3-12}$ heterocycloalkyl and $C_{3-12}$ heteroaryl independently has 1 to 3 heteroatoms selected from the group consisting of oxygen, nitrogen and sulfur;
$R^7$ is hydrogen or absent; and
Z is isoxazolyl or pyrazolyl, wherein each isoxazolyl and pyrazolyl is independently unsubstituted or substituted with 1 or 2 substituents selected from the group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ hydroxyalkoxy, —$CH_2$—$C_3$-$C_6$ cycloalkyl, —$C(O)NH_2$, —$C(O)NH$—$C_1$-$C_{16}$ alkyl, and —$C(O)N(C_1$-$C_6$ alkyl$)_2$;
wherein each $C_{1-4}$ alkyl, $C_{1-6}$ alkyl, $C_{1-8}$ alkyl, and $C_{1-4}$ alkoxy is independently unsubstituted or substituted with 1 to 5 substituents selected from the group consisting of $C_2$-$C_6$-alkenyl, $C_2$-$C_6$-alkynyl, $C_1$-$C_6$-alkoxy, $C_3$-$C_{10}$-cycloalkyl, $C_4$-$C_{10}$-cycloalkenyl, acyl, amino, azido, cyano, halogen, $C_1$-$C_4$-haloalkyl, hydroxy, oxo, carboxy, thiol, $C_6$-$C_{10}$-aryl, $C_6$-$C_{10}$-aryloxy, 5- to 10-membered heteroaryl, 5- to 10-membered heteroaryloxy, 4- to 10-membered heterocycloalkyl, 4- to 10-membered heterocycloalkoxy, nitro, —SO-alkyl, —SO-cycloalkyl, —SO-(4- to 10-membered heterocycloalkyl), —SO—($C_6$-$C_{10}$-aryl), —SO-(5- to 10-membered heteroaryl), —$SO_2$—($C_1$-$C_6$-alkyl), —$SO_2$—($C_3$-$C_{10}$-cycloalkyl), —$SO_2$-(4- to 10-membered heterocycloalkyl), —$SO_2$—($C_6$-$C_{10}$-aryl), and —$SO_2$-(5- to 8-membered heteroaryl); and wherein each $C_{3-8}$ cycloalkyl, $C_{3-12}$ cycloalkyl, $C_{3-8}$ heterocycloalkyl, $C_{3-12}$ heterocycloalkyl, $C_{3-12}$ aryl, and $C_{3-12}$ heteroaryl is independently unsubstituted or substituted with 1 to 5 substituents independently selected from the group consisting of $C_1$-$C_6$-alkyl, $C_2$-$C_6$-alkenyl, $C_2$-$C_6$-alkynyl, $C_1$-$C_6$-alkoxy, $C_3$-$C_8$-cycloalkyl, $C_4$-$C_8$-cycloalkenyl, acyl, acylamino, acyloxy, amino, aminocarbonyl, $C_1$-$C_6$-alkoxycarbonylamino, azido, cyano, halogen, $C_1$-$C_4$-haloalkyl, hydroxy, oxo, thiocarbonyl, carboxy, $C_1$-$C_6$-carboxyalkyl, $C_6$-$C_{10}$-arylthio, heteroarylthio, heterocyclylthio, thiol, $C_6$-$C_{10}$-aryl, $C_6$-$C_{10}$-aryloxy, 5- to 10-membered heteroaryl, aminosulfonyl, aminocarbonyl amino, 5- to 10-membered heteroaryloxy, 3- to 8-membered heterocycloalkyl, 3- to 8-membered heterocycloalkoxy, hydroxyamino, alkoxyamino, nitro, —SO—($C_1$-$C_6$-alkyl), —SO—($C_6$-$C_{10}$-aryl), —SO-(5- to 10-membered heteroaryl), —$SO_2$—($C_1$-$C_6$-alkyl), —$SO_2$—($C_6$-$C_{10}$-aryl), and —$SO_2$-(5- to 10-membered heteroaryl); and
or a pharmaceutically acceptable salt thereof.
Provided is also a compound of Formula IE or IF:

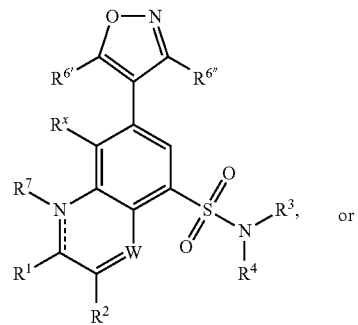

Formula IE

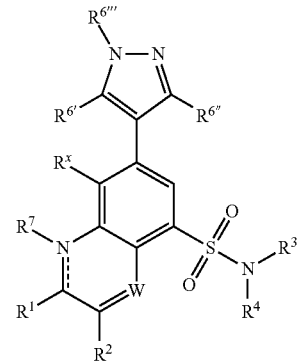

Formula IF wherein:
W is $CR^w$ or N;
$R^w$ is selected from the group consisting of hydrogen, $C_{1-4}$ haloalkyl, $C_{1-4}$ alkyl, and $C_{1-4}$ alkoxy, wherein the $C_{1-4}$ alkyl and $C_{1-4}$ alkoxy are independently unsubstituted or substituted with 1 to 4 substituents independently selected from the group consisting of halogen, —OH, =O, CN, $NH_2$, $C_2$-$C_6$ alkenyl, $C_2$-$C_6$ alkynyl, $C_1$-$C_3$ haloalkyl, and $C_{1-4}$ alkoxy;
$R^x$ is selected from the group consisting of hydrogen, halogen, $C_{1-4}$ haloalkyl, $C_{1-4}$ alkyl, and $C_{1-4}$ alkoxy, wherein the $C_{1-4}$ alkyl and $C_{1-4}$ alkoxy are independently unsubstituted or substituted with 1 to 4 substituents independently selected from the group consisting of halogen, —OH, =O, CN, NH$_2$, C$_2$-C$_6$ alkenyl, C$_2$-C$_6$ alkynyl, C$_1$-C$_3$ haloalkyl, and C$_{1-4}$ alkoxy;

R$^1$ is selected from the group consisting of hydrogen, =O, C$_1$-C$_3$ haloalkyl, halogen, C$_3$-C$_6$-cycloalkyl, NR$^{1a}$R$^{1b}$, OR$^{1c}$,

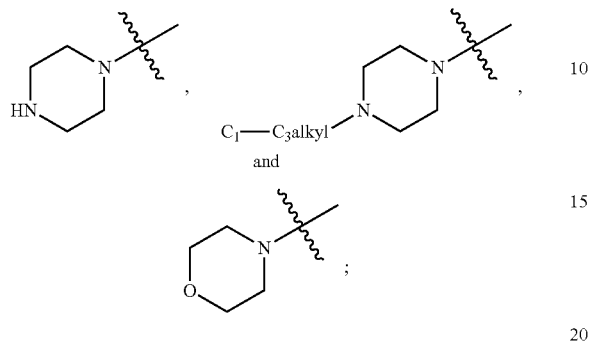

wherein each R$^{1a}$, R$^{1b}$, and R$^{1c}$ is independently selected from the group consisting of hydrogen, unsubstituted C$_{1-4}$ alkyl, or C$_{1-4}$ alkyl substituted with C$_3$-C$_8$ cycloalkyl;

R$^2$ is selected from the group consisting of hydrogen, halogen, CN, C$_3$-C$_8$ cycloalkyl, C$_1$-C$_6$ hydroxyalkyl, NR$^{2a}$R$^{2b}$, carboxyl, C(O)NR$^{2a}$R$^{2b}$, OR$^{2c}$, 4- to 8-membered heterocycloalkyl having 1 or 2 ring heteroatoms selected from the group consisting of oxygen and nitrogen, and 5- or 6-membered heteroaryl having 1 or 2 ring nitrogen atoms, wherein each C$_3$-C$_8$ cycloalkyl, 4- to 8-membered heterocycloalkyl, and 5- or 6-membered heteroaryl is independently unsubstituted or substituted with 1 to 3 substituents selected from the group consisting of OH, halogen, C$_1$-C$_6$ alkoxy, C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

wherein each R$^{2a}$, R$^{2b}$, and R$^{2c}$ is independently hydrogen or C$_1$-C$_6$ alkyl, wherein the C$_1$-C$_6$ alkyl is unsubstituted or substituted with 1 to 3 substituents selected from the group consisting of OH, halogen, C$_1$-C$_6$ alkoxy, C$_1$-C$_4$ haloalkyl, C$_3$-C$_6$ cycloalkyl, —O—C$_3$-C$_6$ cycloalkyl, —NH$_2$, —NH(C$_1$-C$_6$ alkyl), —N(C$_1$-C$_6$ alkyl)$_2$, —NH—(C$_1$-C$_4$ haloalkyl), —N(C$_1$-C$_4$ haloalkyl)$_2$, 4- to 8-membered heterocycloalkyl having 1 or 2 ring heteroatoms selected from the group consisting of oxygen or nitrogen, and 5- or 6-membered heteroaryl having 1 or 2 ring nitrogen atoms, wherein the 4- to 8-membered heterocycle and 5- or 6-membered heteroaryl is unsubstituted or substituted with 1 to 3 substituents selected from the group consisting of OH, =O, halogen, C$_1$-C$_6$ alkyl, C$_1$-C$_6$ alkoxy, C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

R$^3$ is hydrogen or C$_1$-C$_3$ alkyl;

R$^4$ is:
a) hydrogen,
b) C$_1$-C$_8$ alkyl, wherein the C$_1$-C$_8$ alkyl is unsubstituted or substituted with 1 to 3 substituents selected from the group consisting of =O, OH, CN, halogen, C$_1$-C$_6$ alkoxy, C$_1$-C$_4$ haloalkyl, C$_3$-C$_6$ cycloalkyl, —O—(C$_3$-C$_6$ cycloalkyl), —NH$_2$, —NH(C$_1$-C$_6$ alkyl), —N(C$_1$-C$_6$ alkyl)$_2$, —NH—(C$_1$-C$_4$ haloalkyl), —N(C$_1$-C$_4$ haloalkyl)$_2$, phenyl, 4- to 8-membered heterocycloalkyl having 1 or 2 ring heteroatoms selected from the group consisting of oxygen, sulfur, and nitrogen, and 5- or 6-membered heteroaryl having 1 or 2 ring heteroatoms selected from the group consisting of oxygen, sulfur and nitrogen, wherein each C$_3$-C$_6$ cycloalkyl, —O—(C$_3$-C$_6$ cycloalkyl), phenyl, 4- to 8-membered heterocyclic, and 5- or 6-membered heteroaryl is independently unsubstituted or substituted with 1 to 3 substituents selected from the group consisting of OH, =O, CN, halogen, C$_1$-C$_6$ alkyl, C$_1$-C$_6$ alkoxy, —(C$_1$-C$_6$ alkyl)-O—(C$_1$-C$_6$ alkyl), C$_1$-C$_4$ haloalkyl, —O—C$_1$-C$_4$ haloalkyl, NH$_2$, —NH(C$_1$-C$_6$ alkyl), and —N(C$_1$-C$_6$ alkyl)$_2$;

c) C$_3$-C$_7$ cycloalkyl, wherein the C$_3$-C$_7$ cycloalkyl is unsubstituted or substituted with 1 to 3 substituents selected from the group consisting of:
i) OH, =O, CN, halogen, C$_1$-C$_6$ alkyl, C$_1$-C$_6$ alkoxy, —(C$_1$-C$_6$ alkyl)-O—(C$_1$-C$_6$ alkyl), C$_1$-C$_4$ haloalkyl, —O—C$_1$-C$_4$ haloalkyl, NH$_2$, and —NH(C$_1$-C$_6$ alkyl), —N(C$_1$-C$_6$ alkyl)$_2$, —NHC(O)OH, —NHCO$_2$—C$_1$-C$_6$ alkyl, —O-benzyl,
ii) —CO$_2$H, —C(O)NH(C$_1$-C$_6$ alkyl), —C(O)N(C$_1$-C$_6$ alkyl)$_2$, wherein C$_1$-C$_6$ alkyl is unsubstituted or substituted with 1 to 3 substituents selected from the group consisting of OH, halogen, —NH$_2$, —NH(C$_1$-C$_6$ alkyl), and —N(C$_1$-C$_6$ alkyl)$_2$;

iii) —C(O)NH—C$_3$-C$_6$ cycloalkyl, —C(O)N(C$_1$-C$_3$ alkyl)-C$_3$-C$_6$ cycloalkyl,

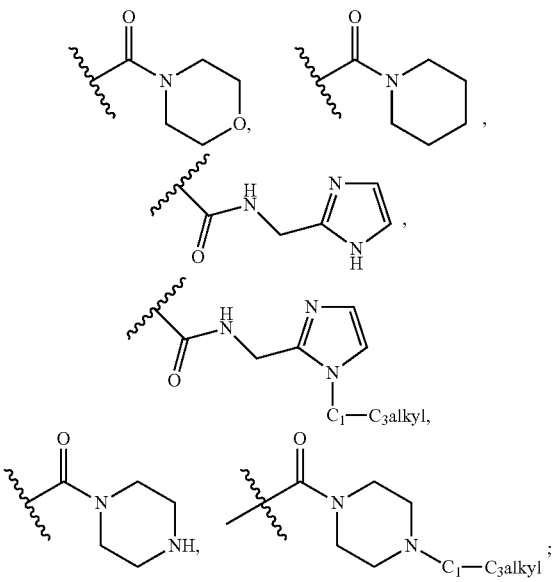

iv) phenyl, wherein the phenyl is unsubstituted or substituted with 1 to 4 substituents independently selected from the group consisting of halogen, C$_1$-C$_6$ alkyl, C$_1$-C$_6$ alkoxy, C$_1$-C$_4$ haloalkyl, CO$_2$H, —CO$_2$—C$_1$-C$_6$ alkyl, =O, and —OH;

d) 5- to 7-membered heterocycloalkyl or heteroaryl having 1 or 2 ring atoms selected from the group consisting of nitrogen and oxygen, wherein each heterocycloalkyl and heteroaryl is independently unsubstituted or substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH;

or $R^3$ and $R^4$ and the nitrogen to which they are bound are joined to form a 4- to 6-membered heterocycloalkyl having 1 or 2 ring nitrogen atoms, wherein 4- to 6-membered heterocycloalkyl is unsubstituted or substituted with 1 to 4 substituents independently selected from the group consisting of halogen, $C_1$-$C_6$ alkyl, $C_1$-$C_6$ alkoxy, haloalkyl, $CO_2H$, —$CO_2$—$C_1$-$C_6$ alkyl, =O, and —OH;

$R^{6'}$ is hydrogen, $C_1$-$C_6$ alkyl, —$CH_2OH$, or $C_3$-$C_6$ cycloalkyl;

$R^{6''}$ is hydrogen, $C_1$-$C_6$ alkyl, or $C_3$-$C_6$ cycloalkyl;

$R^{6'''}$ is hydrogen, $C_1$-$C_6$ alkyl, or $C_3$-$C_6$ cycloalkyl; and $R^7$ is hydrogen or absent;

or a pharmaceutically acceptable salt thereof.

In some embodiments of Formula IE or IF, $R^4$ is hydrogen or tetrahydrofuran.

In some embodiments of Formula IE or IF, $R^4$ is $C_1$-$C_8$ alkyl. In certain embodiments, the $C_1$-$C_8$ alkyl is unsubstituted or substituted with 1 to 3 substituents. In certain embodiments, the $C_1$-$C_8$ alkyl may be substituted with =O, OH, CN, halogen, $C_1$-$C_6$ alkoxy, $C_1$-$C_4$ haloalkyl, $C_3$-$C_6$ cycloalkyl, —O—($C_3$-$C_6$ cycloalkyl), —$NH_2$, —$NH(C_1$-$C_6$ alkyl), —$N(C_1$-$C_6$ alkyl)$_2$, —NH—($C_1$-$C_4$ haloalkyl), —$N(C_1$-$C_4$ haloalkyl)$_2$, phenyl, 4- to 8-membered heterocycloalkyl having 1 or 2 ring heteroatoms selected from the group consisting of oxygen, sulfur, and nitrogen, and 5- or 6-membered heteroaryl having 1 or 2 ring heteroatoms selected from the group consisting of oxygen, sulfur and nitrogen. In one embodiment, each $C_3$-$C_6$ cycloalkyl, —O—($C_3$-$C_6$ cycloalkyl), phenyl, 4- to 8-membered heterocyclic, and 5- or 6-membered heteroaryl substituent is independently unsubstituted or further substituted with 1 to 3 substituents selected from the group consisting of OH, =O, CN, halogen, $C_1$-$C_6$ alkyl, $C_1$-$C_6$ alkoxy, —($C_1$-$C_6$ alkyl)-O—($C_1$-$C_6$ alkyl), $C_1$-$C_4$ haloalkyl, —O—$C_1$-$C_4$ haloalkyl, $NH_2$, —NH($C_1$-$C_6$ alkyl), and —$N(C_1$-$C_6$ alkyl)$_2$.

In some embodiments of Formula IE or IF, $R^4$ is $C_3$-$C_7$ cycloalkyl. In certain embodiments, the $C_3$-$C_7$ cycloalkyl is unsubstituted or substituted with 1 to 3 substituents. In one embodiment, the $C_3$-$C_7$ cycloalkyl may be substituted with OH, =O, CN, halogen, $C_1$-$C_6$ alkyl, $C_1$-$C_6$ alkoxy, —($C_1$-$C_6$ alkyl)-O—($C_1$-$C_6$ alkyl), $C_1$-$C_4$ haloalkyl, —O—$C_1$-$C_4$ haloalkyl, $NH_2$, and —NH($C_1$-$C_6$ alkyl), —$N(C_1$-$C_6$ alkyl)$_2$, —NHC(O)OH, —$NHCO_2$—$C_1$-$C_6$ alkyl, or —O-benzyl. In another embodiment, the $C_3$-$C_7$ cycloalkyl may be substituted with —$CO_2H$, —C(O)NH($C_1$-$C_6$ alkyl), —C(O)N($C_1$-$C_6$ alkyl)$_2$, wherein the $C_1$-$C_6$ alkyl substituent is unsubstituted or further substituted with 1 to 3 substituents selected from the group consisting of OH, halogen, —$NH_2$, —NH($C_1$-$C_6$ alkyl), and —$N(C_1$-$C_6$ alkyl)$_2$. In yet another embodiment, the $C_3$-$C_7$ cycloalkyl may be substituted with —C(O)NH—$C_3$-$C_6$ cycloalkyl, —C(O)N($C_1$-$C_3$ alkyl)-$C_3$-$C_6$ cycloalkyl,

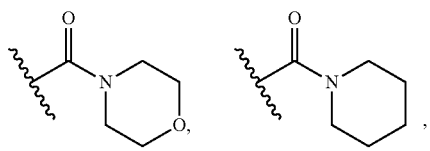

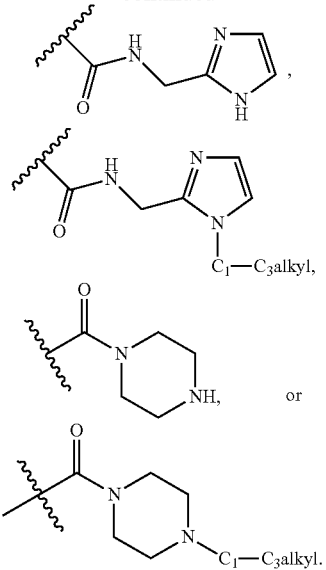

In yet another embodiment, the $C_3$-$C_7$ cycloalkyl may be substituted with phenyl, wherein the phenyl substituent is unsubstituted or further substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH.

In some embodiments of Formula IE or IF, $R^4$ is 5- to 7-membered heterocycloalkyl or heteroaryl having 1 or 2 ring atoms selected from the group consisting of nitrogen and oxygen. In certain embodiments, each heterocycloalkyl and heteroaryl is independently unsubstituted or substituted with 1 to 4 substituents independently selected from the group consisting of halogen, $C_1$-$C_6$ alkyl, $C_1$-$C_6$ alkoxy, $C_1$-$C_4$ haloalkyl, $CO_2H$, —$CO_2$—$C_1$-$C_6$ alkyl, =O, and —OH.

In some embodiments, the compound is a compound of Formula IE, wherein:

W is CH or N;

$R^x$ is H or Cl;

$R^1$ is selected from the group consisting of hydrogen, =O, —$CHF_2$, Cl, —$OCH_3$, cyclopropyl, $NH_2$, —NH—$CH_2$-cyclopropyl, —O—$CH_2$-cyclopropyl,

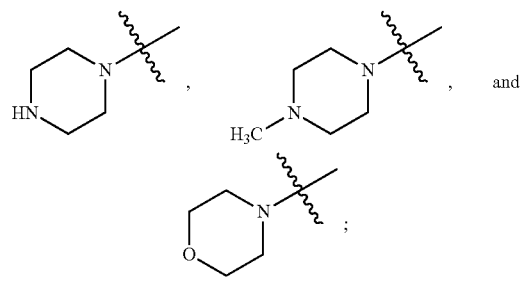

$R^2$ is selected from the group consisting of hydrogen, Br, CN, cyclopropyl, —$CH_2OH$, —$CH(CH_3)_2OH$, $CO_2H$, —$C(O)NH_2$, —$C(O)N(CH_3)_2$, $NH_2$, —$CH_2NH_2$, —$NHCH_3$, —$N(CH_3)_2$, —$NHCH(CH_3)_2$, —$NHCH_2CH_2OH$, —$NHCH_2CH_2OCH_3$, $NHCH_2CH_2OCH_2CH_2OH$, —$NHCH_2CH_2NH_2$, —$NHCH_2CH_2N(CH_3)_2$, $NHCH_2CH_2N(CH_3)_2$, —NH—$CH_2$-cyclopropyl, —$NHCH_2CHF_2$, —NHCH

33
(CH₃)₂CH₂OH, —NHCH(CH₃)₂NH₂, —NHCH₂CH(CH₃)₂CH₂NH₂, —NHCH(CH₂OH)₂, NHCH₂CH(OH)CH₂OH,
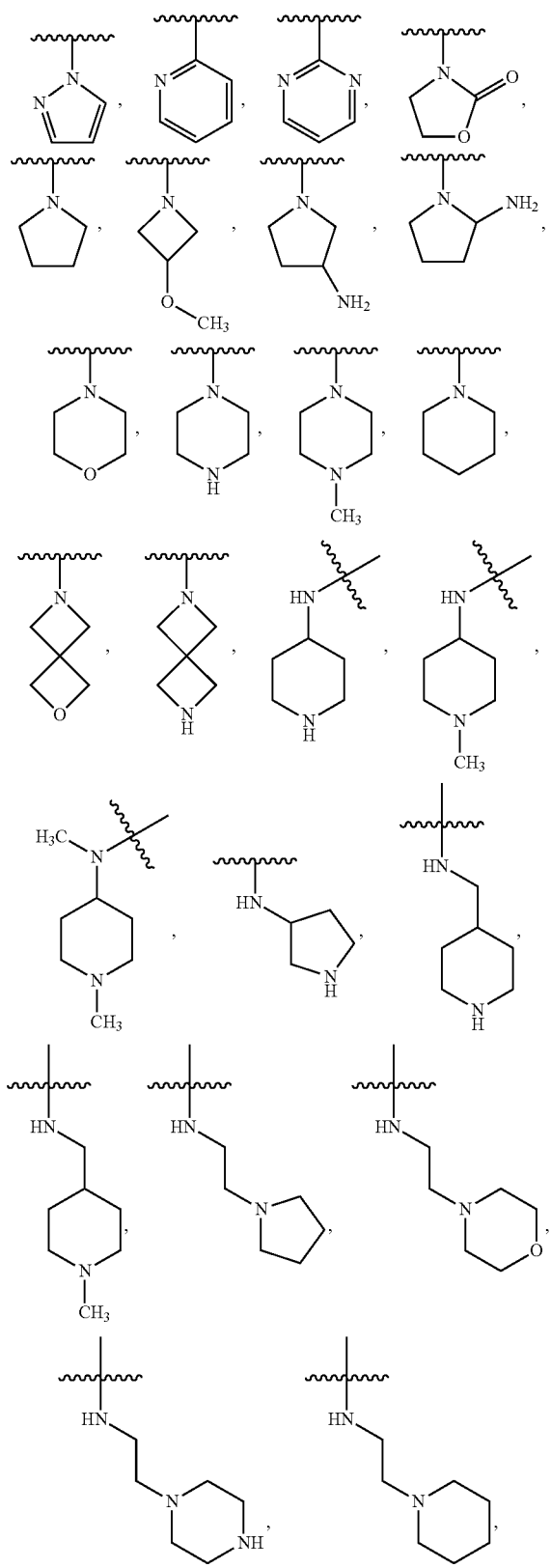
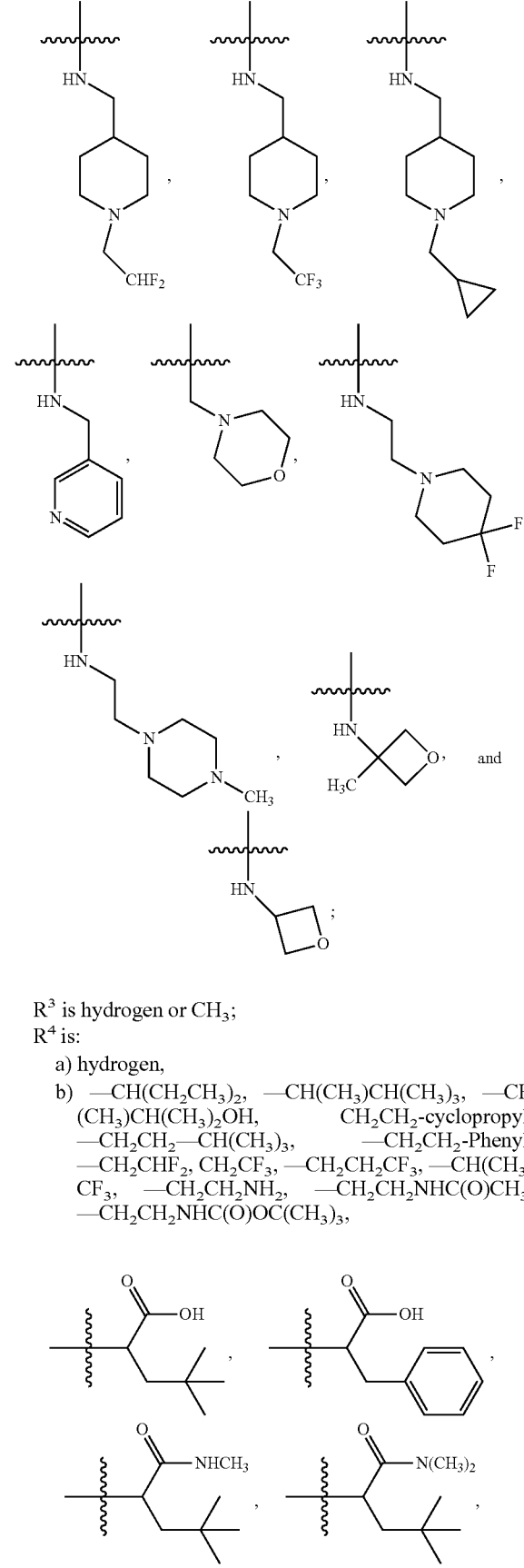
$R^3$ is hydrogen or $CH_3$;
$R^4$ is:
a) hydrogen,
b) —CH(CH₂CH₃)₂, —CH(CH₃)CH(CH₃)₃, —CH(CH₃)CH(CH₃)₂OH, CH₂CH₂-cyclopropyl, —CH₂CH₂—CH(CH₃)₃, —CH₂CH₂-Phenyl, —CH₂CHF₂, CH₂CF₃, —CH₂CH₂CF₃, —CH(CH₃)CF₃, —CH₂CH₂NH₂, —CH₂CH₂NHC(O)CH₃, —CH₂CH₂NHC(O)OC(CH₃)₃, -continued

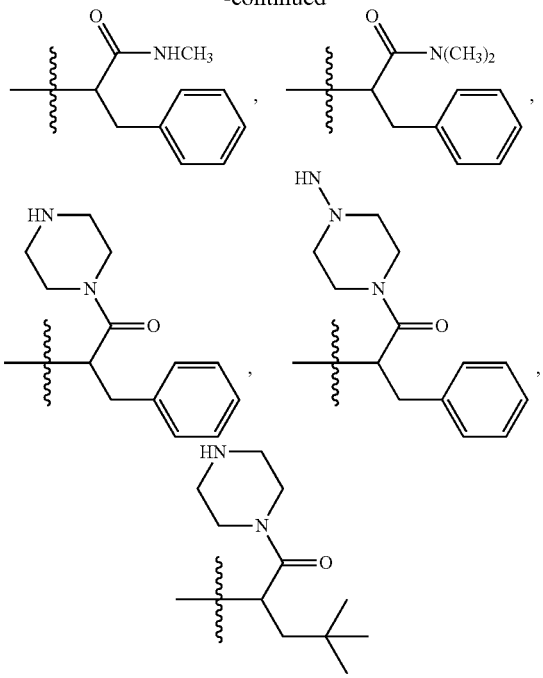

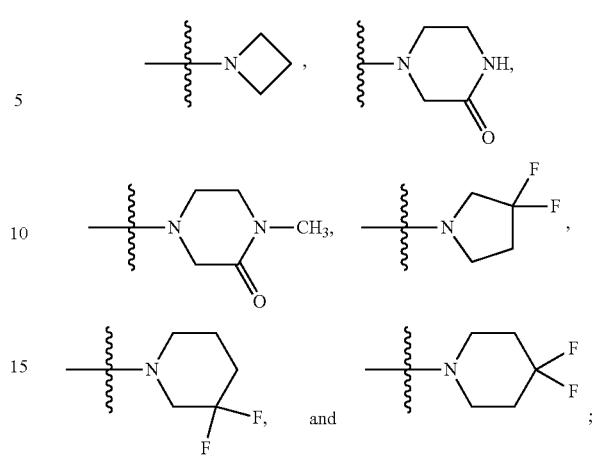

c) $C_3$-$C_7$ cycloalkyl, wherein $C_3$-$C_7$ cycloalkyl is unsubstituted or substituted with 1 or 2 substituents independently selected from the group consisting of F, $CH_3$, $CF_3$, CN, OH, —$CH_2$—O—$CH_3$, —O-benzyl, $CO_2H$, —C(O)NH—$CH_3$, —C(O)NH—CH($CH_3$)$_2$, —C(O)NH—CH—$CH_2$—$NH_2$,

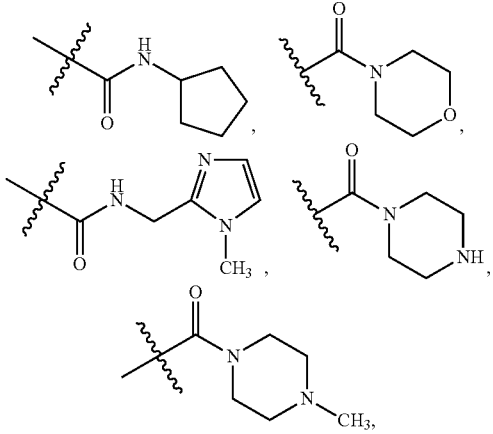

$NH_2$, —NH—$CH_2$—$CH_3$, —N($CH_2$—$CH_3$)$_2$, —NH—C(O)O-t-butyl, —NH—C(O)O-ethyl, —NH—C(O)$CH_3$, and phenyl optionally substituted with F; or d) 5-7-membered heterocycloalkyl or heteroaryl having 1 or 2 ring atoms selected from the group consisting of nitrogen and oxygen,
   wherein each heterocycloalkyl and heteroaryl is independently unsubstituted or substituted with =O, $CH_3$, or —$CO_2$-(tert-butyl);

or $R^3$ and $R^4$ and the nitrogen to which they are bound are fused to form a heterocycloalkyl selected from the group consisting of;

$R^{6'}$ is hydrogen, $CH_3$, —$CH_2OH$, or cyclopropyl; and
$R^{6''}$ is hydrogen, $CH_3$, or cyclopropyl;
or a pharmaceutically acceptable salt thereof.

In one embodiment of Formula IE, $R^4$ is hydrogen or tetrahydrofuran.

In other embodiments of Formula IE, $R^4$ is —CH($CH_2CH_3$)$_2$, —CH($CH_3$)CH($CH_3$)$_3$, —CH($CH_3$)CH($CH_3$)$_2$OH, —$CH_2CH_2$-cyclopropyl, —$CH_2CH_2$—CH($CH_3$)$_3$, —$CH_2CH_2$-Phenyl, —$CH_2CHF_2$, —$CH_2CF_3$, —$CH_2CH_2CF_3$, —CH($CH_3$)$CF_3$, —$CH_2CH_2NH_2$, —$CH_2CH_2NHC(O)CH_3$, —$CH_2CH_2NHC(O)OC(CH_3)_3$,

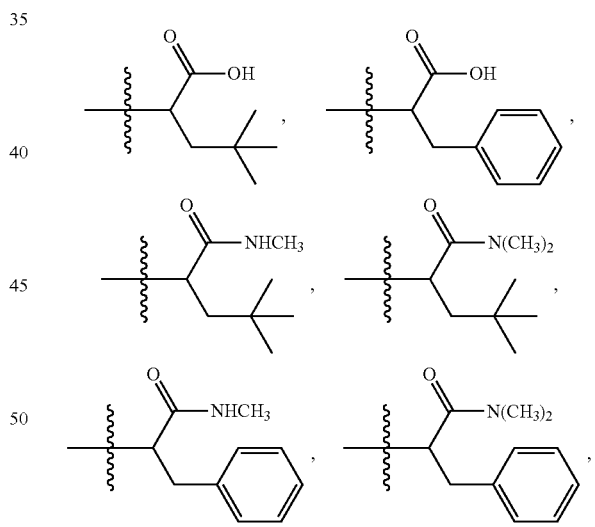

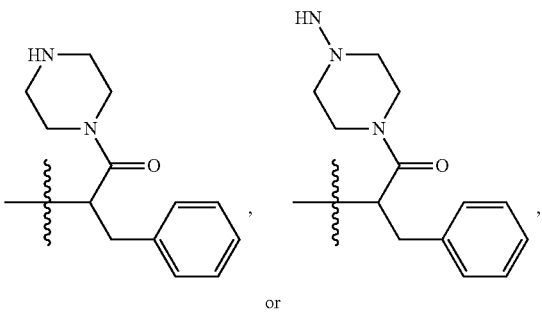

or

-continued

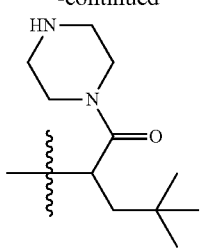

In yet other embodiments of Formula IE, $R^4$ is $C_3$-$C_7$ cycloalkyl, wherein $C_3$-$C_7$ cycloalkyl is unsubstituted or substituted with 1 or 2 substituents. In certain embodiments, the substituents of the $C_3$-$C_7$ cycloalkyl may be independently selected from the group consisting of F, $CH_3$, $CF_3$, CN, OH, —$CH_2$—O—$CH_3$, —O-benzyl, $CO_2H$, —C(O)NH—$CH_3$, —C(O)NH—CH($CH_3$)$_2$, —C(O)NH—CH—$CH_2$—$NH_2$, $NH_2$, —NH—$CH_2$—$CH_3$, —N($CH_2$—$CH_3$)$_2$, —NH—C(O)O-t-butyl, —NH—C(O)O-ethyl, —NH—C(O)$CH_3$, and phenyl optionally substituted with F.

In yet other embodiments of Formula IE, $R^4$ is 5-7-membered heterocycloalkyl or heteroaryl having 1 or 2 ring atoms selected from the group consisting of nitrogen and oxygen. In certain embodiments, each heterocycloalkyl and heteroaryl is independently unsubstituted or substituted with =O, $CH_3$, or —$CO_2$-(tert-butyl).

In other embodiments, the compound is a compound of Formula IE, wherein:

W is CH or N;

$R^x$ is H or Cl;

$R^1$ is selected from the group consisting of hydrogen, =O, —$CHF_2$, Cl, —$OCH_3$, cyclopropyl, $NH_2$, —NH—$CH_2$-cyclopropyl, —O—$CH_2$-cyclopropyl, and

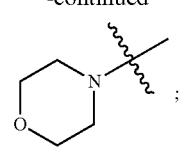

$R^2$ is selected from hydrogen, Br, CN, cyclopropyl, —$CH_2OH$, —CH($CH_3$)$_2$OH, $CO_2H$, —C(O)$NH_2$, —C(O)N($CH_3$)$_2$, $NH_2$, —$CH_2NH_2$, —$NHCH_3$, —N($CH_3$)$_2$, —NHCH($CH_3$)$_2$, —$NHCH_2CH_2OH$, —$NHCH_2CH_2OCH_3$, —$NHCH_2CH_2OCH_2CH_2OH$, —$NHCH_2CH_2NH_2$, —$NHCH_2CH_2N(CH_3)_2$, —$NHCH_2CH_2CH_2N(CH_3)_2$, —NH—$CH_2$-cyclopropyl, —$NHCH_2CHF_2$, —$NHCH(CH_3)_2CH_2OH$, —$NHCH(CH_3)_2NH_2$, —$NHCH_2CH(CH_3)_2CH_2NH_2$, —$NHCH(CH_2OH)_2$, —$NHCH_2CH(OH)CH_2OH$.

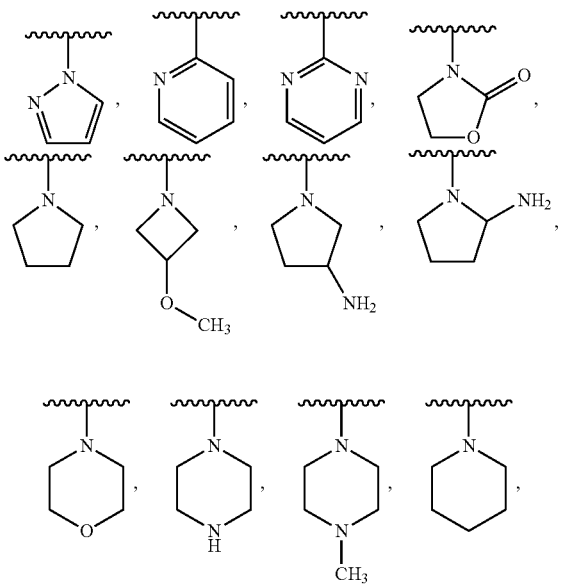

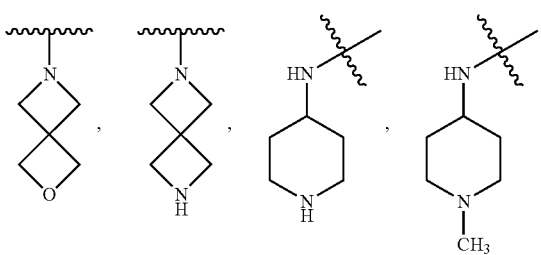

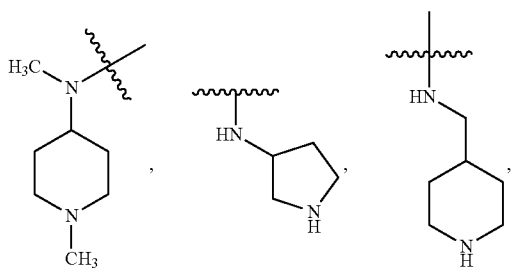

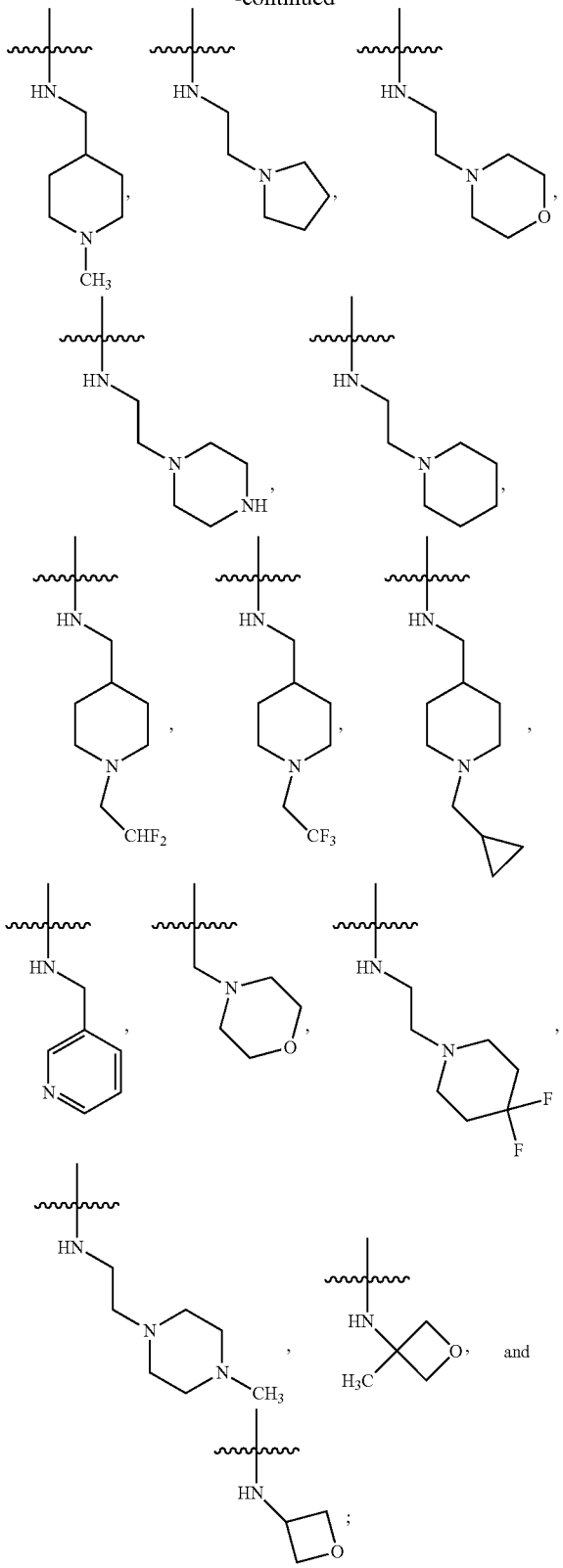

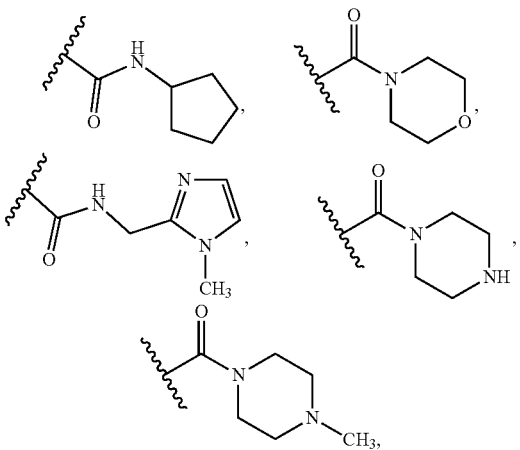

independently selected from the group consisting of F, CH₃, CF₃, CN, OH, —CH₂—O—CH₃, —O-benzyl, CO₂H, —C(O)NH—CH₃, —C(O)NH—CH(CH₃)₂, —C(O)NH—CH—CH₂—NH₂.

NH₂, —NH—CH₂—CH₃, —N(CH₂—CH₃)₂, —NH—C(O)O-t-butyl, —NH—C(O)O-ethyl, —NH—C(O)CH₃, and phenyl optionally substituted with F; or b) 5-7-membered heterocycloalkyl or heteroaryl having 1 or 2 ring atoms selected from the group consisting of nitrogen and oxygen,
  wherein each heterocycloalkyl and heteroaryl is independently unsubstituted or substituted with =O, CH₃, or —CO₂-(tert-butyl);

or R³ and R⁴ and the nitrogen to which they are bound are fused to form a heterocycloalkyl selected from the group consisting of;

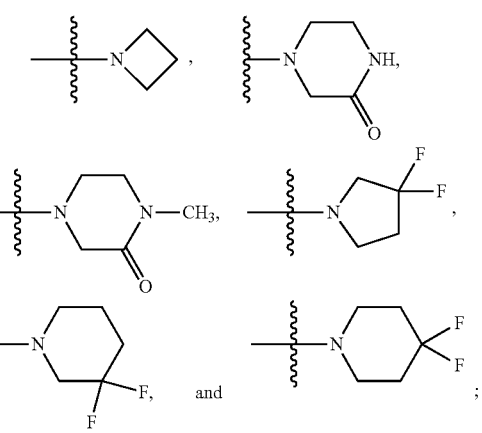

R⁶' is hydrogen, CH₃, —CH₂OH, or cyclopropyl; and
R⁶" is hydrogen, CH₃ or cyclopropyl;
or a pharmaceutically acceptable salt thereof.

In some embodiments of Formula IE, R⁴ is C₃-C₇ cycloalkyl, wherein the C₃-C₇ cycloalkyl is unsubstituted or substituted with 1 or 2 substituents. The substituents for the C₃-C₇ cycloalkyl may be independently selected from the group consisting of F, CH₃, CF₃, CN, OH, —CH₂—O—CH₃, —O-benzyl, CO₂H, —C(O)NH—CH₃, —C(O)NH—CH(CH₃)₂, —C(O)NH—CH—CH₂—NH₂, R³ is hydrogen or CH₃;
R⁴ is:
  a) C₃-C₇ cycloalkyl, wherein the C₃-C₇ cycloalkyl is unsubstituted or substituted with 1 or 2 substituents

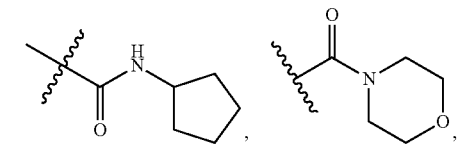

,

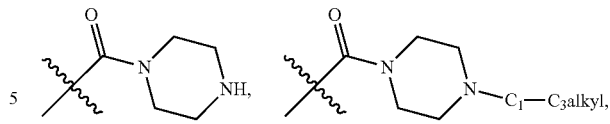

and

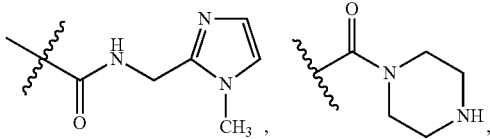

,

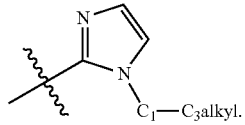

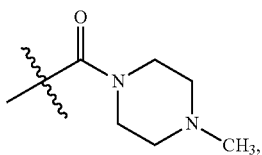

$NH_2$, —NH—$CH_2$—$CH_3$, —N($CH_2$—$CH_3$)$_2$, —NH—C(O)O-t-butyl, —NH—C(O)O-ethyl, —NH—C(O)$CH_3$, and phenyl optionally substituted with F.

In other embodiments of Formula IE, $R^4$ is 5-7-membered heterocycloalkyl or heteroaryl having 1 or 2 ring atoms selected from the group consisting of nitrogen and oxygen. In one embodiment, each heterocycloalkyl and heteroaryl is independently unsubstituted or substituted with =O, $CH_3$, or —$CO_2$-(tert-butyl).

In certain embodiments of Formula IE and ID, $R^{6''}$ and $R^{6'''}$ are both $CH_3$. In certain embodiments of Formula IE and ID, $R^{6''}$ and $R^{6'''}$ are both $CH_3$; and W is CH. In certain embodiments of Formula IE and ID, $R^{6''}$ and $R^{6'''}$ are both $CH_3$; and W is N.

In certain embodiments of Formula I, IA, IB, IC, ID, I', IE and IF, $R^4$ is cyclopropyl, cyclobutyl, cyclopentyl, cyclohexyl, or bicyclo[2.2.1]heptanyl. In certain embodiments of Formula I, IA, IB, IC, ID, IE and IF, $R^4$ is cyclopropyl, cyclobutyl, cyclopentyl, or bicyclo[2.2.1]heptanyl. In one embodiment of Formula I, IA, TB, IC, ID, I', IE and IF, $R^4$ is cyclopentyl.

In yet other embodiments of Formula I, IA, IB, IC, ID, I', IE and IF:
a) $R^4$ is cyclopropyl, cyclobutyl, cyclopentyl, cyclohexyl, or bicyclo[2.2.1]heptanyl;
b) $R^4$ is cyclopropyl, cyclobutyl, cyclopentyl, or bicyclo [2.2.1]heptanyl;
c) $R^4$ is cyclopropyl, cyclobutyl, or cyclopentyl ring; or
d) $R^4$ is cyclopentyl;
wherein each cyclopropyl, cyclobutyl, cyclopentyl, cyclohexyl, or bicyclo[2.2.1]heptanyl rings is independently unsubstituted or substituted with 1 to 4 substituents selected from the group consisting of halogen, $C_1$-$C_6$ alkyl, $C_1$-$C_6$ alkoxy, $CF_3$, —$OCF_3$, OH, $NH_2$, —NH($C_1$-$C_6$ alkyl), —N($C_1$-$C_6$ alkyl)$_2$, CN, phenyl substituted with 1 to 3 halogen atoms, —C(O)—NH—$CH_2$—($C_1$-$C_6$ alkyl), —C(O)—NH—$CH_2$—($C_3$-$C_6$ cycloalkyl), —NHC(O)—($C_1$-$C_6$ alkyl), —$CH_2$—O—($C_1$-$C_6$ alkyl), In yet other embodiments of Formula I, IA, IB, IC, ID, I', IE or IF, $R^4$ is unsubstituted cyclopropyl, unsubstituted cyclobutyl, unsubstituted cyclopentyl, unsubstituted cyclohexyl, or unsubstituted bicyclo[2.2.1]heptanyl. In yet other embodiments of Formula I, IA, IB, IC, ID, I', IE or IF, $R^4$ is unsubstituted cyclopropyl, unsubstituted cyclobutyl, unsubstituted cyclopentyl, or unsubstituted bicyclo[2.2.1]heptanyl. In one embodiment of Formula I, IA, IB, IC, ID, I', IE or IF, $R^4$ is unsubstituted cyclopentyl.

It is understood that any descriptions of a variable of Formula I, IA, IB, IC, ID, I', IE or IF (e.g., $R^1$, $R^{1a}$, $R^{1b}$, $R^2$, $R^{2a}$, $R^{2b}$, $R^{2c}$, W, $R^w$, X, $R^x$, $R^3$, $R^4$, $R^{4a}$, $R^{4b}$, $R^{4c}$, and Z) may be combined with any descriptions of any other variable(s) of Formula I, IA, IB, IC, ID, I', IE or IF the same as if each and every combination were specifically and individually listed. For example, it should be understood that any of the embodiments described above for $R^4$ may be combined with any embodiments for the other variables of Formula I, IA, IB, IC, ID, I', IE or IF the same as if each and every combination were specifically and individually listed. In one exemplary embodiment of Formula IE or IF where $R^{6''}$ and $R^6$ are both $CH_3$, and W is CH, $R^4$ can be either: (i) cyclopropyl, cyclobutyl, cyclopentyl, cyclohexyl, or bicyclo[2.2.1]heptanyl substituted as described for the specific embodiment; or (ii) $R^4$ is unsubstituted cyclopentyl ring, and all other variables are as described in Formula IE or IF.

Representative compounds of Formula I, IA, IB, IC, ID, IE or IF are shown in Table 1 below. The compounds in Table 1 were named using ChemBioDraw Ultra 12.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of Formula I, IA, IB, IC, ID, I', IE or IF. The biological data provided in Table 1 were determined as described herein, for example, in Example B1.

TABLE 1

Representative Compounds

| NO | NAME | STRUCTURE | Epic $K_d$ BRD4 1 | Epic $K_d$ BRD4 2 |
|----|------|-----------|-------------------|-------------------|
| 1 | N-cyclopentyl-7-(3,5-dimethylisoxazol-4-yl)quinoline-5-sulfonamide | 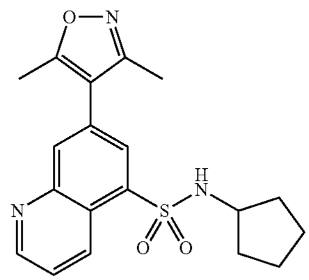 [SMILES: Cc1noc(C)c1-c1cc(S(=O)(=O)NC2CCCC2)c2cccnc2c1] | 2114 | 2485 |
| 2 | N-cyclopentyl-2-(difluoromethyl)-7-(3,5-dimethylisoxazol-4-yl)quinoline-5-sulfonamide | 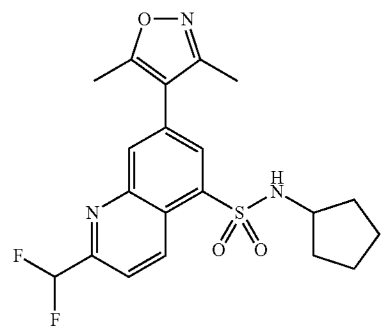 [SMILES: Cc1noc(C)c1-c1cc(S(=O)(=O)NC2CCCC2)c2ccc(C(F)F)nc2c1] | 3383 | 1321 |
| 3 | 2-chloro-N-cyclopentyl-7-(3,5-dimethylisoxazol-4-yl)quinoline-5-sulfonamide | 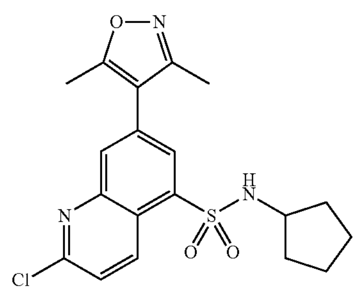 [SMILES: Cc1noc(C)c1-c1cc(S(=O)(=O)NC2CCCC2)c2ccc(Cl)nc2c1] | 1248 | 2967 |
| 4 | N-cyclopentyl-2-cyclopropyl-7-(3,5-dimethylisoxazol-4-yl)quinoline-5-sulfonamide | 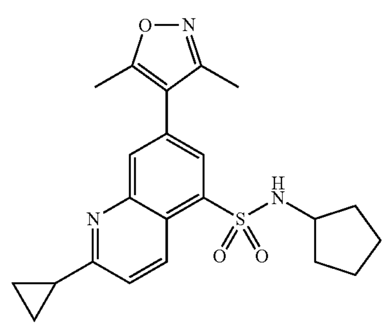 [SMILES: Cc1noc(C)c1-c1cc(S(=O)(=O)NC2CCCC2)c2ccc(C3CC3)nc2c1] | 1445 | 3495 |
| 5 | N-cyclopentyl-2-((cyclopropylmethyl)-amino)-7-(3,5-dimethylisoxazol-4-yl)quinoline-5-sulfonamide | 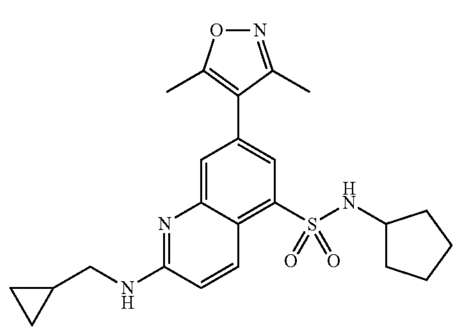 [SMILES: Cc1noc(C)c1-c1cc(S(=O)(=O)NC2CCCC2)c2ccc(NCC3CC3)nc2c1] | 1063 | 1464 |

TABLE 1-continued

Representative Compounds

| NO | NAME | STRUCTURE | Epic $K_d$ BRD4 1 | Epic $K_d$ BRD4 2 |
|---|---|---|---|---|
| 6 | N-cyclopentyl-2-(cyclopropylmethoxy)-7-(3,5-dimethylisoxazol-4-yl)quinoline-5-sulfonamide | 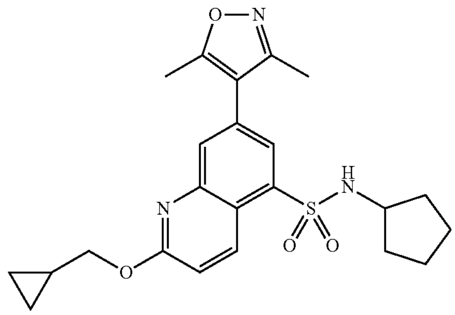 [SMILES: Cc1noc(C)c1-c1cc(S(=O)(=O)NC2CCCC2)c2ccc(OCC3CC3)nc2c1] | 2110 | 2041 |
| 7 | N-cyclopentyl-7-(3,5-dimethylisoxazol-4-yl)-2-oxo-1,2-dihydroquinoline-5-sulfonamide | 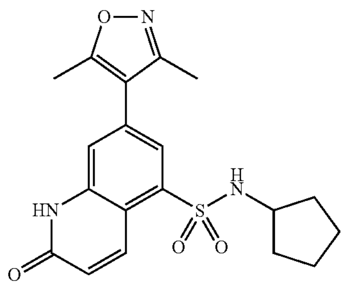 [SMILES: Cc1noc(C)c1-c1cc(S(=O)(=O)NC2CCCC2)c2ccc(=O)[nH]c2c1] | 1911 | 1128 |
| 8 | N-cyclopropyl-7-(3,5-dimethylisoxazol-4-yl)quinoline-5-sulfonamide | 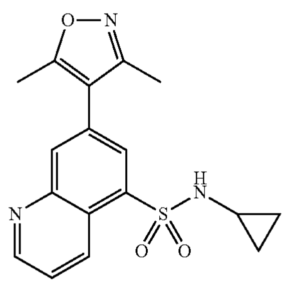 [SMILES: Cc1noc(C)c1-c1cc(S(=O)(=O)NC2CC2)c2cccnc2c1] | 3948 | 2248 |
| 9 | N-cyclopropyl-7-(3,5-dimethylisoxazol-4-yl)-N-methylquinoline-5-sulfonamide | 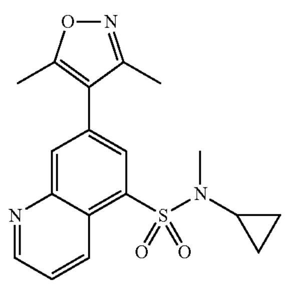 | >20000 | 12548 |
| 10 | N-cyclobutyl-7-(3,5-dimethylisoxazol-4-yl)quinoline-5-sulfonamide | 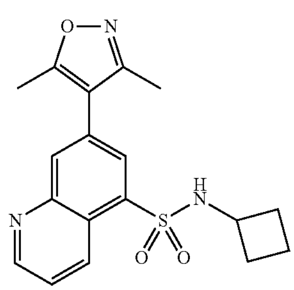 [SMILES: Cc1noc(C)c1-c1cc(S(=O)(=O)NC2CCC2)c2cccnc2c1] | 3193 | 2681 |

TABLE 1-continued

Representative Compounds

| NO | NAME | STRUCTURE | Epic $K_d$ BRD4 1 | Epic $K_d$ BRD4 2 |
|---|---|---|---|---|
| 11 | N-((3,3-difluorocyclobutyl)-methyl)-7-(3,5-dimethylisoxazol-4-yl)quinoline-5-sulfonamide | 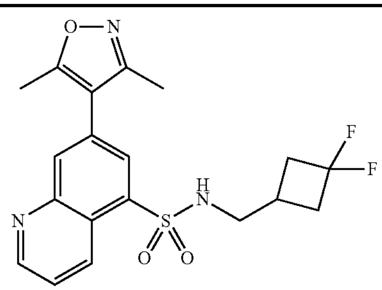 | 12778 | >20000 |
| 12 | 7-(3,5-dimethylisoxazol-4-yl)-N-((1R,2S)-2-phenylcyclopropyl)-quinoline-5-sulfonamide | 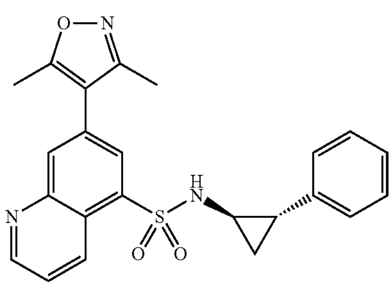 [SMILES: Cc1noc(C)c1-c1cc(S(=O)(=O)N[C@@H]2C[C@H]2c2ccccc2)c2cccnc2c1] | 15764 | >20000 |
| 13 | 7-(3,5-dimethylisoxazol-4-yl)-N-((1R,2R)-2-(4-fluorophenyl)cyclo-pentyl)quinoline-5-sulfonamide | 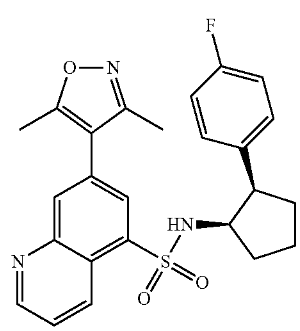 [SMILES: Cc1noc(C)c1-c1cc(S(=O)(=O)N[C@@H]2CCC[C@@H]2c2ccc(F)cc2)c2cccnc2c1] | 9998 | 12441 |
| 15 | N-(cyclopropylmethyl)-7-(3,5-dimethylisoxazol-4-yl)quinoline-5-sulfonamide | 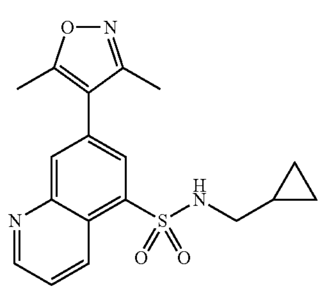 [SMILES: Cc1noc(C)c1-c1cc(S(=O)(=O)NCC2CC2)c2cccnc2c1] | 9426 | 5903 |
| 16 | N-cyclopentyl-7-(3,5-dimethylisoxazol-4-yl)-2-methoxyquinoline-5-sulfonamide | 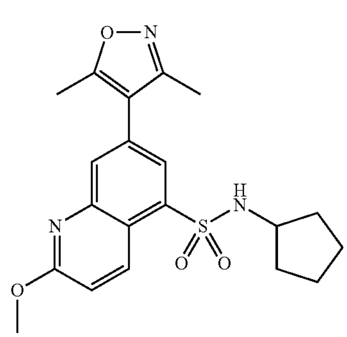 [SMILES: COc1ccc2c(S(=O)(=O)NC3CCCC3)cc(-c3c(C)noc3C)cc2n1] | 3367 | 6301 |

TABLE 1-continued

Representative Compounds

| NO | NAME | STRUCTURE | Epic K$_d$ BRD4 1 | Epic K$_d$ BRD4 2 |
|---|---|---|---|---|
| 17 | 2-amino-N-cyclopentyl-7-(3,5-dimethylisoxazol-4-yl)quinoline-5-sulfonamide | 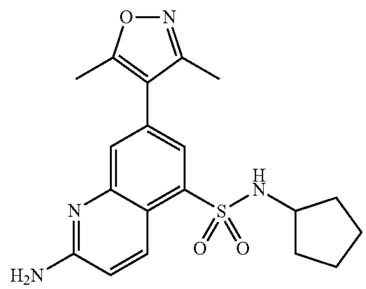 [SMILES: Cc1noc(C)c1-c1cc(S(=O)(=O)NC2CCCC2)c2ccc(N)nc2c1] | 885 | 1108 |
| 18 | 8-chloro-N-cyclopentyl-7-(3,5-dimethylisoxazol-4-yl)quinoline-5-sulfonamide | 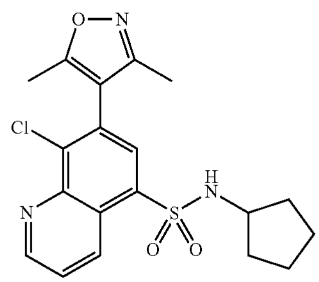 [SMILES: Cc1noc(C)c1-c1cc(S(=O)(=O)NC2CCCC2)c2cccnc2c1Cl] | 9147 | 4258 |
| 19 | 7-(3,5-dimethylisoxazol-4-yl)-N-((1S,3R)-3-hydroxycyclopentyl)-quinoline-5-sulfonamide | 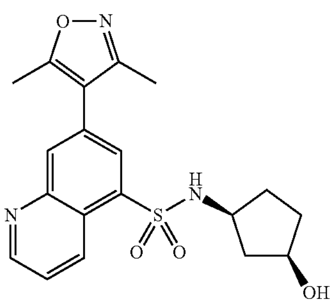 [SMILES: Cc1noc(C)c1-c1cc(S(=O)(=O)N[C@H]2CC[C@@H](O)C2)c2cccnc2c1] | 16616 | 7725 |
| 20 | 7-(3,5-dimethylisoxazol-4-yl)-N-((1R,3S)-3-hydroxycyclohexyl)-quinoline-5-sulfonamide | 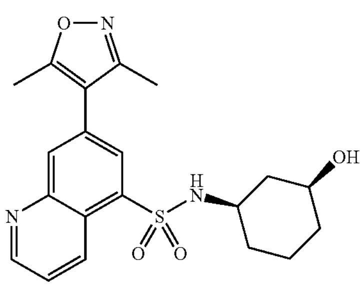 [SMILES: Cc1noc(C)c1-c1cc(S(=O)(=O)N[C@@H]2CCC[C@H](O)C2)c2cccnc2c1] | 5750 | 4786 |
| 21 | 7-(3,5-dimethylisoxazol-4-yl)-N-((1r,4r)-4-hydroxycyclohexyl)-quinoline-5-sulfonamide | 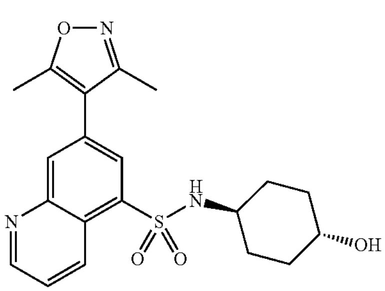 [SMILES: Cc1noc(C)c1-c1cc(S(=O)(=O)N[C@H]2CC[C@H](O)CC2)c2cccnc2c1] | 10353 | 17258 |

TABLE 1-continued

Representative Compounds

| NO | NAME | STRUCTURE | Epic $K_d$ BRD4 1 | Epic $K_d$ BRD4 2 |
|----|------|-----------|-------------------|-------------------|
| 22 | 3-bromo-N-cyclopentyl-7-(3,5-dimethylisoxazol-4-yl)-2-oxo-1,2-dihydroquinoline-5-sulfonamide | 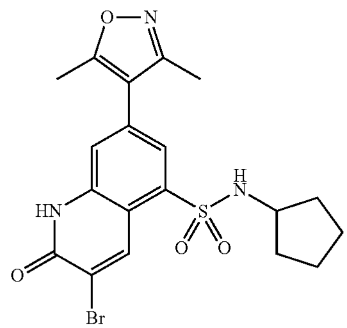 [SMILES: Cc1noc(C)c1-c1cc(S(=O)(=O)NC2CCCC2)c2cc(Br)c(=O)[nH]c2c1] | 1021 | 501 |
| 23 | 7-(3,5-dimethylisoxazol-4-yl)-N-((1R,2S)-2-hydroxycyclopentyl)-quinoline-5-sulfonamide | 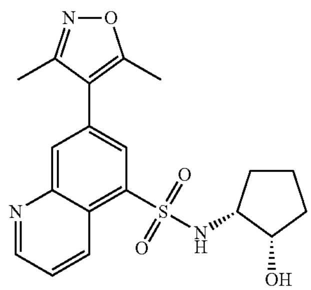 [SMILES: Cc1noc(C)c1-c1cc(S(=O)(=O)N[C@@H]2CCC[C@@H]2O)c2cccnc2c1] | 19541 | 16716 |
| 24 | 7-(3,5-dimethylisoxazol-4-yl)-N-(1-methylcyclopentyl)-quinoline-5-sulfonamide | 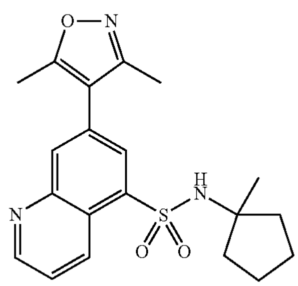 [SMILES: Cc1noc(C)c1-c1cc(S(=O)(=O)NC2(C)CCCC2)c2cccnc2c1] | 3547 | 2115 |
| 25 | tert-butyl ((1s,3s)-3-(7-(3,5-dimethylisoxazol-4-yl)quinoline-5-sulfonamido)cyclobutyl)carbamate | 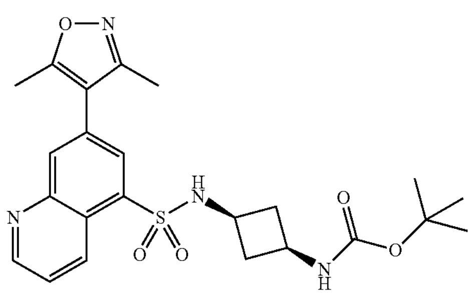 [SMILES: Cc1noc(C)c1-c1cc(S(=O)(=O)N[C@H]2C[C@@H](NC(=O)OC(C)(C)C)C2)c2cccnc2c1] | 16244 | >20000 |
| 26 | 7-(3,5-dimethylisoxazol-4-yl)-N-((1R,2R)-2-hydroxycyclopentyl)-quinoline-5-sulfonamide | 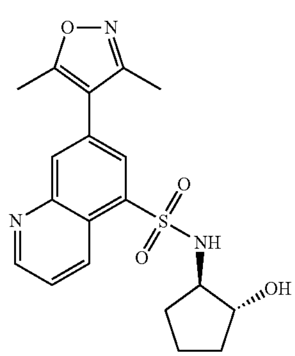 [SMILES: Cc1noc(C)c1-c1cc(S(=O)(=O)N[C@@H]2CCC[C@H]2O)c2cccnc2c1] | 4087 | 3549 |

TABLE 1-continued

Representative Compounds

| NO | NAME | STRUCTURE | Epic $K_d$ BRD4 1 | Epic $K_d$ BRD4 2 |
|----|------|-----------|-------------------|-------------------|
| 27 | 7-(3,5-dimethylisoxazol-4-yl)-N-((1S,2R)-2-hydroxycyclopentyl)-quinoline-5-sulfonamide | 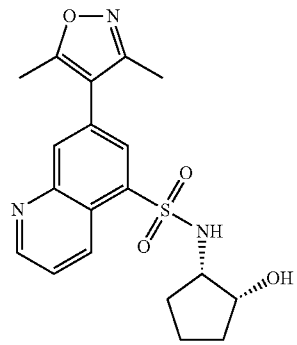 [SMILES: Cc1noc(C)c1-c1cc(S(=O)(=O)N[C@H]2CCC[C@H]2O)c2cccnc2c1] | 12461 | 6795 |
| 28 | N-cyclopentyl-7-(3,5-dimethylisoxazol-4-yl)-3-(4-fluorophenyl)-2-oxo-1,2-dihydroquinoline-5-sulfonamide | 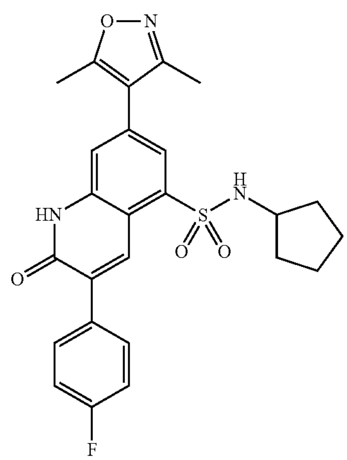 [SMILES: Cc1noc(C)c1-c1cc(S(=O)(=O)NC2CCCC2)c2cc(-c3ccc(F)cc3)c(=O)[nH]c2c1] | 348 | 555 |
| 29 | N-cyclopentyl-7-(3,5-dimethylisoxazol-4-yl)-2-oxo-3-(pyridin-3-yl)-1,2-dihydroquinoline-5-sulfonamide | 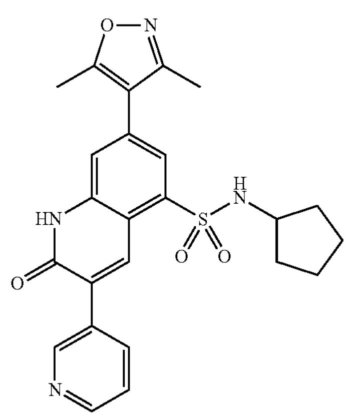 [SMILES: Cc1noc(C)c1-c1cc(S(=O)(=O)NC2CCCC2)c2cc(-c3cccnc3)c(=O)[nH]c2c1] | 253 | 241 |

TABLE 1-continued

Representative Compounds

| NO | NAME | STRUCTURE | Epic $K_d$ BRD4 1 | Epic $K_d$ BRD4 2 |
|---|---|---|---|---|
| 30 | N-cyclopentyl-3-(1,2-dimethyl-1H-imidazol-5-yl)-7-(3,5-dimethylisoxazol-4-yl)-2-oxo-1,2-dihydroquinoline-5-sulfonamide | 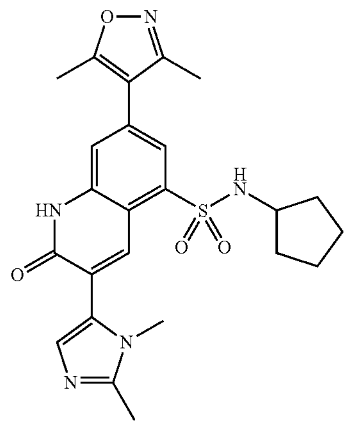 [SMILES: Cc1noc(C)c1-c1cc(S(=O)(=O)NC2CCCC2)c2cc(-c3cnc(C)n3C)c(=O)[nH]c2c1] | 6399 | 1704 |
| 31 | 3-cyano-N-cyclopentyl-7-(3,5-dimethylisoxazol-4-yl)-2-oxo-1,2-dihydroquinoline-5-sulfonamide | 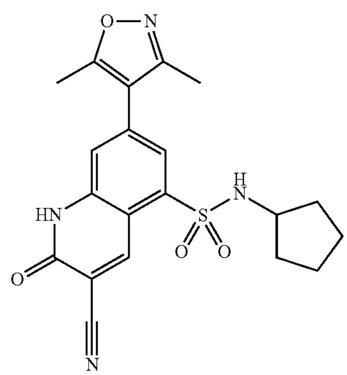 [SMILES: Cc1noc(C)c1-c1cc(S(=O)(=O)NC2CCCC2)c2cc(C#N)c(=O)[nH]c2c1] | 867 | 634 |
| 32 | N-cyclopentyl-7-(3,5-dimethylisoxazol-4-yl)-3-(1H-imidazol-1-yl)-2-oxo-1,2-dihydroquinoline-5-sulfonamide | 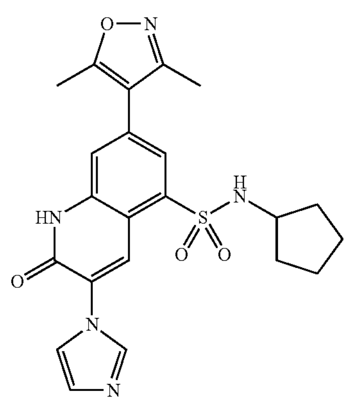 [SMILES: Cc1noc(C)c1-c1cc(S(=O)(=O)NC2CCCC2)c2cc(-n3ccnc3)c(=O)[nH]c2c1] | 717 | 519 |

TABLE 1-continued

Representative Compounds

| NO | NAME | STRUCTURE | Epic $K_d$ BRD4 1 | Epic $K_d$ BRD4 2 |
|----|------|-----------|-------------------|-------------------|
| 33 | N-cyclopentyl-7-(3,5-dimethylisoxazol-4-yl)-2-oxo-3-(1H-pyrazol-1-yl)-1,2-dihydroquinoline-5-sulfonamide | 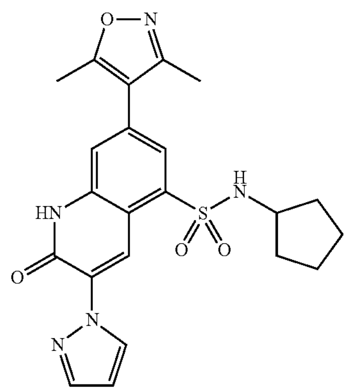 [SMILES: Cc1noc(C)c1-c1cc(S(=O)(=O)NC2CCCC2)c2cc(-n3cccn3)c(=O)[nH]c2c1] | 760 | 561 |
| 34 | N-((1S,3S)-3-aminocyclobutyl)-7-(3,5-dimethylisoxazol-4-yl)quinoline-5-sulfonamide | 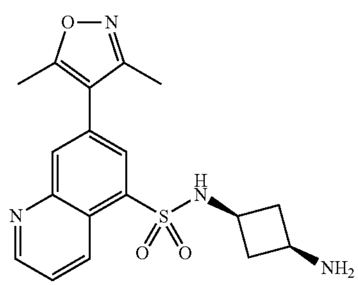 [SMILES: Cc1noc(C)c1-c1cc(S(=O)(=O)N[C@H]2C[C@@H](N)C2)c2cccnc2c1] | 5475 | 11124 |
| 35 | (1R,2R)-N-cyclopentyl-2-(7-(3,5-dimethylisoxazol-4-yl)quinoline-5-sulfonamido)cyclopentanecarboxamide | 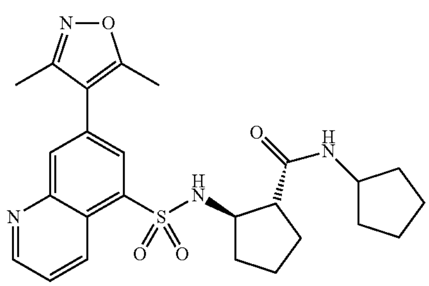 | >20000 | 19673 |
| 36 | N-cyclopentyl-7-(3,5-dimethylisoxazol-4-yl)-2-oxo-3-(pyridin-2-yl)-1,2-dihydroquinoline-5-sulfonamide | 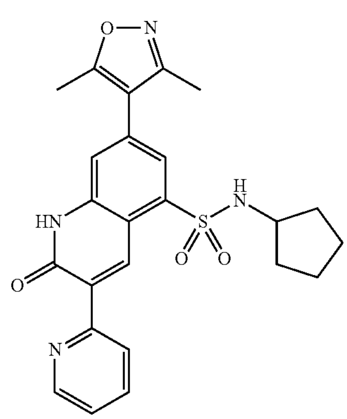 [SMILES: Cc1noc(C)c1-c1cc(S(=O)(=O)NC2CCCC2)c2cc(-c3ccccn3)c(=O)[nH]c2c1] | 1452 | 718 |

TABLE 1-continued

Representative Compounds

| NO | NAME | STRUCTURE | Epic $K_d$ BRD4 1 | Epic $K_d$ BRD4 2 |
|---|---|---|---|---|
| 37 | N-cyclopentyl-7-(3,5-dimethylisoxazol-4-yl)-2-oxo-3-(pyrimidin-2-yl)-1,2-dihydroquinoline-5-sulfonamide | 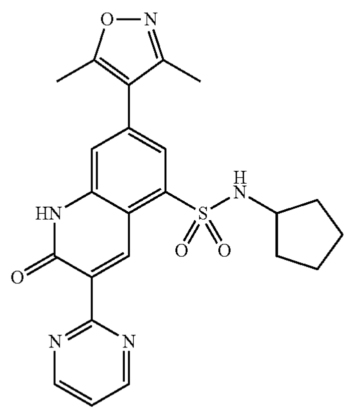 [SMILES: Cc1noc(C)c1-c1cc(S(=O)(=O)NC2CCCC2)c2cc(-c3ncccn3)c(=O)[nH]c2c1] | 2087 | 757 |
| 38 | N-((1S,2S,4R)-bicyclo[2.2.1]heptan-2-yl)-7-(3,5-dimethylisoxazol-4-yl)quinoline-5-sulfonamide | 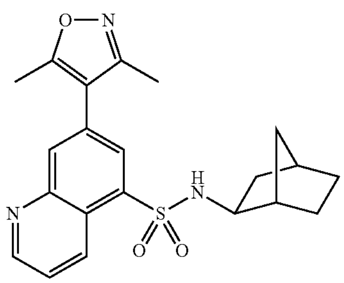 [SMILES: Cc1noc(C)c1-c1cc(S(=O)(=O)NC2CC3CCC2C3)c2cccnc2c1] | 3144 | 3485 |
| 39 | N-(3,3-dimethylcyclopentyl)-7-(3,5-dimethylisoxazol-4-yl)quinoline-5-sulfonamide | 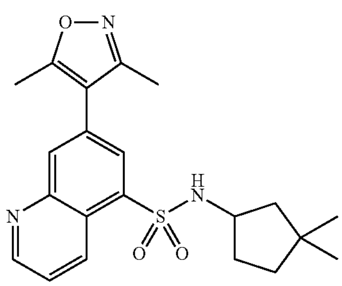 [SMILES: Cc1noc(C)c1-c1cc(S(=O)(=O)NC2CCC(C)(C)C2)c2cccnc2c1] | 5558 | 13420 |
| 40 | 7-(3,5-dimethylisoxazol-4-yl)-N-(8-methyl-8-azabicyclo[3.2.1]octan-3-yl)quinoline-5-sulfonamide | 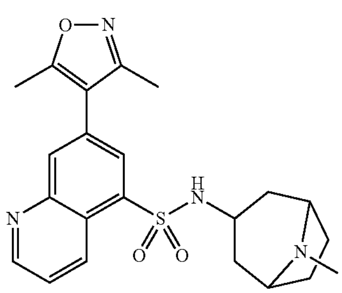 [SMILES: Cc1noc(C)c1-c1cc(S(=O)(=O)NC2CC3CCC(C2)N3C)c2cccnc2c1] | 15977 | >20000 |

TABLE 1-continued

Representative Compounds

| NO | NAME | STRUCTURE | Epic $K_d$ BRD4 1 | Epic $K_d$ BRD4 2 |
|---|---|---|---|---|
| 41 | 3-amino-N-cyclopentyl-7-(3,5-dimethylisoxazol-4-yl)-2-oxo-1,2-dihydroquinoline-5-sulfonamide | 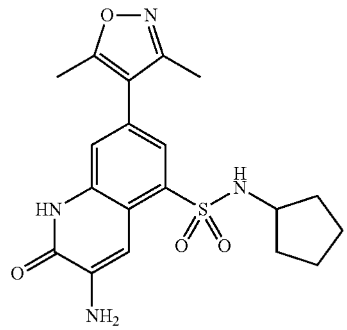 [SMILES: Cc1noc(C)c1-c1cc(S(=O)(=O)NC2CCCC2)c2cc(N)c(=O)[nH]c2c1] | 400 | 450 |
| 42 | (1R,2R)-2-(7-(3,5-dimethylisoxazol-4-yl)quinoline-5-sulfonamido)-N-((1-methyl-1H-imidazol-2-yl)methyl)cyclopentanecarboxamide | 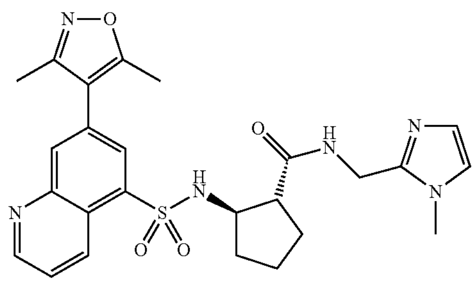 | 16176 | 6838 |
| 43 | (1S,2R)-2-(7-(3,5-dimethylisoxazol-4-yl)quinoline-5-sulfonamido)-N-((1-methyl-1H-imidazol-2-yl)methyl)cyclopentanecarboxamide | 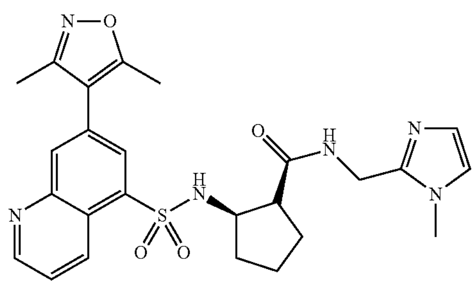 | >20000 | 10663 |
| 44 | N-cyclopentyl-7-(3,5-dimethylisoxazol-4-yl)-2-(piperazin-1-yl)quinoline-5-sulfonamide | 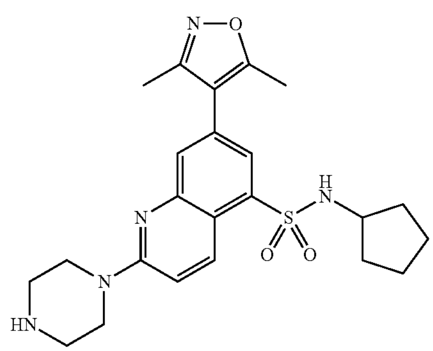 [SMILES: Cc1noc(C)c1-c1cc(S(=O)(=O)NC2CCCC2)c2ccc(N3CCNCC3)nc2c1] | 799 | 504 |
| 45 | tert-butyl ((1R,2R)-2-(7-(3,5-dimethylisoxazol-4-yl)quinoline-5-sulfonamido)cyclopentyl)carbamate | 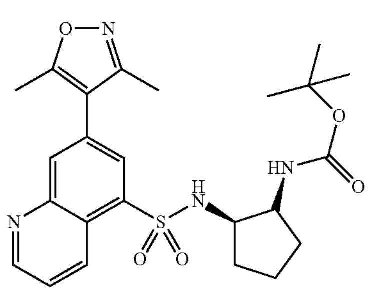 | 14595 | >20000 |

TABLE 1-continued

Representative Compounds

| NO | NAME | STRUCTURE | Epic $K_d$ BRD4 1 | Epic $K_d$ BRD4 2 |
|---|---|---|---|---|
| 46 | N-((1R,2R)-2-aminocyclopentyl)-7-(3,5-dimethylisoxazol-4-yl)quinoline-5-sulfonamide | 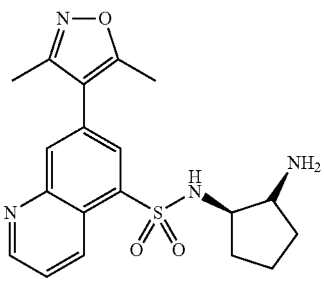 | 6424 | 7831 |
| 47 | 7-(3,5-dimethylisoxazol-4-yl)-N-((1R,2R)-2-(piperazine-1-carbonyl)cyclopentyl)quinoline-5-sulfonamide | 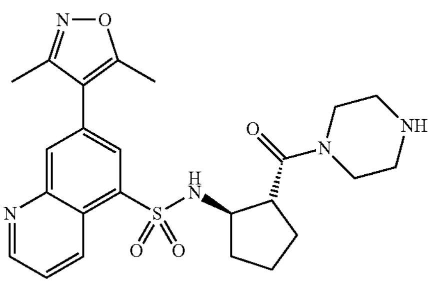 | 3162 | 2269 |
| 48 | 7-(3,5-dimethylisoxazol-4-yl)-2-oxo-N-phenethyl-1,2-dihydroquinoline-5-sulfonamide | 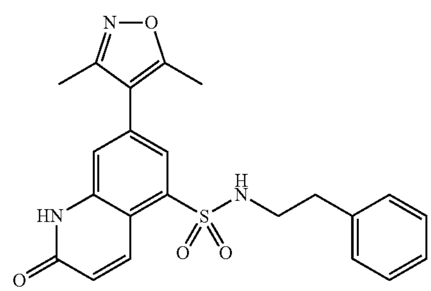 [SMILES: Cc1noc(C)c1-c1cc(S(=O)(=O)NCCc2ccccc2)c2ccc(=O)[nH]c2c1] | >20000 | 19974 |
| 49 | N-(1-cyanocyclopropyl)-7-(3,5-dimethylisoxazol-4-yl)quinoline-5-sulfonamide | 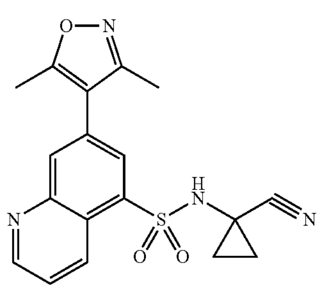 [SMILES: Cc1noc(C)c1-c1cc(S(=O)(=O)NC2(C#N)CC2)c2cccnc2c1] | >20000 | 18794 |
| 50 | 7-(3,5-dimethylisoxazol-4-yl)-N-((1R,2S)-2-(piperazine-1-carbonyl)cyclopentyl)quinoline-5-sulfonamide | 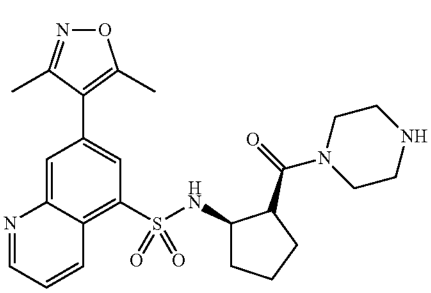 | 7169 | 8127 |

TABLE 1-continued

Representative Compounds

| NO | NAME | STRUCTURE | Epic K$_d$ BRD4 1 | Epic K$_d$ BRD4 2 |
|---|---|---|---|---|
| 51 | N-((1S,2R)-2-(7-(3,5-dimethylisoxazol-4-yl)quinoline-5-sulfonamido)cyclopentyl)acetamide | 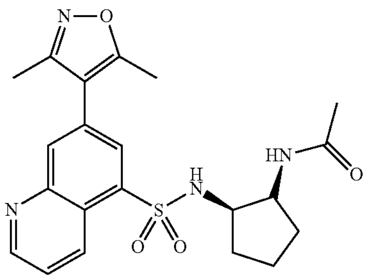 | 7621 | 6446 |
| 52 | N-(1-cyanocyclopentyl)-7-(3,5-dimethylisoxazol-4-yl)quinoline-5-sulfonamide | 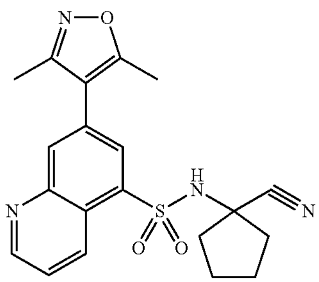 [SMILES: Cc1noc(C)c1-c1cc(S(=O)(=O)NC2(C#N)CCCC2)c2cccnc2c1] | >20000 | 11718 |
| 53 | 7-(3,5-dimethylisoxazol-4-yl)-N-((1R,2S)-2-(ethylamino)cyclopentyl)quinoline-5-sulfonamide | 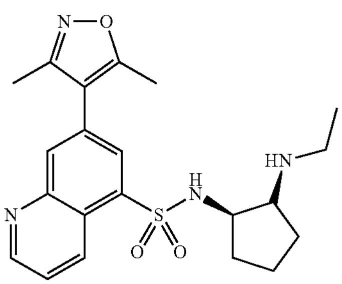 | >20000 | 8641 |
| 54 | ethyl ((1S,2R)-2-(7-(3,5-dimethylisoxazol-4-yl)quinoline-5-sulfonamido)cyclopentyl)carbamate | 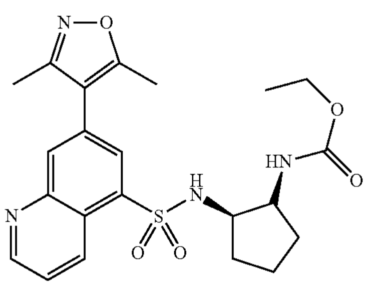 | 5865 | 7988 |
| 55 | N-cyclopentyl-7-(3,5-dimethylisoxazol-4-yl)-3-morpholino-2-oxo-1,2-dihydroquinoline-5-sulfonamide | 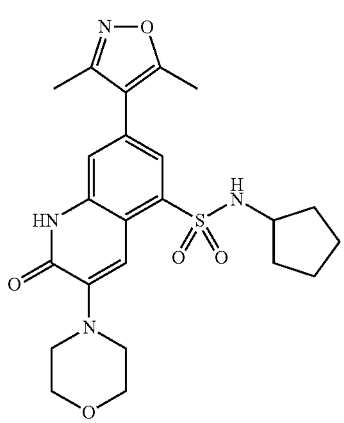 [SMILES: Cc1noc(C)c1-c1cc(S(=O)(=O)NC2CCCC2)c2cc(N3CCOCC3)c(=O)[nH]c2c1] | 1336 | 726 |

TABLE 1-continued

Representative Compounds

| NO | NAME | STRUCTURE | Epic $K_d$ BRD4 1 | Epic $K_d$ BRD4 2 |
|---|---|---|---|---|
| 56 | N-cyclopentyl-7-(3,5-dimethylisoxazol-4-yl)-2-oxo-3-(piperazin-1-yl)-1,2-dihydroquinoline-5-sulfonamide | 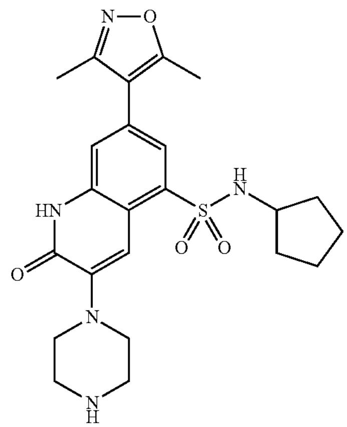 [SMILES: Cc1noc(C)c1-c1cc(S(=O)(=O)NC2CCCC2)c2cc(N3CCNCC3)c(=O)[nH]c2c1] | 933 | 611 |
| 57 | N-cyclopentyl-7-(3,5-dimethylisoxazol-4-yl)-3-((2-hydroxyethyl)amino)-2-oxo-1,2-dihydroquinoline-5-sulfonamide | 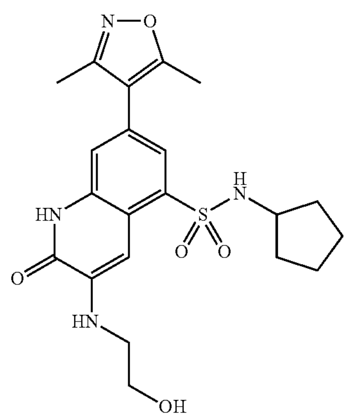 [SMILES: Cc1noc(C)c1-c1cc(S(=O)(=O)NC2CCCC2)c2cc(NCCO)c(=O)[nH]c2c1] | 444 | 477 |
| 58 | N-cyclopentyl-7-(3,5-dimethylisoxazol-4-yl)-3-((2-methoxyethyl)amino)-2-oxo-1,2-dihydroquinoline-5-sulfonamide | 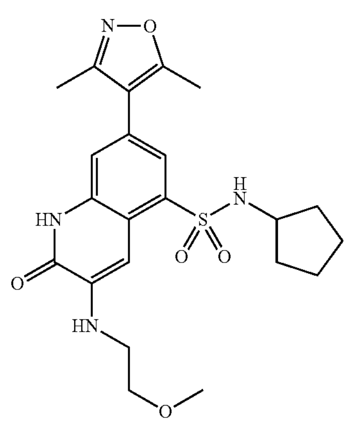 [SMILES: COCCNc1cc2c(S(=O)(=O)NC3CCCC3)cc(-c3c(C)noc3C)cc2[nH]c1=O] | 313 | 320 |

TABLE 1-continued

Representative Compounds

| NO | NAME | STRUCTURE | Epic $K_d$ BRD4 1 | Epic $K_d$ BRD4 2 |
|---|---|---|---|---|
| 59 | N-cyclopentyl-7-(3,5-dimethylisoxazol-4-yl)-2-oxo-3-(pyrrolidin-1-yl)-1,2-dihydroquinoline-5-sulfonamide | 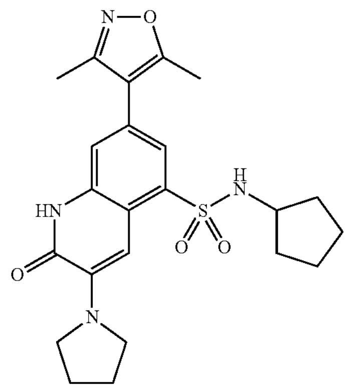 [SMILES: Cc1noc(C)c1-c1cc(S(=O)(=O)NC2CCCC2)c2cc(N3CCCC3)c(=O)[nH]c2c1] | 897 | 866 |
| 60 | N-cyclopentyl-7-(3,5-dimethylisoxazol-4-yl)-2-oxo-3-(piperidin-1-yl)-1,2-dihydroquinoline-5-sulfonamide | 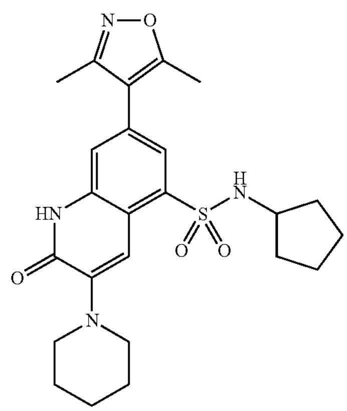 [SMILES: Cc1noc(C)c1-c1cc(S(=O)(=O)NC2CCCC2)c2cc(N3CCCCC3)c(=O)[nH]c2c1] | 2231 | 1898 |
| 61 | N-cyclopentyl-3-(dimethylamino)-7-(3,5-dimethylisoxazol-4-yl)-2-oxo-1,2-dihydroquinoline-5-sulfonamide | 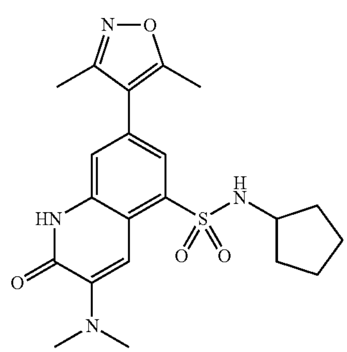 [SMILES: Cc1noc(C)c1-c1cc(S(=O)(=O)NC2CCCC2)c2cc(N(C)C)c(=O)[nH]c2c1] | 1021 | 645 |
| 62 | N-cyclopentyl-7-(3,5-dimethylisoxazol-4-yl)-3-(methylamino)-2-oxo-1,2-dihydroquinoline-5-sulfonamide | 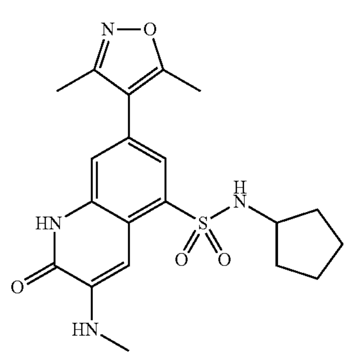 [SMILES: CNc1cc2c(S(=O)(=O)NC3CCCC3)cc(-c3c(C)noc3C)cc2[nH]c1=O] | 850 | 526 |

TABLE 1-continued

Representative Compounds

| NO | NAME | STRUCTURE | Epic $K_d$ BRD4 1 | Epic $K_d$ BRD4 2 |
|---|---|---|---|---|
| 63 | 7-(3,5-dimethylisoxazol-4-yl)-N-((1R,2S)-2-(methoxymethyl)cyclopentyl)quinoline-5-sulfonamide | 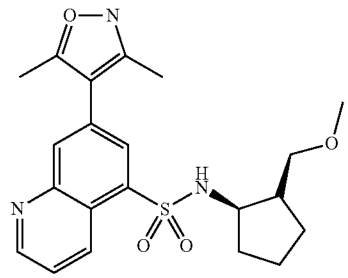 | 14636 | 9564 |
| 64 | N-cyclopentyl-7-(3,5-dimethylisoxazol-4-yl)-2-oxo-3-(2-oxooxazolidin-3-yl)-1,2-dihydroquinoline-5-sulfonamide | 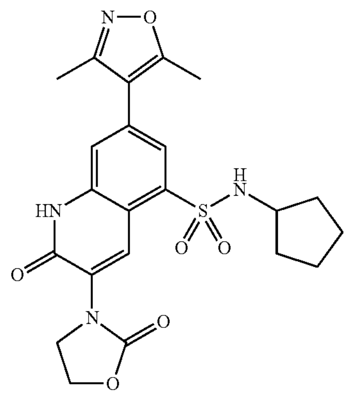 [SMILES: Cc1noc(C)c1-c1cc(S(=O)(=O)NC2CCCC2)c2cc(N3CCOC3=O)c(=O)[nH]c2c1] | 4851 | 3205 |
| 65 | N-cyclopentyl-7-(3,5-dimethylisoxazol-4-yl)-3-(4-methylpiperazin-1-yl)-2-oxo-1,2-dihydroquinoline-5-sulfonamide | 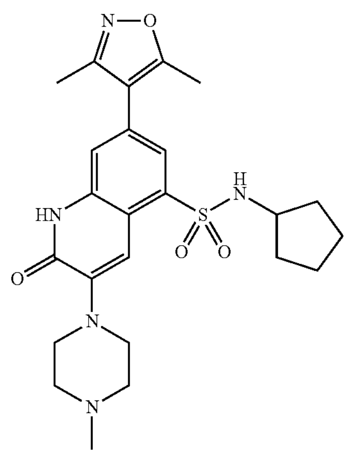 [SMILES: Cc1noc(C)c1-c1cc(S(=O)(=O)NC2CCCC2)c2cc(N3CCN(C)CC3)c(=O)[nH]c2c1] | 981 | 546 |
| 66 | N-cyclopentyl-7-(3,5-dimethylisoxazol-4-yl)-3-((1-methylpiperidin-4-yl)amino)-2-oxo-1,2-dihydroquinoline-5-sulfonamide | 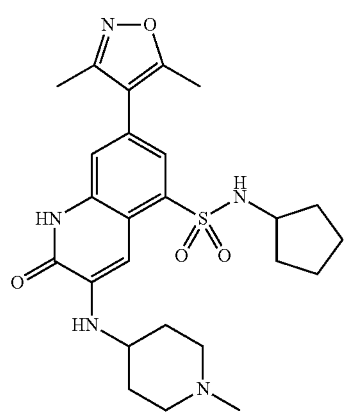 [SMILES: Cc1noc(C)c1-c1cc(S(=O)(=O)NC2CCCC2)c2cc(NC3CCN(C)CC3)c(=O)[nH]c2c1] | 520 | 421 |

TABLE 1-continued

Representative Compounds

| NO | NAME | STRUCTURE | Epic $K_d$ BRD4 1 | Epic $K_d$ BRD4 2 |
|---|---|---|---|---|
| 67 | N-cyclopentyl-7-(3,5-dimethylisoxazol-4-yl)-2-oxo-3-((pyridin-3-ylmethyl)amino)-1,2-dihydroquinoline-5-sulfonamide | 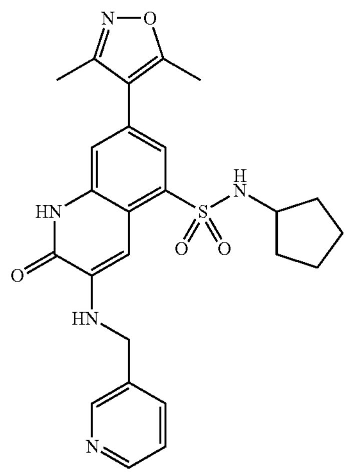 [SMILES: Cc1noc(C)c1-c1cc(S(=O)(=O)NC2CCCC2)c2cc(NCc3cccnc3)c(=O)[nH]c2c1] | 444 | 404 |
| 68 | N-cyclopropyl-7-(3,5-dimethylisoxazol-4-yl)-2-oxo-1,2-dihydroquinoline-5-sulfonamide | 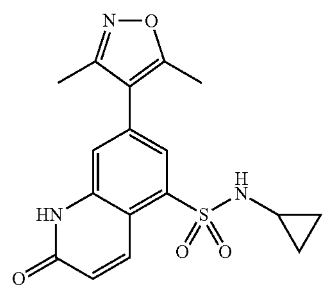 [SMILES: Cc1noc(C)c1-c1cc(S(=O)(=O)NC2CC2)c2ccc(=O)[nH]c2c1] | 13811 | 2917 |
| 69 | 5-(N-cyclopentylsulfamoyl)-7-(3,5-dimethylisoxazol-4-yl)-2-oxo-1,2-dihydroquinoline-3-carboxamide | 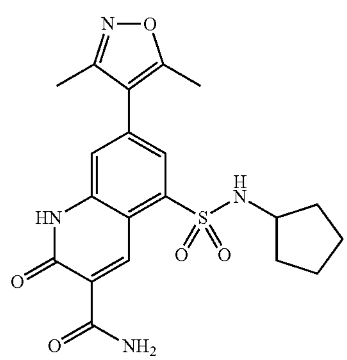 [SMILES: Cc1noc(C)c1-c1cc(S(=O)(=O)NC2CCCC2)c2cc(C(N)=O)c(=O)[nH]c2c1] | 7267 | 1185 |
| 70 | 5-(N-cyclopentylsulfamoyl)-7-(3,5-dimethylisoxazol-4-yl)-2-oxo-1,2-dihydroquinoline-3-carboxylic acid | 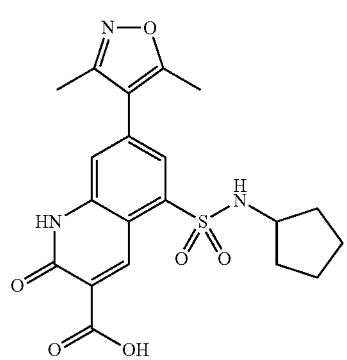 [SMILES: Cc1noc(C)c1-c1cc(S(=O)(=O)NC2CCCC2)c2cc(C(=O)O)c(=O)[nH]c2c1] | 8234 | 1956 |

TABLE 1-continued

Representative Compounds

| NO | NAME | STRUCTURE | Epic $K_d$ BRD4 1 | Epic $K_d$ BRD4 2 |
|---|---|---|---|---|
| 71 | 7-(3,5-dimethylisoxazol-4-yl)-N-((1R,2R)-2-(4-methylpiperazine-1-carbonyl)cyclopentyl)quinoline-5-sulfonamide | 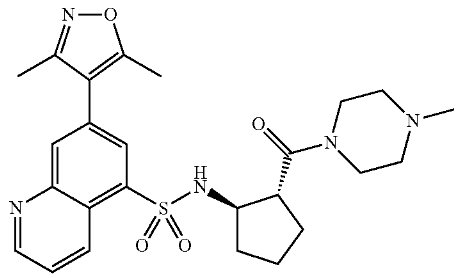 [SMILES: Cc1noc(C)c1-c1cc(S(=O)(=O)N[C@@H]2CCC[C@H]2C(=O)N2CCN(C)CC2)c2cccnc2c1] | 4894 | 4149 |
| 72 | (1R,2R)-N-(2-aminoethyl)-2-(7-(3,5-dimethylisoxazol-4-yl)quinoline-5-sulfonamido)cyclopentanecarboxamide | 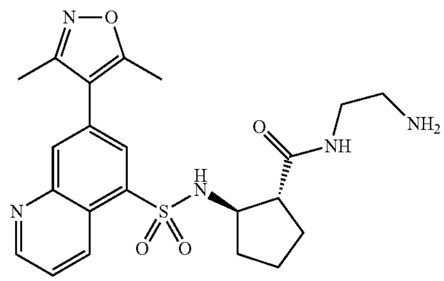 [SMILES: Cc1noc(C)c1-c1cc(S(=O)(=O)N[C@@H]2CCC[C@H]2C(=O)NCCN)c2cccnc2c1] | 1438 | 2327 |
| 73 | (1R,2R)-N-(2-acetamidoethyl)-2-(7-(3,5-dimethylisoxazol-4-yl)quinoline-5-sulfonamido)cyclopentanecarboxamide | 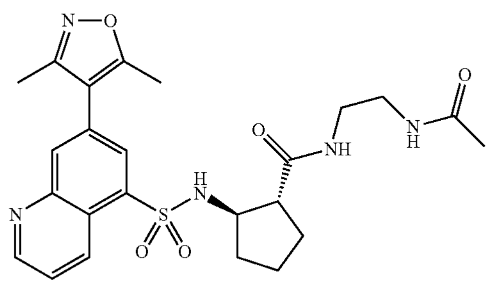 [SMILES: CC(=O)NCCNC(=O)[C@@H]1CCC[C@H]1NS(=O)(=O)c1cc(-c2c(C)noc2C)cc2ncccc12] | >20000 | 16727 |
| 74 | N-(2-aminoethyl)-7-(3,5-dimethylisoxazol-4-yl)quinoline-5-sulfonamide | 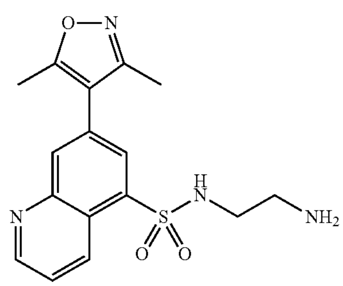 [SMILES: Cc1noc(C)c1-c1cc(S(=O)(=O)NCCN)c2cccnc2c1] | 14100 | 17456 |
| 75 | 5-(N-cyclopentylsulfamoyl)-7-(3,5-dimethylisoxazol-4-yl)-N,N-dimethyl-2-oxo-1,2-dihydroquinoline-3-carboxamide | 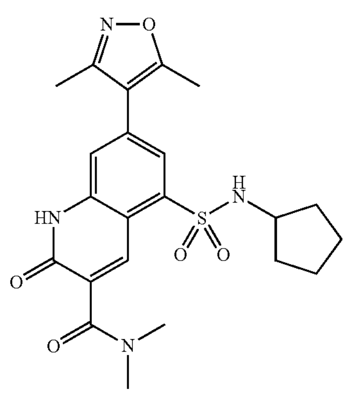 [SMILES: Cc1noc(C)c1-c1cc(S(=O)(=O)NC2CCCC2)c2cc(C(=O)N(C)C)c(=O)[nH]c2c1] | 10744 | 8940 |

TABLE 1-continued

Representative Compounds

| NO | NAME | STRUCTURE | Epic K$_d$ BRD4 1 | Epic K$_d$ BRD4 2 |
|---|---|---|---|---|
| 76 | N-cyclopentyl-3-((cyclopropylmethyl)-amino)-7-(3,5-dimethylisoxazol-4-yl)-2-oxo-1,2-dihydroquinoline-5-sulfonamide | 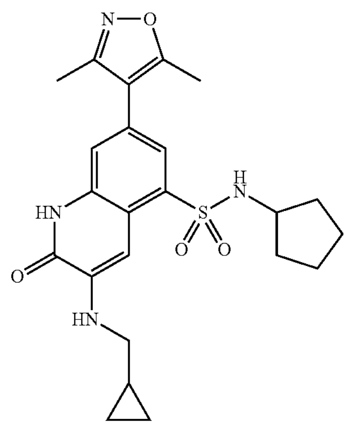 [SMILES: Cc1noc(C)c1-c1cc(S(=O)(=O)NC2CCCC2)c2cc(NCC3CC3)c(=O)[nH]c2c1] | 416 | 497 |
| 77 | N-cyclopentyl-7-(3,5-dimethylisoxazol-4-yl)-3-(isopropylamino)-2-oxo-1,2-dihydroquinoline-5-sulfonamide | 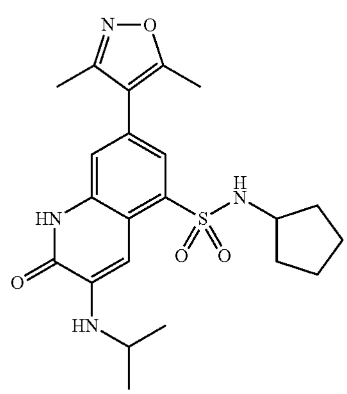 [SMILES: Cc1noc(C)c1-c1cc(S(=O)(=O)NC2CCCC2)c2cc(NC(C)C)c(=O)[nH]c2c1] | 896 | 610 |
| 78 | 3-((2-aminoethyl)amino)-N-cyclopentyl-7-(3,5-dimethylisoxazol-4-yl)-2-oxo-1,2-dihydroquinoline-5-sulfonamide | 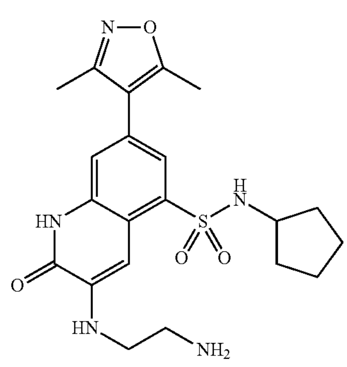 [SMILES: Cc1noc(C)c1-c1cc(S(=O)(=O)NC2CCCC2)c2cc(NCCN)c(=O)[nH]c2c1] | 744 | 392 |

TABLE 1-continued

Representative Compounds

| NO | NAME | STRUCTURE | Epic $K_d$ BRD4 1 | Epic $K_d$ BRD4 2 |
|---|---|---|---|---|
| 79 | N-cyclopentyl-3-((2,2-difluoroethyl)amino)-7-(3,5-dimethylisoxazol-4-yl)-2-oxo-1,2-dihydroquinoline-5-sulfonamide | 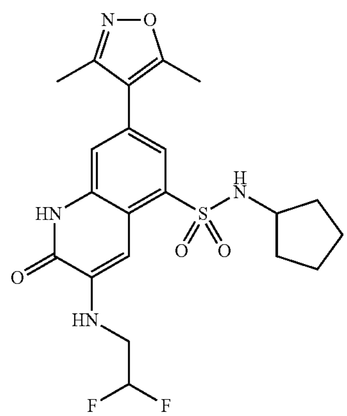 [SMILES: Cc1noc(C)c1-c1cc(S(=O)(=O)NC2CCCC2)c2cc(NCC(F)F)c(=O)[nH]c2c1] | 1348 | 607 |
| 80 | N-cyclopropyl-7-(3,5-dimethylisoxazol-4-yl)-2-(piperazin-1-yl)quinoline-5-sulfonamide | 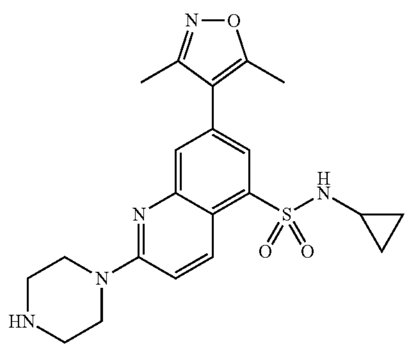 [SMILES: Cc1noc(C)c1-c1cc(S(=O)(=O)NC2CC2)c2ccc(N3CCNCC3)nc2c1] | 1734 | 1386 |
| 81 | (S)-N-(4,4-dimethyl-1-oxo-1-(piperazin-1-yl)pentan-2-yl)-7-(3,5-dimethylisoxazol-4-yl)quinoline-5-sulfonamide | 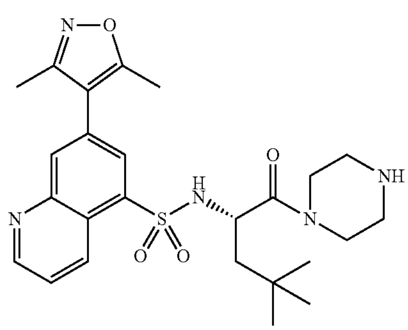 [SMILES: Cc1noc(C)c1-c1cc(S(=O)(=O)N[C@@H](CC(C)(C)C)C(=O)N2CCNCC2)c2cccnc2c1] | 13707 | >20000 |
| 82 | 7-(3,5-dimethylisoxazol-4-yl)-N-((1R,2R)-2-hydroxycyclopentyl)-2-oxo-1,2-dihydroquinoline-5-sulfonamide | 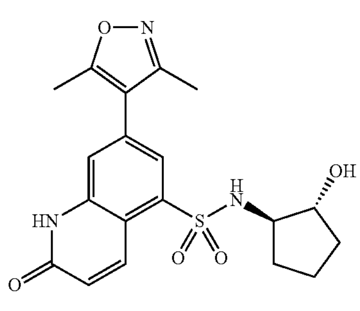 [SMILES: Cc1noc(C)c1-c1cc(S(=O)(=O)N[C@@H]2CCC[C@H]2O)c2ccc(=O)[nH]c2c1] | 1920 | 1901 |

TABLE 1-continued

Representative Compounds

| NO | NAME | STRUCTURE | Epic $K_d$ BRD4 1 | Epic $K_d$ BRD4 2 |
|---|---|---|---|---|
| 83 | N-(2,2-dimethylcyclopropyl)-7-(3,5-dimethylisoxazol-4-yl)quinoline-5-sulfonamide | 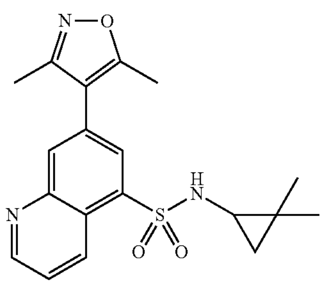 [SMILES: Cc1noc(C)c1-c1cc(S(=O)(=O)NC2CC2(C)C)c2cccnc2c1] | 16706 | 16576 |
| 84 | 7-(3,5-dimethylisoxazol-4-yl)-N-(1-(trifluoromethyl)cyclopropyl)quinoline-5-sulfonamide | 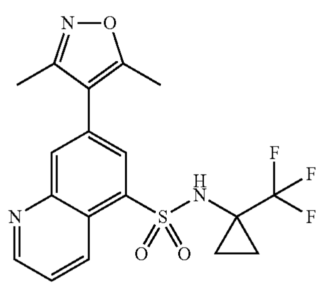 [SMILES: Cc1noc(C)c1-c1cc(S(=O)(=O)NC2(C(F)(F)F)CC2)c2cccnc2c1] | 2000 | 18196 |
| 85 | 7-(3,5-dimethylisoxazol-4-yl)-N-((1R,2R)-2-hydroxycyclopentyl)-3-((2-methoxyethyl)amino)-2-oxo-1,2-dihydroquinoline-5-sulfonamide | 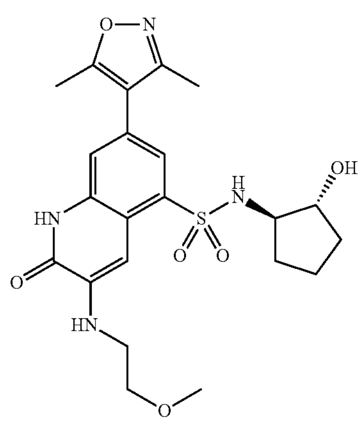 [SMILES: COCCNc1cc2c(S(=O)(=O)N[C@@H]3CCC[C@H]3O)cc(-c3c(C)noc3C)cc2[nH]c1=O] | 483 | 429 |
| 86 | N-cyclopentyl-7-(3,5-dimethylisoxazol-4-yl)quinoxaline-5-sulfonamide | 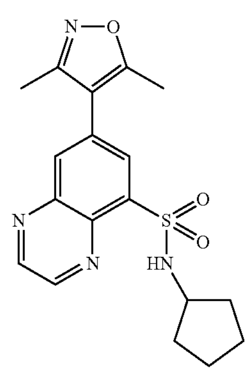 [SMILES: Cc1noc(C)c1-c1cc(S(=O)(=O)NC2CCCC2)c2nccnc2c1] | 3475 | 2457 |

TABLE 1-continued

Representative Compounds

| NO | NAME | STRUCTURE | Epic $K_d$ BRD4 1 | Epic $K_d$ BRD4 2 |
|---|---|---|---|---|
| 87 | N-cyclopentyl-7-(3,5-dimethylisoxazol-4-yl)-2-oxo-1,2-dihydroquinoxaline-5-sulfonamide | 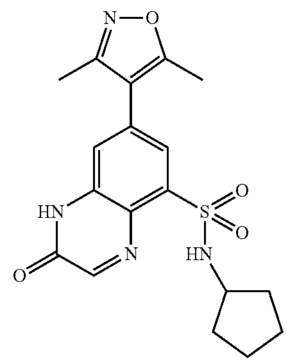 [SMILES: Cc1noc(C)c1-c1cc(S(=O)(=O)NC2CCCC2)c2ncc(=O)[nH]c2c1] | 2196 | 1345 |
| 88 | N-cyclopentyl-3-((2-(dimethylamino)ethyl)amino)-7-(3,5-dimethylisoxazol-4-yl)-2-oxo-1,2-dihydroquinoline-5-sulfonamide | 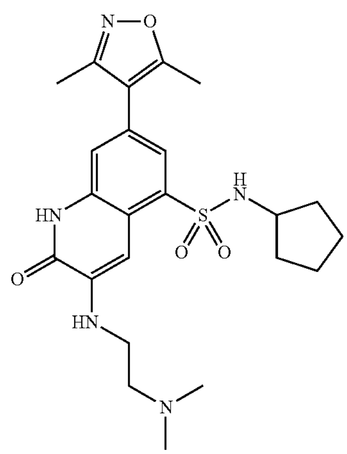 [SMILES: Cc1noc(C)c1-c1cc(S(=O)(=O)NC2CCCC2)c2cc(NCCN(C)C)c(=O)[nH]c2c1] | 1061 | 943 |
| 89 | N-cyclopentyl-7-(3,5-dimethylisoxazol-4-yl)-2-oxo-3-((2-(pyrrolidin-1-yl)ethyl)amino)-1,2-dihydroquinoline-5-sulfonamide | 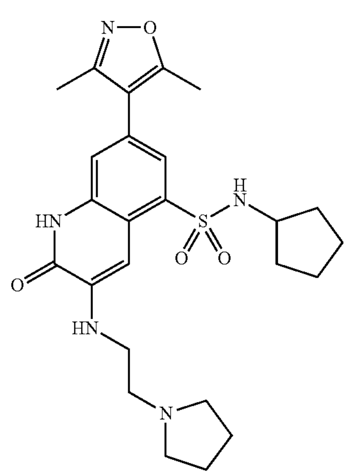 [SMILES: Cc1noc(C)c1-c1cc(S(=O)(=O)NC2CCCC2)c2cc(NCCN3CCCC3)c(=O)[nH]c2c1] | 881 | 656 |

TABLE 1-continued

Representative Compounds

| NO | NAME | STRUCTURE | Epic K$_d$ BRD4 1 | Epic K$_d$ BRD4 2 |
|---|---|---|---|---|
| 90 | N-cyclopentyl-7-(3,5-dimethylisoxazol-4-yl)-3-((2-morpholinoethyl)amino)-2-oxo-1,2-dihydroquinoline-5-sulfonamide | 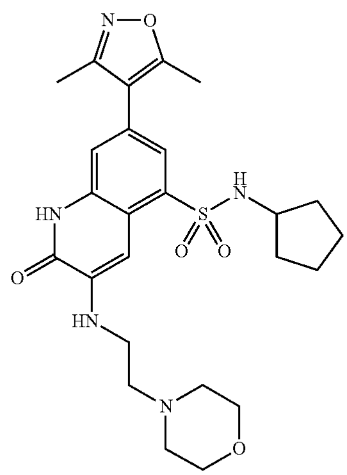 [SMILES: Cc1noc(C)c1-c1cc(S(=O)(=O)NC2CCCC2)c2cc(NCCN3CCOCC3)c(=O)[nH]c2c1] | 652 | 560 |
| 91 | N-cyclopentyl-7-(3,5-dimethylisoxazol-4-yl)-3-((2-(2-hydroxyethoxy)ethyl)amino)-2-oxo-1,2-dihydroquinoline-5-sulfonamide | 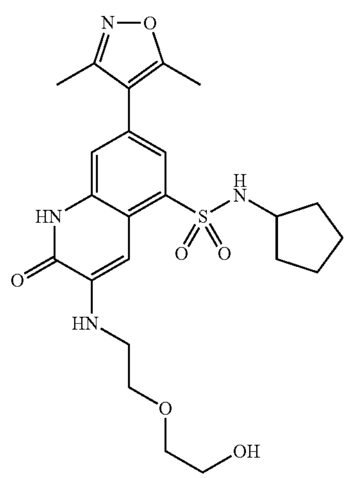 [SMILES: Cc1noc(C)c1-c1cc(S(=O)(=O)NC2CCCC2)c2cc(NCCOCCO)c(=O)[nH]c2c1] | 705 | 473 |
| 92 | N-cyclopentyl-3-((1,3-dihydroxypropan-2-yl)amino)-7-(3,5-dimethylisoxazol-4-yl)-2-oxo-1,2-dihydroquinoline-5-sulfonamide | 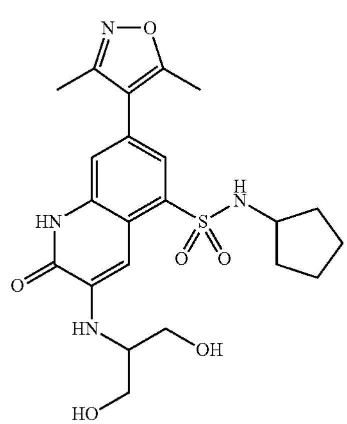 [SMILES: Cc1noc(C)c1-c1cc(S(=O)(=O)NC2CCCC2)c2cc(NC(CO)CO)c(=O)[nH]c2c1] | 897 | 493 |

TABLE 1-continued

Representative Compounds

| NO | NAME | STRUCTURE | Epic K$_d$ BRD4 1 | Epic K$_d$ BRD4 2 |
|----|------|-----------|-------------------|-------------------|
| 93 | N-cyclopentyl-3-((2,3-dihydroxypropyl)amino)-7-(3,5-dimethylisoxazol-4-yl)-2-oxo-1,2-dihydroquinoline-5-sulfonamide | 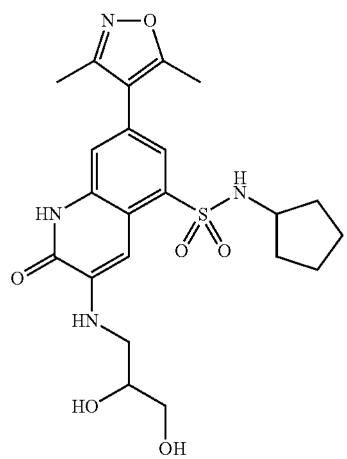 [SMILES: Cc1noc(C)c1-c1cc(S(=O)(=O)NC2CCCC2)c2cc(NCC(O)CO)c(=O)[nH]c2c1] | 951 | 417 |
| 94 | 3-((3-aminopropyl)amino)-N-cyclopentyl-7-(3,5-dimethylisoxazol-4-yl)-2-oxo-1,2-dihydroquinoline-5-sulfonamide | 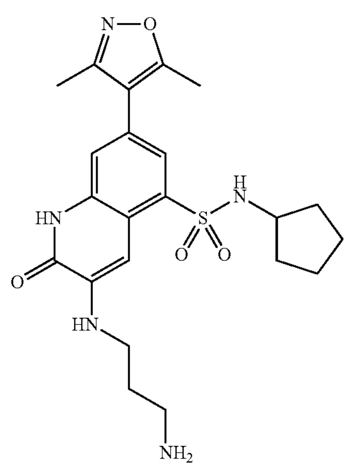 [SMILES: Cc1noc(C)c1-c1cc(S(=O)(=O)NC2CCCC2)c2cc(NCCCN)c(=O)[nH]c2c1] | 743 | 569 |
| 95 | N-cyclopentyl-3-((3-(dimethylamino)propyl)amino)-7-(3,5-dimethylisoxazol-4-yl)-2-oxo-1,2-dihydroquinoline-5-sulfonamide | 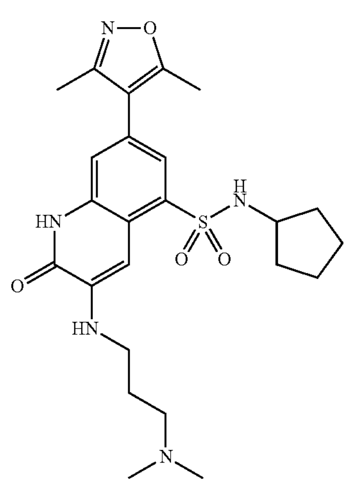 [SMILES: Cc1noc(C)c1-c1cc(S(=O)(=O)NC2CCCC2)c2cc(NCCCN(C)C)c(=O)[nH]c2c1] | 798 | 503 |

TABLE 1-continued

Representative Compounds

| NO | NAME | STRUCTURE | Epic K$_d$ BRD4 1 | Epic K$_d$ BRD4 2 |
|---|---|---|---|---|
| 96 | N-cyclopentyl-7-(3,5-dimethylisoxazol-4-yl)-3-(oxetan-3-ylamino)-2-oxo-1,2-dihydroquinoline-5-sulfonamide | 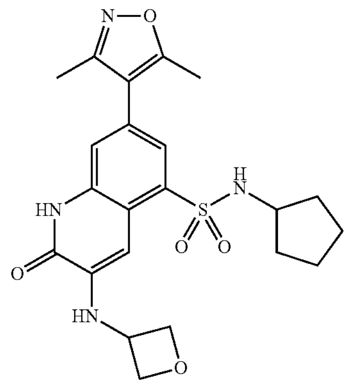 [SMILES: Cc1noc(C)c1-c1cc(S(=O)(=O)NC2CCCC2)c2cc(NC3COC3)c(=O)[nH]c2c1] | 467 | 433 |
| 97 | N-cyclopentyl-7-(3,5-dimethylisoxazol-4-yl)-3-((1-hydroxy-2-methylpropan-2-yl)amino)-2-oxo-1,2-dihydroquinoline-5-sulfonamide | 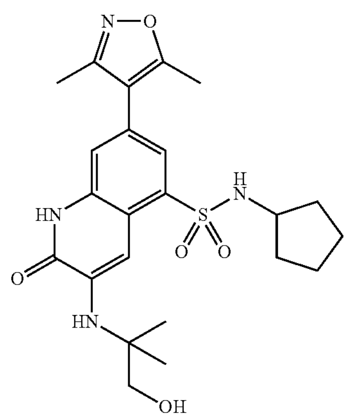 [SMILES: Cc1noc(C)c1-c1cc(S(=O)(=O)NC2CCCC2)c2cc(NC(C)(C)CO)c(=O)[nH]c2c1] | 936 | 658 |
| 98 | N-cyclopentyl-7-(3,5-dimethylisoxazol-4-yl)-3-((2-hydroxy-2-methylpropyl)amino)-2-oxo-1,2-dihydroquinoline-5-sulfonamide | 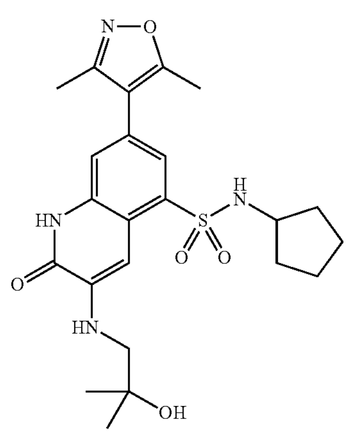 [SMILES: Cc1noc(C)c1-c1cc(S(=O)(=O)NC2CCCC2)c2cc(NCC(C)(C)O)c(=O)[nH]c2c1] | 1034 | 545 |

TABLE 1-continued

Representative Compounds

| NO | NAME | STRUCTURE | Epic K$_d$ BRD4 1 | Epic K$_d$ BRD4 2 |
|---|---|---|---|---|
| 99 | 3-((2-amino-2-methylpropyl)amino)-N-cyclopentyl-7-(3,5-dimethylisoxazol-4-yl)-2-oxo-1,2-dihydroquinoline-5-sulfonamide | 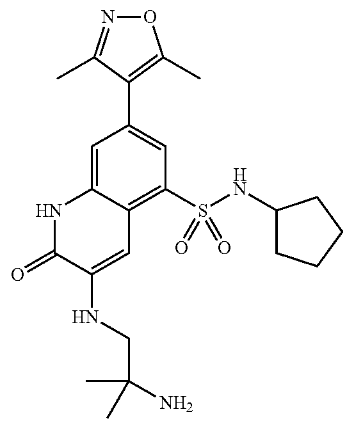 [SMILES: Cc1noc(C)c1-c1cc(S(=O)(=O)NC2CCCC2)c2cc(NCC(C)(C)N)c(=O)[nH]c2c1] | 671 | 632 |
| 100 | (R)-7-(3,5-dimethylisoxazol-4-yl)-N-(1,1,1-trifluoropropan-2-yl)quinoline-5-sulfonamide | 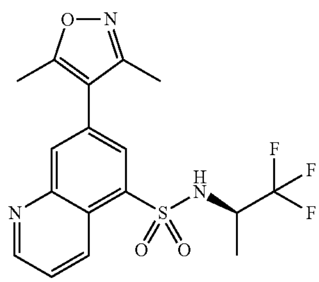 [SMILES: Cc1noc(C)c1-c1cc(S(=O)(=O)N[C@H](C)C(F)(F)F)c2cccnc2c1] | 8946 | 11438 |

Provided are also compounds of Formula I, IA, IB, IC, ID, I', IE or IF, or a pharmaceutically acceptable salt thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Pharmaceutical Compositions

Compounds provided herein may be administered in the form of pharmaceutical compositions. Thus, provided herein are pharmaceutical compositions that contain, as the active ingredient, one or more of the compounds described herein, or a pharmaceutically acceptable salt thereof, and one or more pharmaceutically acceptable carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In some embodiments, the term "active ingredient" is used to indicate a compound of Formula I, IA, IB, IC, ID, I', IE or IF, or a pharmaceutically acceptable salt thereof which has biological activity. In other embodiments, an "active ingredient" is a compound having pharmaceutical utility.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, for example, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, and heterocyclic. Also included are amines where the two or three substituents, together with the amino nitrogen, form a heterocyclic or heteroaryl group. Specific examples of suitable amines include, for example, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, and N-ethylpiperidine.

Pharmaceutically acceptable acid addition salts may be prepared from inorganic and organic acids. Salts derived from inorganic acids include, for example, hydrochloric acid, hydrobromic acid, sulfuric acid, nitric acid, and phosphoric acid. Salts derived from organic acids include, for example, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, and salicylic acid.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Provided are also prodrugs of the compounds described herein. In some embodiments, the "prodrugs" described herein include any compound that becomes a compound of Formula I when administered to a subject, e.g., upon metabolic processing of the prodrug. Examples of prodrugs include derivatives of functional groups, such as a carboxylic acid group, in the compounds described herein. Exemplary prodrugs of a carboxylic acid group include, but are not limited to, carboxylic acid esters such as alkyl esters, hydroxyalkyl esters, arylalkyl esters, and aryloxyalkyl esters.

Provided are also solvates of the compounds described herein. A "solvate" is formed by the interaction of a solvent and a compound. Similarly, in other embodiments, "salts" include solvates of salts. Solvates may include pharmaceutically acceptable solvates, such as hydrates, including monohydrates and hemi-hydrates.

Modes of Administration

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral. In one embodiment, a mode for administration is by injection. The forms in which the compositions of Formula I, IA, IB, IC, ID, I', IE or IF, or a pharmaceutically acceptable salt thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound of Formula I, IA, IB, IC, ID, I', IE or IF, or a pharmaceutically acceptable salt thereof, in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via, for example, capsule or enteric coated tablets. In making the pharmaceutical compositions that include at least one compound of Formula I, IA, IB, IC, ID, I', IE or IF, or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula I, IA, IB, IC, ID, I', IE or IF, or a pharmaceutically acceptable salt thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from 1 mg to 2 g of a compound described herein. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 140 mg per kilogram of body weight per day. Such dosage levels may, in certain instances, be useful in the treatment of the above-indicated conditions. In other embodiments, dosage levels may be from 0.5 mg to 7 g per subject per day. The amount of active ingredient that may be combined with the vehicle to produce a single dosage form will vary depending upon the host treated and the particular mode of administration. Dosage unit foul's may contain from 1 mg to 500 mg of an active ingredient Frequency of dosage may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula I, IA, IB, IC, ID, I', IE or IF, or a pharmaceutically acceptable salt thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Compounds of Formula I, including compounds of any of Formulae IA, IB, IC, ID, I', IE and IF, may be used or combined with a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate;

compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan), corticosteroids (cortisone, dexamethasone, hydrocortisone, methylpednisolone, prednisone, and prednisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocannycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammall and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK; razoxane; rhizoxin; sizofuran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL®, Bristol Meyers Squibb Oncology, Princeton, N.J.) and docetaxel (TAXOTERE®, Rhone-Poulenc Rorer, Antony, France); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-11; topoisomerase inhibitor RFS 2000; difluoromethylomithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproternase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3, 4-dehydroproline, thiaproline, .alpha.-dipyridyl, beta-aminopropionitrile fumarate, 4-propyl-5-(4-pyridinyl)-2(3h)-oxazolone; methotrexate, mitoxantrone, heparin, interferons, macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The anti-neoplastic agent, anti-cancer agent, or anti-proliferation agent may be an inhibitor to Abl, activated CDC kinase (ACK), adenosine A2B receptor (A2B), apoptosis signal-regulating kinase (ASK) such as ASK1, Auroa kinase, BTK, BRD such as BRD4, c-Kit, c-Met, CDK-activating kinase (CAK), calmodulin-dependent protein kinase (CaMK), cyclin-dependent kinase (CDK), casein kinase (CK), discoidin domain receptor (DDR) such as DDR1 and/or DDR2, EGFR, focal adhesion kinase (FAK), Flt-3, FYN, glycogen synthase kinase (GSK), HCK, histone deacetylase (HDAC), IKK such as IKKβε, isocitrate dehydrogenase (IDH) such as IDH1, IKK, JAK such as JAK1, JAK2 and/or JAK3, KDR, lymphocyte-specific protein tyrosine kinase (LCK), lysyl oxidase protein, lysyl oxidase-like protein (LOXL) such as LOXL1, LOXL2, LOXL3, LOXL4, and/or LOXL5, LYN, matrix metalloprotease (MMP) such as MMP 1-10, MEK, mitogen-activated protein kinase (MAPK), NEK9, NPM-ALK, p38 kinase, platelet-derived growth factor (PDGF), phosphorylase kinase (PK), polo-like kinase (PLK), PI3K such as PI3Kγ, PI3Kδ, PI3Kβ, PI3Kα and/or pan-PI3K, protein kinase (PK) such as protein kinase A, B, and/or C, PYK, SYK, serine/threonine kinase TPL2, serine/threonine kinase STK, signal transduction and transcription (STAT), SRC, serine/threonine-protein kinase (TBK) such as TBK1, TIE, tyrosine kinase (TK), VEGFR, YES, or any combination thereof.

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM fludarabine, cyclophosphamide, mitoxantrone); bortezomib and rituximab; temsirolimus and rituximab; temsirolimus and Velcade®, Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D. T. PACE (dexamethasone, thalidomide, cisplatin, Adriamycin®, cyclophosphamide, etoposide).

Examples of immunotherapeutic agents treating lymphoma or leukemia include, but are not limited to, rituximab (such as Rituxan), alemtuzumab (such as Campath, Mab-Campath), anti-CD19 antibodies, anti-CD20 antibodies, anti- MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, obinutuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, ABT-199, ABT-737, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCI-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

Therapeutic Uses of BRD4 Inhibitors

Provided herein are also methods for inhibiting BRD4 to treat various diseases or conditions. The method includes administering a therapeutically effective amount of one or more compounds of Formula I, IA, IB, IC, ID, I', IE or IF, or a pharmaceutically acceptable salt thereof, or any compositions thereof (including any pharmaceutical compositions thereof).

The term "therapeutically effective amount" of a compound of Formula I, IA, IB, IC, ID, I', IE or IF, or a pharmaceutically acceptable salt thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of BRD4 activity. The therapeutically effective amount may vary depending on the subject, and disease or condition being treated, the weight and age of the subject, the severity of the disease or condition, and the manner of administering, which can readily be determined by one or ordinary skill in the art.

"Treatment" or "treating" is an approach for obtaining beneficial or desired results including clinical results. Beneficial or desired clinical results may include one or more of the following:

a) inhibiting the disease or condition (e.g., decreasing one or more symptoms resulting from the disease or condition, and/or diminishing the extent of the disease or condition);

b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

In some embodiments, the compounds of Formulae I, IA, IB, IC, ID, I', IE and IF, or a pharmaceutically acceptable salt thereof, is used to treat any diseases or conditions responsive to the inhibition of a bromodomain. In certain embodiments, the bromodomain is bromodomain-containing protein 4 (BRD4).

The term "inhibition" indicates a decrease in the baseline activity of a biological activity or process. "Inhibition of BRD4" or variants thereof refer to a decrease in activity of BRD4 as a direct or indirect response to the presence of a compound of Formulae I, IA, IB, IC, ID, I', IE and IF, or a pharmaceutically acceptable salt thereof, relative to the activity of BRD4 in the absence of the compound of Formulae I, IA, IB, IC, ID, I', IE and IF, or a pharmaceutically acceptable salt thereof.

In some embodiments, the compounds and compositions described herein may be used to treat an autoimmune disease, an inflammatory disease, a neurodegenerative disease, a cancer, a cardiovascular disorder, a renal disorder, a viral infection, or obesity.

In other embodiments, the compounds and compositions described herein may be used to treat a cardiovascular disorder, a renal disorder, or a viral infection. In certain embodiments, the compounds and compositions described herein may be used to treat rheumatoid arthritis, osteoarthritis, acute gout, psoriasis, systemic lupus erythematosus, multiple sclerosis, inflammatory bowel disease, asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, diabetes (including type I diabetes), acute rejection of transplanted organs, acute gout, giant cell arteritis, nephritis, glomerulonephritis, giant cell arteritis, Wegener's granulomatosis, Polyarteritis nodosa, Behcet's disease, Kawasaki disease, Takayasu's Arteritis, lymphomas, multiple myelomas, leukemias, and obesity.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of a BRD4 inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds of Formula I, IA, IB, IC, ID, I', IE or IF, or a pharmaceutically acceptable salt thereof, may be further characterized to examine the safety or tolerance dosage in human or non-human subjects. Such properties may be examined using commonly known methods to those skilled in the art.

Kits and Articles of Manufacture

Kits that include a compound of Formula I, IA, IB, IC, ID, I', IE or IF, or a pharmaceutically acceptable salt thereof, and suitable packaging are provided. In one embodiment, a kit further includes instructions for use. In one aspect, a kit includes a compound of Formula I, IA, IB, IC, ID, I', IE or IF, or a pharmaceutically acceptable salt thereof, and instructions for use of the compounds in the treatment of the diseases or conditions described herein.

Articles of manufacture that include a compound of Formula I, IA, IB, IC, ID, I', IE or IF, or a pharmaceutically acceptable salt thereof, in a suitable container are provided. The container may be a vial, jar, ampoule, preloaded syringe, and intravenous bag.

General Synthetic Methods

Methods for obtaining the novel compounds described herein will be apparent to those of ordinary skill in the art, suitable procedures being described, for example, in the reaction schemes and examples below, and in the references cited herein.

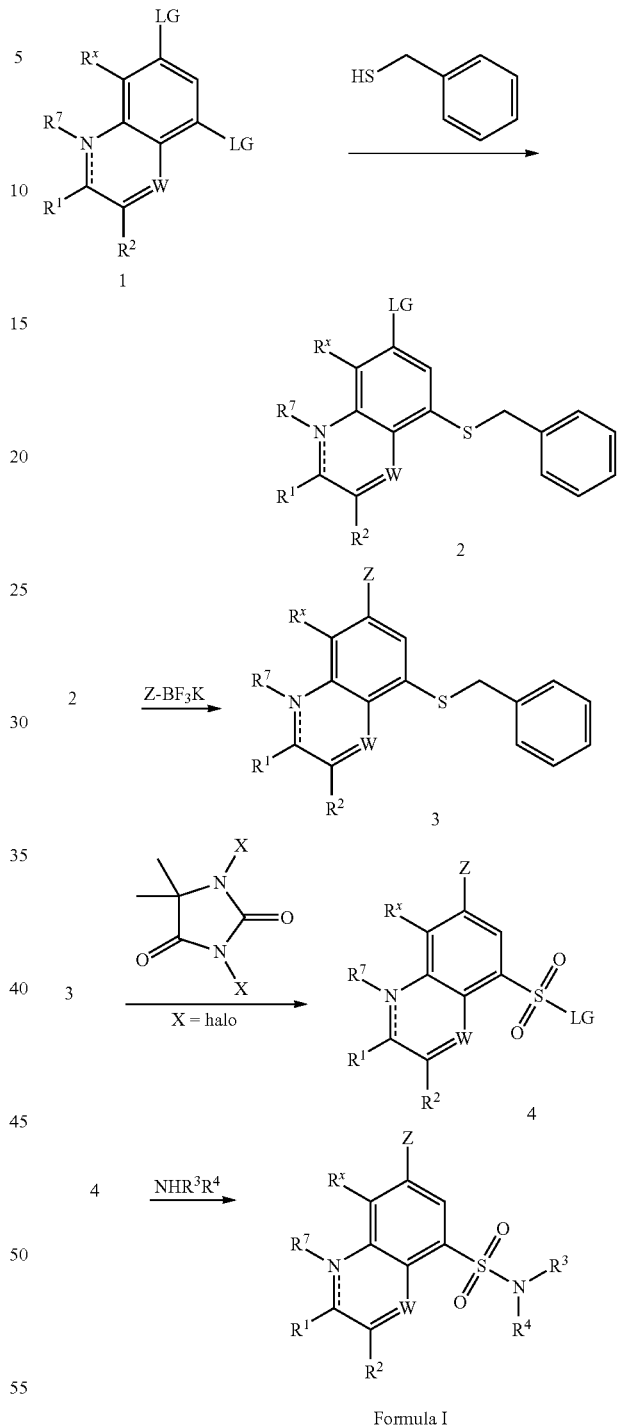

One exemplary method of preparing compounds of Formula I is shown in Reaction Scheme 1.

Step 1—Preparation of Formula 2

The compound of Formula 2 can be prepared by coupling commercially available benzyl mercaptan to commercially available compound of Formula 1 in the presence of a base. As shown above, $R^1$, $R^2$, $R^7$, $R^x$ and W substituents are as defined in the specification for compounds of Formula I. Substituents LG in Formula 1 may be any appropriate leaving group (e.g., F, Cl, Br), and X at each occurrence may be the same or different. The reaction is carried out in an appropriate solvent, such as dimethylformamide (DMF), at a temperature of about 0° C. for about 1 to 5 hours. The reaction mixture is allowed to warm to room temperature. When the reaction is substantially complete, the product of Formula 2 is isolated by conventional means, such as by extraction, followed by purification by chromatography of the residue on silica gel. Alternatively, the compound of Formula 2 may be used in the next step without purification.

Step 2—Preparation of Formula 3

The compound of Formula 2 then undergoes a Suzuki coupling reaction with a trifloroborate salt in the presence of a catalyst and base to obtain the compound of Formula 3. As shown above, the trifluoroborate salt is substituted with substituent Z, wherein Z is as defined in the specification for compounds of Formula I. It should be understood that boronic acid and boronate esters may also be used for the Suzuki coupling reaction. Suitable catalysts may include palladium catalysts, such as (1,3-bis(2,6-diisopropylphenyl)imidazolidene)(3-chloropyridyl)palladium(II) dichloride (Peppsi-iPr). Suitable bases may include, for example, cesium carbonate. Suitable solvents may include a combination of organic solvents and water, including, for example, dimethoxyethane and water. The reaction is carried out in an appropriate solvent under nitrogen, at an elevated temperature of about 70° C. to 100° C., for about 30 minutes to 5 hours. When the reaction is substantially complete, the reaction is allowed to cool to room temperature. The reaction mixture can be partitioned between an aqueous phase and an organic phase. The aqueous phase is discarded, and the organic phase is purified by chromatography on silica gel. Alternatively, the compound of Formula 3 may be used in the next step without purification.

Step 3—Preparation of Formula 4

Compound of Formula 3 can then be oxidized in the presence of an appropriately substituted haloimidazolidine-2,4-dione compound, for example, 1,3-dichloro-5,5-dimethylimidazolidine-2,4-dione. The reaction is typically conducted in the presence of an acid in an appropriate solvent. Suitable acids may include, for example, acetic acid. Suitable solvents may include a combination of solvents, including, for example, acetonitrile and water. The starting materials are combined at a temperature of about 0° C., and the reaction mixture is allowed to warm up to room temperature. When the reaction is substantially complete, the compound of Formula 4 is isolated by conventional means, such as by extraction using brine and an organic solvent such as ethyl acetate. The organic layer is dried and concentrated. The crude compound of Formula 4 may be purified using chromatography on silica gel, or be used in the next step without purification.

Step 4—Preparation of Formula I

An appropriately substituted amine is reacted with the compound of Formula 4 in an appropriate solvent to yield the product of Formula I. As shown above, the amine has substituents $R^3$ and $R^4$, which are as defined in the specification for compounds of Formula I. Suitable solvents may include organic solvents, such as ethyl acetate. The reaction is carried out at room temperature, for 5 minutes to an hour. When the reaction is substantially complete, the compound of Formula I is isolated by convention means, such as by extraction, and purified by chromatography on silica gel.

Another exemplary method of preparing compounds of Formula I is shown in Reaction Scheme 2.

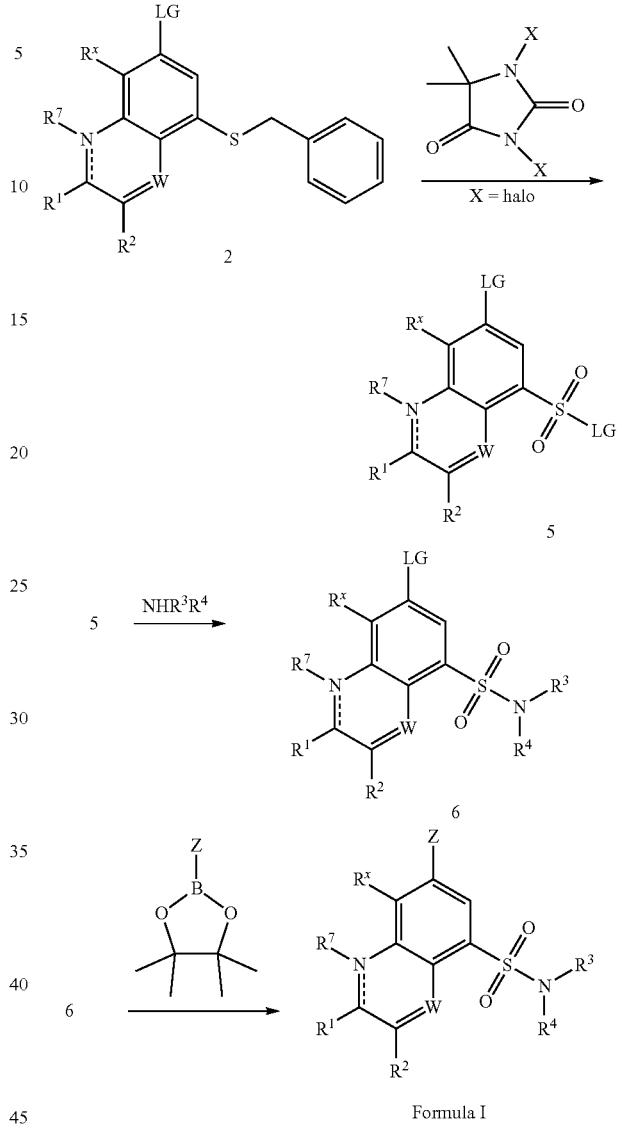

Step 1—Preparation of Formula 5

The compound of Formula 2 can be prepared according to the general procedure described in Reaction Scheme 1 above. Compound of Formula 2 can then be oxidized in the presence of an appropriately substituted haloimidazolidine-2,4-dione compound, for example, 1,3-dichloro-5,5-dimethylimidazolidine-2,4-dione. The reaction is typically conducted in the presence of an acid in an appropriate solvent. Suitable acids may include, for example, acetic acid. Suitable solvents may include a combination of solvents, including, for example, acetonitrile and water. The starting materials are combined at a temperature of about 0° C., and the reaction mixture is allowed to warm up to room temperature. When the reaction is substantially complete, the compound of Formula 5 is isolated by conventional means, such as by extraction using brine and an organic solvent such as ethyl acetate. The organic layer is dried and concentrated. The crude compound of Formula 5 may be purified using chromatography on silica gel, or be used in the next step without purification.

Step 2—Preparation of Formula 6

An appropriately substituted amine is reacted with the compound of Formula 5 in an appropriate solvent to yield the product of Formula 6. As shown above, the amine has substituents $R^3$ and $R^4$, which are as defined in the specification for compounds of Formula I. Suitable solvents may include organic solvents, such as ethyl acetate. The reaction is carried out at room temperature, for 5 minutes to an hour. When the reaction is substantially complete, the compound of Formula 6 is isolated by convention means, such as by extraction, and purified by chromatography on silica gel. Alternatively, the compound of Formula 6 may be used in the next step without purification.

Step 3—Preparation of Formula I

The compound of Formula 6 then undergoes a Suzuki coupling reaction with a boronic acid derivative in the presence of a catalyst and base to obtain the product of Formula I. As shown above, the boronic acid derivative is substituted with Z, wherein Z is as defined in the specification for compounds of Formula I. Suitable boronic acid derivatives may include boronic acid esters, such as, for example, 3,5-dimethylisoxazole-4-boronic acid pinacol ester. Suitable catalysts may include palladium catalysts, such as Peppsi-iPr. Suitable bases may include, for example, cesium carbonate. Suitable solvents may include a combination of organic solvents and water, including, for example, dimethoxyethane and water. The reaction is carried out in an appropriate solvent under nitrogen, at an elevated temperature of about 70° C. to 100° C., for about 30 minutes to 5 hours. When the reaction is substantially complete, the reaction is allowed to cool to room temperature. The reaction mixture can be partitioned between an aqueous phase and an organic phase. The aqueous phase is discarded, and the organic phase is purified by chromatography on silica gel to obtain the compound of Formula I.

Another exemplary method of preparing compounds of Formula I is shown in Reaction Scheme 3.

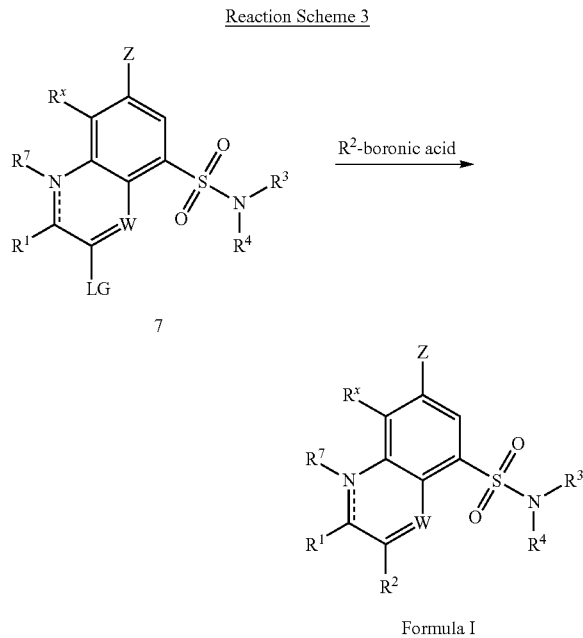

$R^3$, $R^4$, $R^7$, Rx, W and Z in Formula 7 are as defined in the specification for compounds of Formula I. Substituent LG in Formula 7 may be any appropriate leaving group (e.g., F, Cl, Br). The boronic acid derivative is substituted with $R^2$, in which $R^2$ is aryl or heteroaryl as defined in the specification for compounds of Formula I. Suitable catalysts may include palladium catalysts, such as (1,3-bis(2,6-diisopropylphenyl)imidazolidene)(3-chloropyridyl)palladium(II) dichloride (Peppsi-iPr). Suitable bases may include, for example, cesium carbonate. Suitable solvents may include a combination of organic solvents and water, including, for example, dimethoxyethane and water. The reaction is carried out in an appropriate solvent under nitrogen, at an elevated temperature of about 70° C. to 100° C., for about 30 minutes to 5 hours. When the reaction is substantially complete, the reaction is allowed to cool to room temperature. The reaction mixture can be concentrated and purified by any suitable method, including for example, chromatography on silica gel or preparative HPLC to obtain the compound of Formula I.

Yet another exemplary method of preparing compounds of Formula I is shown in Reaction Scheme 4.

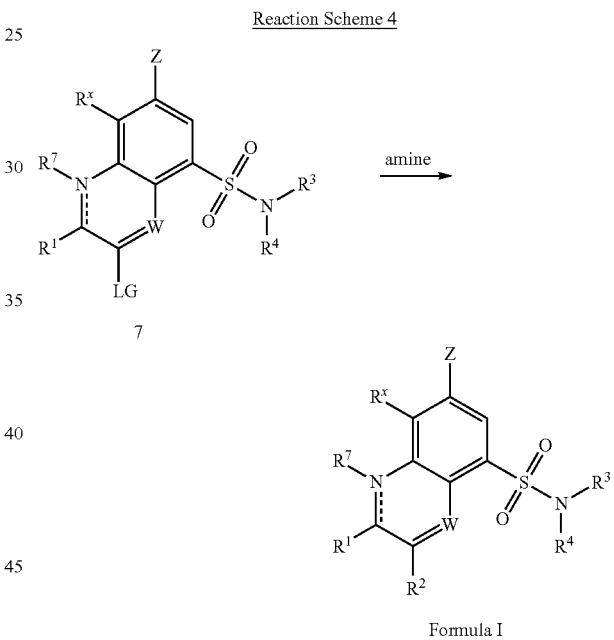

The compound of Formula 7 may be reacted with an amine in the present of copper sulfate and proline in the presence of a suitable solvent to produce a compound of Formula I. Substituents $R^1$, $R^3$, $R^4$, $R^7$, Rx, W and Z in Formula 7 are as defined in the specification for compounds of Formula I. Substituent X in Formula 7 may be any appropriate leaving group (e.g., F, Cl, Br). The amine may be any amine described for $R^2$ in the specification for compounds of Formula I. Suitable solvents may include, for example, methoxyethanol. The reaction mixture is carried out at 100° C. to 150° C. for 1 hour to 5 hours. When the reaction is substantially complete, the reaction is allowed to cool to room temperature. The reaction mixture can be concentrated and purified by any suitable method, including for example, chromatography on silica gel or preparative HPLC to obtain the compound of Formula I.

The following examples are included to demonstrate certain preferred embodiments. It should be appreciated by those of skill in the art that the techniques disclosed in the examples The compound of Formula 7 may be reacted with a boronic acid derivative, a catalyst and a base in the presence of a solvent to produce a compound of Formula I. Substituents $R^1$, which follow represent techniques discovered by the inventor to function well in the practice of the invention, and thus can be considered to constitute certain preferred modes for its practice. However, those of skill in the art should, in light of the present disclosure, appreciate that many changes can be made in the specific embodiments which are disclosed, and still obtain a like or similar results without department from the spirit and the scope of the invention.

EXAMPLES

The following abbreviations are used in the Examples below:
DMF dimethylformamide
HATU 2-(1H-7-azabenzotriazol-1-yl)-1,1,3,3-tetramethyl uronium hexafluorophosphate methanaminium
HEPES (4-(2-hydroxyethyl)-1-piperazineethanesulfonic acid mCPBA meta chloroperbenzoic acid
MeCN acetonitrile
NaCl sodium chloride
NaOH sodium hydroxide
Na$_2$SO$_4$ sodium sulphate
NBS N-bromosuccinimide
Peppsi-iPr (1,3-bis(2,6-diisopropylphenyl)imidazolidene) (3-chloropyridyl)palladium(II) dichloride
POCl$_3$ phosphoryl chloride
rf retention factor
TFA trifluoroacetic acid
TCEP tris(2-carboxyethyl)phosphine Example 1

Preparation of 4-(5-(benzylthio)quinolin-7-yl)-3,5-dimethylisoxazole

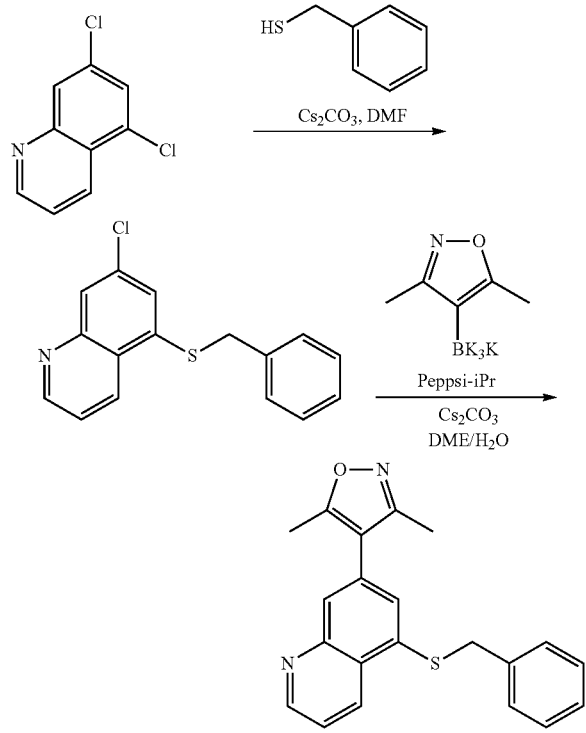

Benzyl mercaptan (6 mL, 50.5 mmol) was added dropwise to a mixture of 5,7-dichloroquinoline (10 g, 50.5 mmol), cesium carbonate (20 g, 60 mmol) and DMF (50 mL) at 0° C. The reaction mixture was allowed to warm to room temperature, stirred for 2 hours and partitioned between ethyl acetate and water. The organic phase was washed with brine, dried with sodium sulfate and concentrated. Purification by column chromatography gave the 5-(benzylthio)-7-chloroquinoline (rf=0.5 in 2:1 hexanes/ethyl acetate) as a crystalline yellow solid. The undesired regioisomer elutes afterwards (rf=0.4 in 2:1 hexanes/ethyl acetate). The reaction is mildly selective for the desired isomer.

To a mixture of 5-(benzylthio)-7-chloroquinoline (3.94 g, 13.4 mmol), trifluoroborate (1.5-2.0 equiv, Aldrich catalogue number 750301), Peppsi-iPr (2 mol %, Aldrich catalogue number 669032) and cesium carbonate (4 equiv) under nitrogen was added dimethoxyethane (20 mL) and water (15 mL). The reaction mixture was heated to 90° C. and is usually complete after 1 hour. The mixture was partitioned between water and acetate. The aqueous phase was discarded and the products were purified by silica gel (rf=0.22 in 2:1 hexanes/ethyl acetate) to give the desired product, 4-(5-(benzylthio)quinolin-7-yl)-3,5-dimethylisoxazole.

Example 2

Preparation of 7-(3,5-dimethylisoxazol-4-quinoline-5-sulfonyl chloride

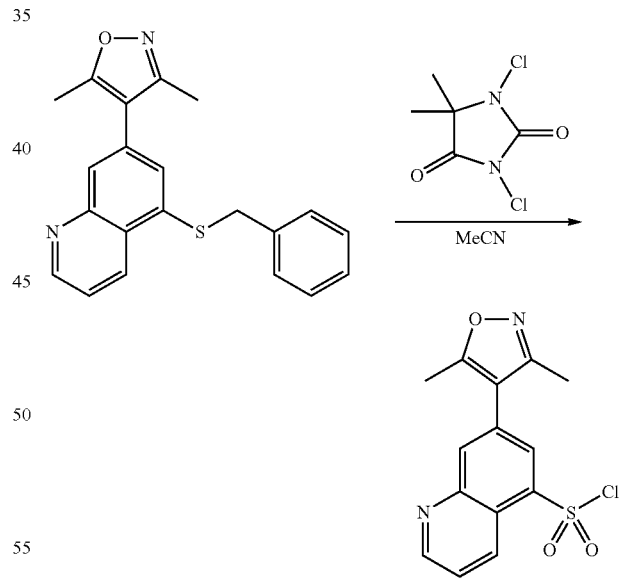

Solid 1,3-dichloro-5,5-dimethylimidazolidine-2,4-dione (680 mg, 3.45 mmol) was added to an ice cold mixture of 4-(5-(benzylthio)quinolin-7-yl)-3,5-dimethylisoxazole (600 mg, 1.73 mmol), acetonitrile (15 mL), acetic acid (0.6 mL) and water (0.4 mL). The reaction mixture was allowed to warm to room temperature and stirred for 1 hour before being partitioned between brine and ethyl acetate. The organic layer was dried using sodium sulfate and evaporated. The crude sulfonyl chloride was purified on silica gel (rf 0.3 in 2:1 hexanes:ethyl acetate) to afford 7-(3,5-dimethylisoxazol-4-yl)quinoline-5-sulfonyl chloride as a crystalline solid.

Example 3

Preparation of N-cyclopentyl-7-(3,5-dimethylisoxazol-4-yl)quinoline-5-sulfonamide

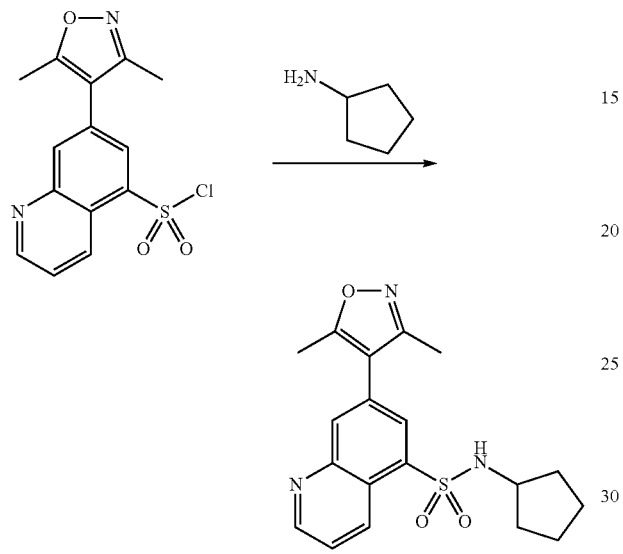

Cyclopentyl amine (0.4 mL, 4 mmol) was added to a solution of 7-(3,5-dimethylisoxazol-4-yl)quinoline-5-sulfonyl chloride (500 mg, 1.55 mmol) in ethyl acetate (15 mL). The reaction was stirred at room temperature for 15 minutes before being partitioned between an aqueous solution of citric acid and ethyl acetate. The organic layer was washed with brine and dried over sodium sulfate. Purification on silica gel (rf=0.07 in 2:1 hexanes ethyl acetate) afforded N-cyclopentyl-7-(3,5-dimethylisoxazol-4-yl)quinoline-5-sulfonamide.

$C_{19}H_{21}N_3O_3S$. 372.1 (M+1). $^1H$ NMR (DMSO) δ 9.07 (m, 2H), 8.30 (s, 1H), 8.16 (s, 1H), 8.13 (d, J=2 Hz, 1H), 7.76 (m, 1H), 3.54 (m, 1H), 2.51 (s, 3H), 2.32 (s, 3H), 1.6-1.2 (m, 8H).

Example 4

Preparation of (1S,2R)—N-cyclopentyl-2-(7-(3,5-dimethylisoxazol-4-yl)quinoline-5-sulfonamido)cyclopentanecarboxamide

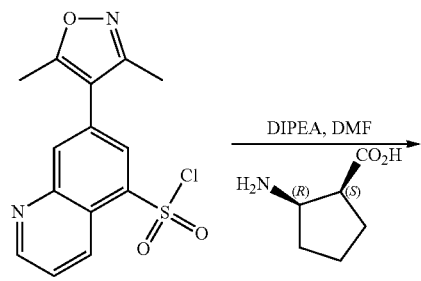

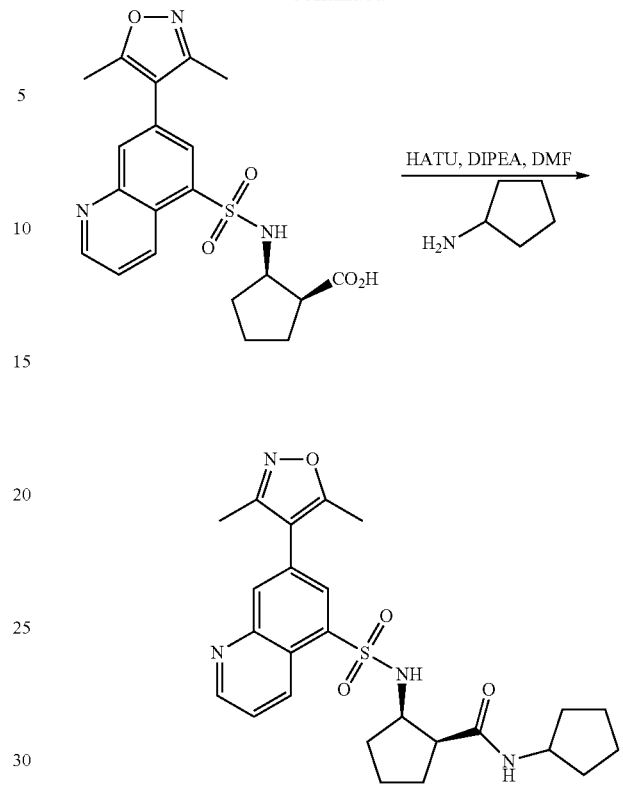

To a mixture of amino acid (181 mg, 1.40 mmol), water (2 mL) and acetone (2 mL) was added 1N NaOH (1.4 mL, 1.40 mmol) with stirring. The reaction mixture was cooled to 0° C., and a solution of sulfonyl chloride (200 mg, 0.62 mmol) in acetone (3 mL) was added slowly. After stirring at 0° C. for 5 min, Hunig's base (250 uL, 1.40 mmol) was added and the mixture was stirred at 0° C. for another 10 min. Then the ice bath was removed, and the reaction mixture was allowed to stir at room temperature until the starting material sulfonyl chloride disappeared. Water (50 mL) was added to the mixture, followed by extracted with ethyl ether (20 mL). The aqueous layer was acidified by citric acid to pH 2-3, followed by extraction with ethyl acetate (4×50 mL). The combined organic layer was washed with 30% aqueous ammonium chloride (80 mL), brine (100 mL), dried over $Na_2SO_4$, and concentrated to afford pale yellow solid as (1S,2R)-2-(7-(3,5-dimethylisoxazol-4-yl)quinoline-5-sulfonamido)cyclopentanecarboxylic acid. LCMS m/z 416.1 (M+H). With no further purification, the product was used in the next step.

To a mixture of HATU (38 mg, 0.10 mmol), cyclopentanamine (9 mg, 0.10 mmol), and 1S,2R)-2-(7-(3,5-dimethylisoxazol-4-yl)quinoline-5-sulfonamido)cyclopentanecarboxylic acid (21 mg, 0.05 mmol) in anhydrous DMF (1 mL), was added slowly Hunig's base (30 uL, 0.16 mmol) with stirring until the starting material acid disappeared (about 1 hr). The reaction mixture was acidified with aqueous citric acid to pH 2-3, then subjected to preparative HPLC to give (1S,2R)—N-cyclopentyl-2-(7-(3,5-dimethylisoxazol-4-yl)quinoline-5-sulfonamido)cyclopentanecarboxamide.

Example 5

Preparation of 2-chloro-N-cyclopentyl-7-(3,5-dimethylisoxazol-4-yl)quinoline-5-sulfonamide

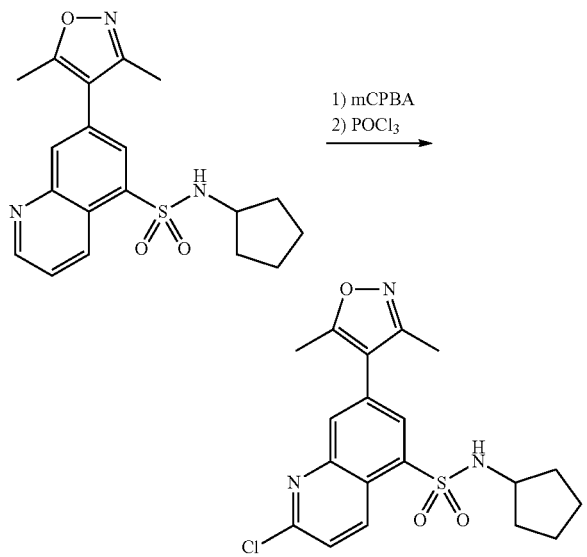

A mixture of N-cyclopentyl-7-(3,5-dimethylisoxazol-4-yl)quinoline-5-sulfonamide (272 mg, 0.73 mmol) and mCPBA (max 77% by weight, 364 mg) in dichloromethane (5 mL) was stirred at room temperature for 2 hours. The reaction mixture was diluted with ethyl acetate and washed with aqueous sodium sulfite solution followed by brine. The organic layer was dried over sodium sulfate and concentrated. The residue was dissolved in POCl$_3$ and heated at 80° C. for 1 hour. The reaction mixture was concentrated before being partitioned between ethyl acetate and aqueous sodium bicarbonate. The organic phase was dried over sodium sulfate and purified on silica gel (rf=0.42 in 2:1 hexanes:ethyl acetate) to give 2-chloro-N-cyclopentyl-7-(3,5-dimethylisoxazol-4-yl)quinoline-5-sulfonamide.

$C_{19}H_{20}ClN_3O_3S$. 406.9 (M+1). $^1$H NMR (DMSO) δ 9.08 (d, J=9.2 Hz, 1H), 8.25 (m, 2H), 8.13 (d, J=2.0 Hz, 1H), 7.85 (d, J=9.2 Hz, 1H), 3.49 (m, 1H), 2.51 (s, 3H), 2.31 (s, 3H), 1.6-1.2 (m, 8H).

Example 6

Preparation of N-cyclopentyl-2-cyclopropyl-7-(3,5-dimethylisoxazol-4-yl)quinoline-5-sulfonamide

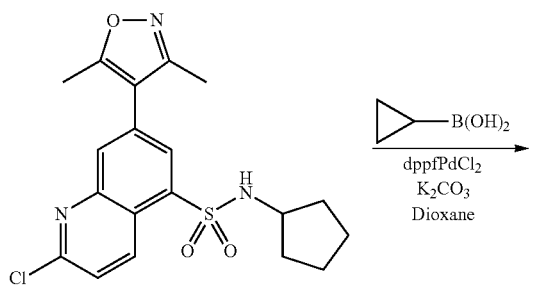

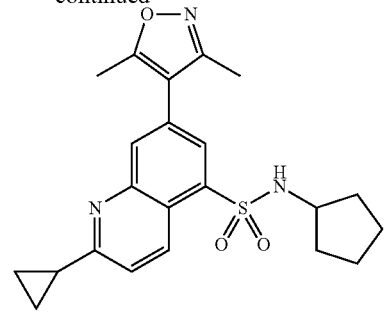

A mixture of 2-chloro-N-cyclopentyl-7-(3,5-dimethylisoxazol-4-yl)quinoline-5-sulfonamide (23 mg, 0.057 mmol), cyclopropaneboronic acid (50 mg, 10 equiv) dppf PdCl2 (8 mg, 20 mol %), potassium carbonate (60 mg) and dioxane (1 mL) was purged with nitrogen and heated at 110° C. for 1 hour. The reaction mixture was concentrated and purified by preparative HPLC to give the desired product, N-cyclopentyl-2-cyclopropyl-7-(3,5-dimethylisoxazol-4-yl)quinoline-5-sulfonamide.

$C_{22}H_{25}N_3O_3S$. 412.1 (M+1). $^1$H NMR (DMSO) δ 8.91 (d, J=9.2 Hz, 1H), 8.11 (d, J=7.2 Hz, 1H), 8.06 (s, 1H), 7.97 (d, J=2.0 Hz, 1H), 7.63 (d, J=9.2 Hz, 1H), 3.48 (m, 1H), 2.51 (s, 3H), 2.36 (m, 1H), 2.84 (s, 3H), 1.6-1.2 (m, 8H), 1.14 (m, 4H).

Example 7

Preparation of N-cyclopentyl-2-((cyclopropylmethyl)amino)-7-(3,5-dimethylisoxazol-4-yl)quinoline-5-sulfonamide

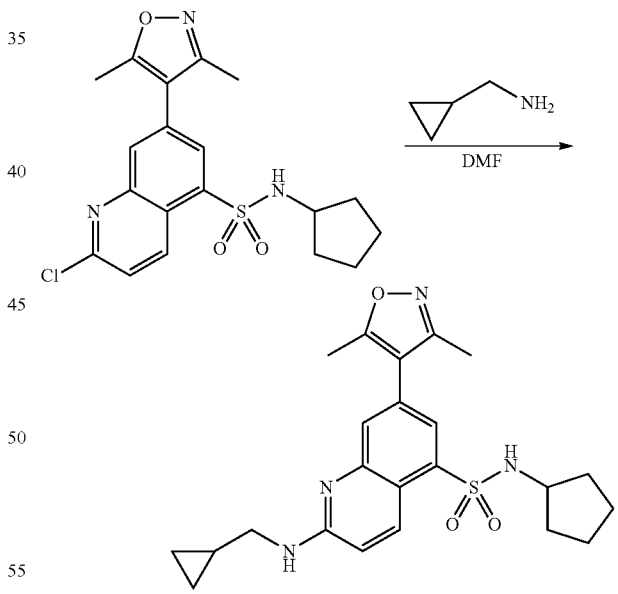

A mixture of 2-chloro-N-cyclopentyl-7-(3,5-dimethylisoxazol-4-yl)quinoline-5-sulfonamide (23 mg, 0.057 mmol), cyclopropylmethyl amine (0.2 mL) and DMF (0.5 mL) was heated at 110° C. for 1 hour. The reaction mixture was purified by preparative HPLC to give the desired product, N-cyclopentyl-2-((cyclopropylmethyl)amino)-7-(3,5-dimethylisoxazol-4-yl)quinoline-5-sulfonamide.

$C_{23}H_{28}N_4O_3S$. 441.1 (M+1). $^1$H NMR (DMSO) δ 8.70 (br, 1H), 8.2-7.7 (br, 3H), 7.15 (br, 1H), 3.51 (m, 1H), 3.36 (m, 2H), 2.51 (s, 3H), 2.30 (s, 3H), 1.6-1.2 (m, 8H), 1.18 (m, 1H), 0.57 (m, 2H), 0.33 (m, 2H).

Example 8

Preparation of N-cyclopentyl-2-(cyclopropylmethoxy)-7-(3,5-dimethylisoxazol-4-yl)quinoline-5-sulfonamide

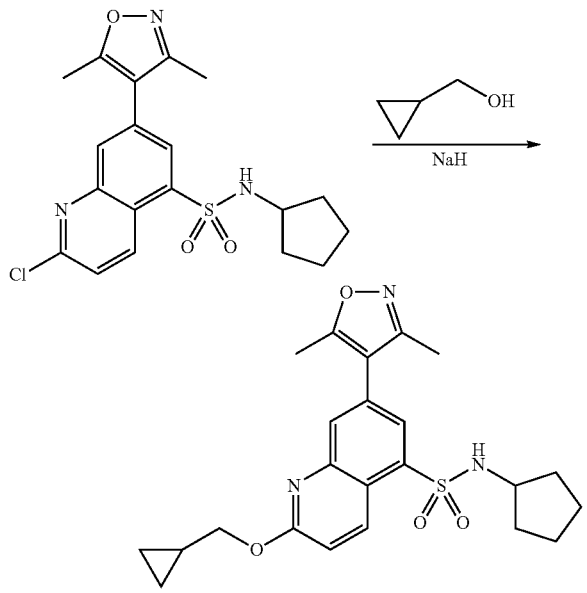

A mixture of 2-chloro-N-cyclopentyl-7-(3,5-dimethylisoxazol-4-yl)quinoline-5-sulfonamide (18 mg, 0.044 mmol) and cyclopropylmethanol (1 mL) was treated with excess sodium hydride and heated to 60° C. overnight. The mixture was concentrated and purified by preparative HPLC to give the desired product, N-cyclopentyl-2-(cyclopropylmethoxy)-7-(3,5-dimethylisoxazol-4-yl)quinoline-5-sulfonamide.

$C_{23}H_{27}N_3O_4S$. 442.1.1 (M+1). $^1$H NMR (DMSO) δ 8.94 (d, J=8.8 Hz, 1H), 8.10 (d, J=7.2 Hz, 1H), 7.97 (d, J=1.6 Hz, 1H), 7.91 (d, J=1.6 Hz, 1H), 7.28 (d, J=8.8 Hz, 1H), 4.30 (d, J=6.8 Hz, 2H), 3.48 (m, 1H), 2.51 (s, 3H), 2.49 (m, 1H), 2.29 (s, 3H), 1.6-1.2 (m, 8H), 0.60 (m, 2H), 0.41 (m, 2H).

Example 9

Preparation of N-cyclopentyl-7-(3,5-dimethylisoxazol-4-yl)-2-oxo-1,2-dihydroquinoline-5-sulfonamide

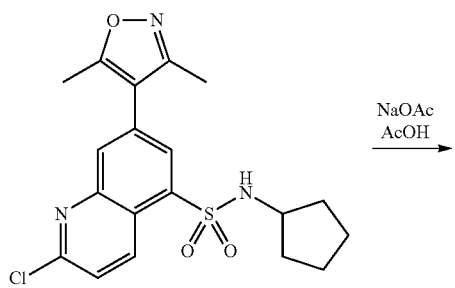

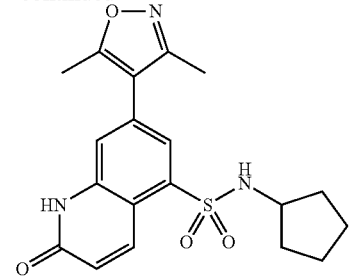

A mixture of 2-chloro-N-cyclopentyl-7-(3,5-dimethylisoxazol-4-yl)quinoline-5-sulfonamide (350 mg, 0.86 mmol) and sodium acetate (700 mg, 10 equiv) in acetic acid (10 mL) was refluxed overnight. The mixture was partitioned between sodium bicarbonate solution and ethyl acetate. The organic phase was washed with aqueous sodium bicarbonate solution and dried over sodium sulfate to give N-cyclopentyl-7-(3,5-dimethylisoxazol-4-yl)-2-oxo-1,2-dihydroquinoline-5-sulfonamide as a white powder.

$C_{19}H_{21}N_3O_4S$. 388.1 (M+1). $^1$H NMR (DMSO) δ 12.07 (s, 1H), 8.58 (d, J=10 Hz, 1H), 8.11 (d, J=7.2 Hz, 1H), 7.64 (d, J=1.6 Hz, 1H), 7.57 (d, J=1.6 Hz, 1H), 6.71 (dd, J=10, 1.6 Hz, 1H), 3.50 (m, 1H), 2.49 (s, 3H), 2.28 (s, 3H), 1.6-1.4 (m, 8H).

Example 10

Preparation of 3-bromo-N-cyclopentyl-7-(3,5-dimethylisoxazol-4-yl)-2-oxo-1,2-dihydroquinoline-5-sulfonamide

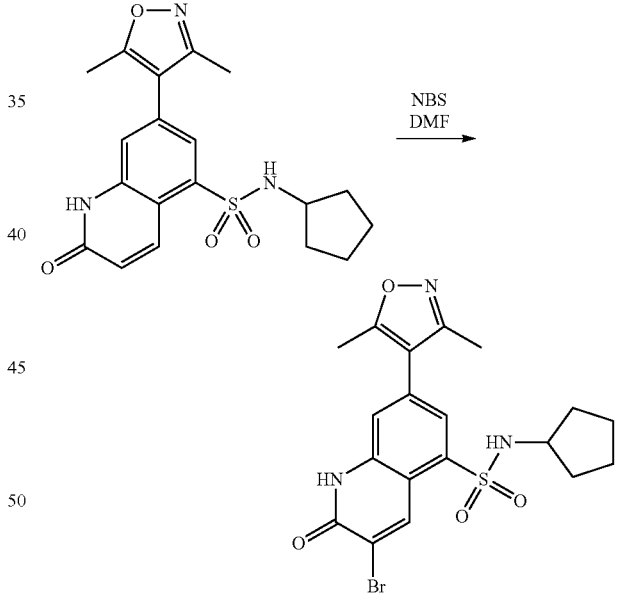

A solution of N-cyclopentyl-7-(3,5-dimethylisoxazol-4-yl)-2-oxo-1,2-dihydroquinoline-5-sulfonamide (100 mg, 0.26 mmol) and NBS (150 mg, 3 equiv) was heated at 80° C. for 1 hour. The reaction mixture was partitioned between aqueous sodium bicarbonate solution and ethyl acetate. The organic layer was washed with brine, dried over sodium sulfate and purified on silica gel (rf=0.75 in ethyl acetate) to give 3-bromo-N-cyclopentyl-7-(3,5-dimethylisoxazol-4-yl)-2-oxo-1,2-dihydroquinoline-5-sulfonamide as a white powder.

$C_{19}H_{20}BrN_3O_4S$. 467.1 (M+1). $^1$H NMR (DMSO) δ 12.65 (s, 1H), 9.06 (s, 1H), 8.31 (d, J=9.2 Hz, 1H), 7.71 (s, 1H), 7.62 (s, 1H), 3.51 (m, 1H), 2.50 (s, 3H), 2.30 (s, 3H), 1.65-1.25 (m, 8H).

Example 11

Preparation of 3-cyano-N-cyclopentyl-7-(3,5-dimethylisoxazol-4-yl)-2-oxo-1,2-dihydroquinoline-5-sulfonamide

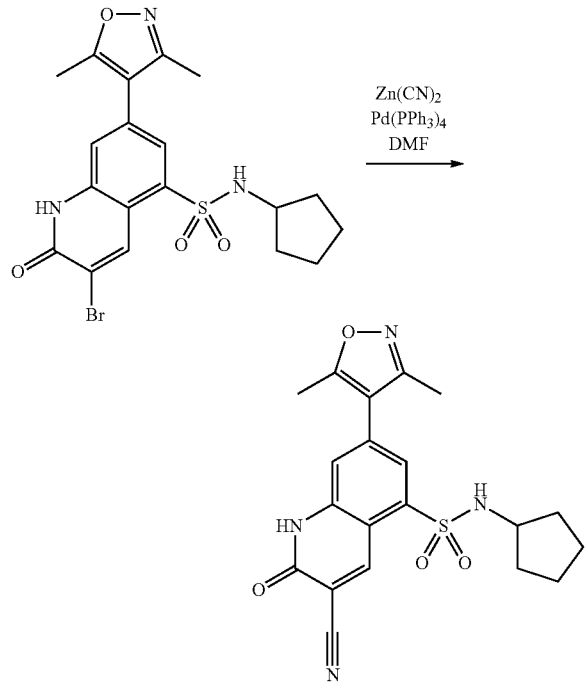

A mixture of 3-bromo-N-cyclopentyl-7-(3,5-dimethylisoxazol-4-yl)-2-oxo-1,2-dihydroquinoline-5-sulfonamide (16 mg, 0.034 mmol), zinc cyanide (20 mg, 5 equiv), Pd(PPh$_3$)$_4$ (4 mg, 10 mol %) and DMF was heated at 135° C. for 2 hours. The reaction mixture was purified by preparative HPLC to give 3-cyano-N-cyclopentyl-7-(3,5-dimethylisoxazol-4-yl)-2-oxo-1,2-dihydroquinoline-5-sulfonamide.

$C_{20}H_{20}N_4O_4S$. 413.1 (M+1). $^1$H NMR (DMSO) δ 12.83 (s, 1H), 9.20 (s, 1H), 8.29 (d, J=8.0 Hz, 1H), 7.76 (s, 1H), 7.62 (s, 1H), 3.48 (m, 1H), 2.51 (s, 3H), 2.30 (s, 3H), 1.6-1.2 (m, 8H).

Example 12

Preparation of N-cyclopentyl-2-(difluoromethyl)-7-(3,5-dimethylisoxazol-4-yl)quinoline-5-sulfonamide

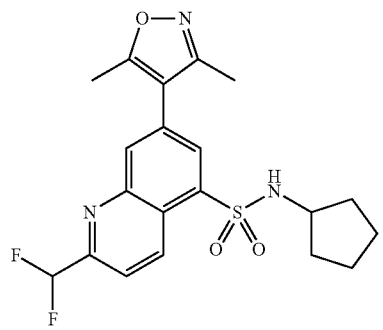 [SMILES: Cc1noc(C)c1-c1cc(S(=O)(=O)NC2CCCC2)c2ccc(C(F)F)nc2c1]

$C_{20}H_{21}F_2N_3O_3S$. 422.1 (M+1). $^1$H NMR (DMSO) δ 9.28 (d, J=8.8 Hz, 1H), 8.38 (s, 1H), 8.26 (d, J=7.2 Hz, 1H), 8.21 (d, J=2.0 Hz, 1H), 8.02 (d, J=8.8 Hz, 1H), 7.18 (t, J=54 Hz, 1H), 3.52 (m, 1H), 2.51 (s, 3H), 2.32 (s, 3H), 1.6-1.2 (m, 8H). $^{19}$F NMR (DMSO) δ −116.0 (d, J=54 Hz, 2F).

Example 13

Preparation of N-cyclopropyl-7-(3,5-dimethylisoxazol-4-yl)quinoline-5-sulfonamide

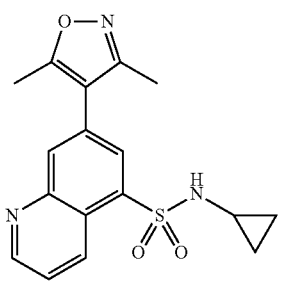 [SMILES: Cc1noc(C)c1-c1cc(S(=O)(=O)NC2CC2)c2cccnc2c1]

This compound was prepared according to the procedure in Example 3 above.

$C_{17}H_{17}N_3O_3S$. 344.1 (M+1). $^1$H NMR (DMSO) δ 9.08 (d, J=4.0 Hz, 1H), 9.06 (J=8.8 Hz, 1H), 8.49 (s, 1H), 8.33 (s, 1H), 8.16 (s, 1H), 7.77 (dd, J=8.8, 4.0 Hz, 1H), 2.52 (s, 3H), 2.33 (s, 3H), 2.18 (m, 1H), 0.45 (m, 2H), 0.31 (m, 2H).

Example 14

Preparation of N-cyclopropyl-7-(3,5-dimethylisoxazol-4-yl)-N-methylquinoline-5-sulfonamide

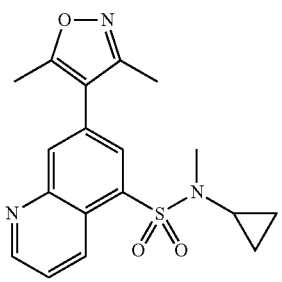 [SMILES: Cc1noc(C)c1-c1cc(S(=O)(=O)N(C)C2CC2)c2cccnc2c1]

This compound was prepared according to the procedure in Example 3 above.

$C_{18}H_{19}N_3O_3S$. 358.1 (M+1). $^1$H NMR (DMSO) δ 9.18 (d, J=8.4 Hz, 1H), 9.09 (d, J=4.4 Hz, 1H), 8.39 (s, 1H), 8.15 (s, 1H), 7.78 (dd, J=8.8, 4.0 Hz, 1H), 2.82 (s, 3H), 2.53 (s, 3H), 2.34 (s, 3H), 2.04 (m, 1H), 0.71 (m, 4H).

Example 15

Preparation of N-cyclobutyl-7-(3,5-dimethylisoxazol-4-yl)quinoline-5-sulfonamide

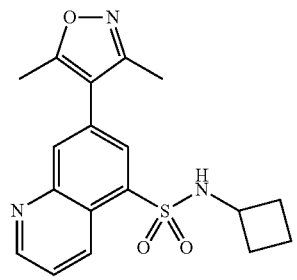 [SMILES: Cc1noc(C)c1-c1cc(S(=O)(=O)NC2CCC2)c2cccnc2c1]

This compound was prepared according to the procedure in Example 3 above.

$C_{18}H_{19}N_3O_3S$. 358.1 (M+1). $^1$H NMR (DMSO) δ 9.08 (m, 2H), 8.50 (d, J=8.4 Hz, 1H), 8.30 (s, 1H), 8.10 (s, 1H), 7.78 (dd, J=8.4, 4.0 Hz, 1H), 3.70 (m, 1H), 2.52 (s, 3H), 2.32 (s, 3H), 1.9-1.4 (m, 6H).

Example 16

Preparation of N-((3,3-difluorocyclobutyl)methyl)-7-(3,5-dimethylisoxazol-4-yl)quinoline-5-sulfonamide

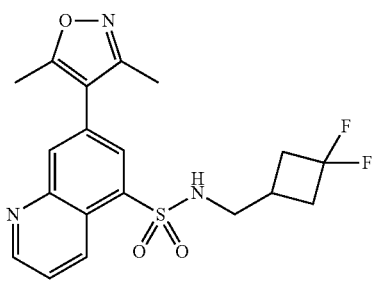 [SMILES: Cc1noc(C)c1-c1cc(S(=O)(=O)NCC2CC(F)(F)C2)c2cccnc2c1]

This compound was prepared according to the procedure in Example 3 above.

$C_{19}H_{19}F_2N_3O_3S$. 408.1 (M+1). $^1$H NMR (DMSO) δ 9.09 (d, J=4.0 Hz, 1H), 9.04 (d, J=8.4 Hz, 1H), 8.38 (t, J=6.0 Hz, 1H), 8.31 (s, 1H), 8.10 (s, 1H), 7.78 (dd, J=8.4, 4.4 Hz, 1H), 2.99 (m, 2H), 2.52 (s, 3H), 2.45 (m, 2H), 2.33 (s, 3H), 2.20 (m, 3H).

Example 17

Preparation of 7-(3,5-dimethylisoxazol-4-yl)-N-((1R,2S)-2-phenylcyclopropyl)quinoline-5-sulfonamide

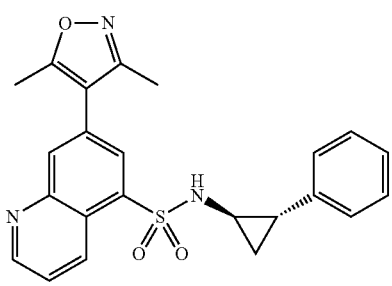 [SMILES: Cc1noc(C)c1-c1cc(S(=O)(=O)N[C@@H]2C[C@H]2c2ccccc2)c2cccnc2c1]

This compound was prepared according to the procedure in Example 3 above.

$C_{23}H_{21}N_3O_3S$. 420.1 (M+1). $^1$H NMR (DMSO) δ 9.09 (d, J=4.0 Hz, 1H), 9.02 (d, J=8.8 Hz, 1H), 8.74 (d, J=2.8 Hz, 1H), 8.31 (s, 1H), 8.03 (s, 1H), 7.71 (dd, J=8.8, 4.0 Hz, 1H), 7.08 (m, 3H), 6.69 (d, J=6.8 Hz, 2H), 2.34 (s, 3H), 2.31 (m, 1H), 2.15 (s, 3H), 1.65 (m, 1H), 1.09 (m, 2H).

Example 18

Preparation of 7-(3,5-dimethylisoxazol-4-yl)-N-((1R,2R)-2-(4-fluorophenyl)cyclopentyl)quinoline-5-sulfonamide

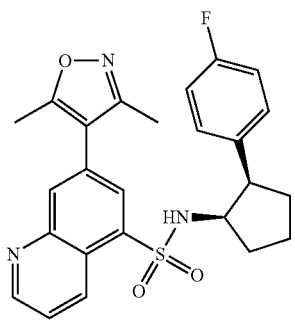

This compound was prepared according to the procedure in Example 3 above.

$C_{25}H_{24}FN_3O_3S$. 466.1 (M+1). $^1$H NMR (DMSO) δ 9.18 (d, J=8.0 Hz, 1H), 9.08 (d, J=4.4 Hz, 1H), 8.30 (s, 1H), 8.19 (d, J=J=7.6 Hz, 1H), 8.15 (s, 1H), 7.78 (dd, J=8.8, 4.0 Hz, 1H), 6.92 (m, 2H), 6.81 (m, 2H), 3.63 (m, 1H), 2.50 (s, 3H), 2.45 (m, 1H), 2.31 (s, 3H), 2.20 (m, 1H), 1.90 (m, 1H), 1.6-1.2 (m, 4H).

Example 19

Preparation of 4-((7-(3,5-dimethylisoxazol-4-yl)quinolin-5-yl)sulfonyl)piperazin-2-one

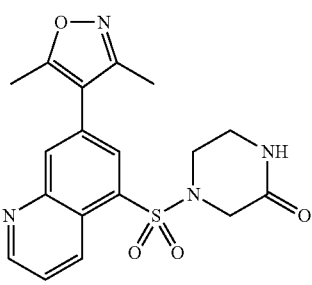 [SMILES: Cc1noc(C)c1-c1cc(S(=O)(=O)N2CCNC(=O)C2)c2cccnc2c1]

This compound was prepared according to the procedure in Example 3 above.

$C_{18}H_{18}N_4O_4S$. 387.1 (M+1). $^1$H NMR (DMSO) δ 9.10 (dd, J=4.4, 1.6 Hz, 1H), 9.04 (d, J=8.4 Hz, 1H), 8.38 (s, 1H), 8.17 (d, J=2.0 Hz, 1H), 8.07 (br, 1H), 7.78 (dd, J=8.4, 4.0 Hz, 1H), 3.74 (s, 2H), 3.47 (m, 2H), 3.21 (m, 2H), 2.53 (s, 3H), 2.34 (s, 3H).

Example 20

Preparation of N-(cyclopropylmethyl)-7-(3,5-dimethylisoxazol-4-yl)quinoline-5-sulfonamide

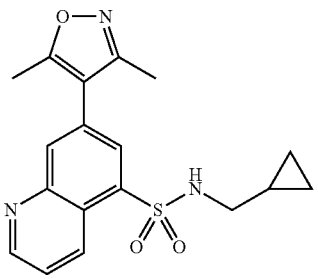 [SMILES: Cc1noc(C)c1-c1cc(S(=O)(=O)NCC2CC2)c2cccnc2c1]

This compound was prepared according to the procedure in Example 3 above.

$C_{18}H_{19}N_3O_3S$. 358.1 (M+1). $^1$H NMR (DMSO) δ 9.08 (m, 2H), 8.31 (t, J=6.0 Hz, 1H), 8.28 (s, 1H), 8.10 (s, 1H), 7.77 (m, 1H), 2.79 (m, 2H), 2.52 (s, 3H), 2.33 (s, 3H), 0.74 (m, 1H), 0.25 (m, 2H), 0.02 (m, 2H).

Example 21

Preparation of N-cyclopentyl-7-(3,5-dimethylisoxazol-4-yl)-2-methoxyquinoline-5-sulfonamide

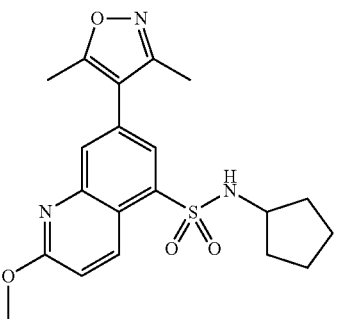 [SMILES: COc1ccc2c(S(=O)(=O)NC3CCCC3)cc(-c3c(C)noc3C)cc2n1]

This compound was prepared according to the procedure in Example 8 above.

$C_{20}H_{23}N_3O_4S$. 402.1 (M+1). NMR (DMSO) δ 8.94 (d, J=9.6 Hz, 1H), 8.12 (d, J=7.2 Hz, 1H), 8.01 (d, J=1.6 Hz, 1H), 7.92 (d, J=1.6 Hz, 1H), 7.26 (d, J=9.6 Hz, 1H), 4.04 (s, 3H), 3.51 (m, 1H), 2.51 (s, 3H), 2.30 (s, 3H), 1.6-1.2 (m, 8H).

Example 22

Preparation of 2-amino-N-cyclopentyl-7-(3,5-dimethylisoxazol-4-yl)quinoline-5-sulfonamide

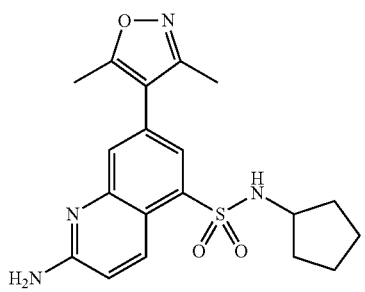 [SMILES: Cc1noc(C)c1-c1cc(S(=O)(=O)NC2CCCC2)c2ccc(N)nc2c1]

This compound was prepared according to the procedure in Example 7 above.

$C_{19}H_{22}N_4O_3S$. 387.1 (M+1). $^1$H NMR (DMSO) δ 8.82 (br, 1H), 8.14 (br, 1H), 7.79 (br, 2H), 7.14 (br, 1H), 3.52 (m, 1H), 2.52 (s, 3H), 2.30 (s, 3H), 1.6-1.2 (m, 8H).

Example 23

Preparation of 8-chloro-N-cyclopentyl-7-(3,5-dimethylisoxazol-4-yl)quinoline-5-sulfonamide

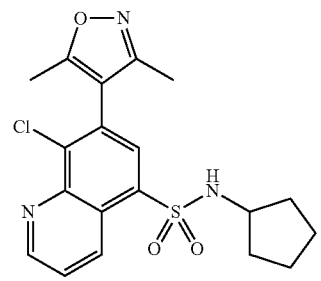

This compound was prepared according to the procedure in Example 3 above.

$C_{19}H_{20}ClN_3O_3S$. 406.5 (M+1). $^1$H NMR (DMSO) δ 9.21 (d, J=4.0 Hz, 1H), 9.16 (d, J=8.0 Hz, 1H), 8.26 (d, J=6.4 Hz, 1H), 8.06 (s, 1H), 7.91 (dd, J=8.4, 4.0 Hz, 1H), 3.53 (m, 1H), 2.34 (s, 3H), 2.14 (s, 3H), 1.6-1.2 (m, 8H).

Example 24

Preparation of 7-(3,5-dimethylisoxazol-4-yl)-N-((1S,3R)-3-hydroxycyclopentyl)quinoline-5-sulfonamide

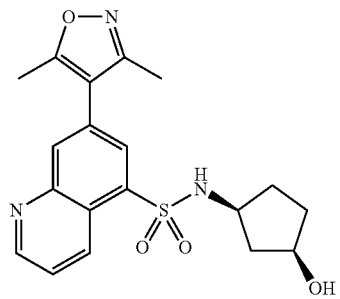 [SMILES: Cc1noc(C)c1-c1cc(S(=O)(=O)N[C@H]2CC[C@@H](O)C2)c2cccnc2c1]

This compound was prepared according to the procedure in Example 3 above.

$C_{19}H_{21}N_3O_4S$. 388.1 (M+1).

Example 25

Preparation of 7-(3,5-dimethylisoxazol-4-yl)-N-((1R,3S)-3-hydroxycyclohexyl)quinoline-5-sulfonamide

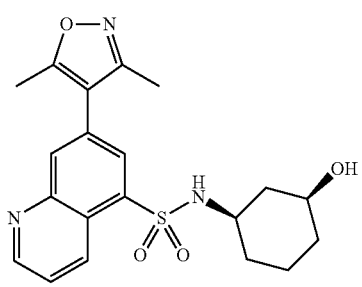 [SMILES: Cc1noc(C)c1-c1cc(S(=O)(=O)N[C@@H]2CCC[C@H](O)C2)c2cccnc2c1]

This compound was prepared according to the procedure in Example 3 above.

$C_{20}H_{23}N_3O_4S$. 402.1 (M+1).

Example 26

Preparation of 7-(3,5-dimethylisoxazol-4-yl)-N-((1r,4r)-4-hydroxycyclohexyl)quinoline-5-sulfonamide

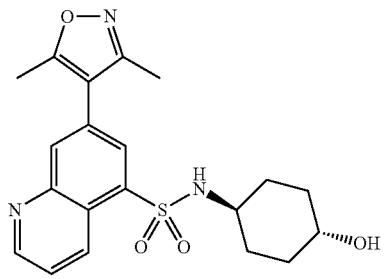 [SMILES: Cc1noc(C)c1-c1cc(S(=O)(=O)N[C@H]2CC[C@H](O)CC2)c2cccnc2c1]

This compound was prepared according to the procedure in Example 3 above.
$C_{20}H_{23}N_3O_4S$. 402.1 (M+1).

Example 27

Preparation of 7-(3,5-dimethylisoxazol-4-yl)-N-(1-methylcyclopentyl)quinoline-5-sulfonamide

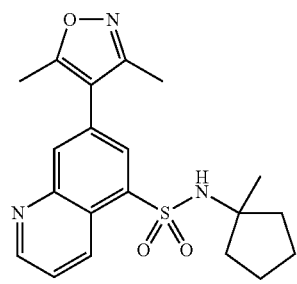 [SMILES: Cc1noc(C)c1-c1cc(S(=O)(=O)NC2(C)CCCC2)c2cccnc2c1]

This compound was prepared according to the procedure in Example 3 above.
$C_{20}H_{23}N_3O_3S$. 386.1 (M+1). $^1$H NMR (DMSO) δ 9.09 (m, 2H), 8.29 (s, 1H), 8.16 (d, J=2.0 Hz, 1H), 8.03 (s, 1H), 7.76 (dd, J=8.8, 4.0 Hz, 1H), 2.51 (s, 3H), 2.31 (s, 3H), 1.83 (m, 2H), 1.35 (m, 4H), 1.20 (s, 3H), 1.11 (m, 2H).

Example 28

Preparation of tert-butyl((1s,3s)-3-(7-(3,5-dimethyl-isoxazol-4-yl)quinoline-5-sulfonamido)cyclobutyl)carbamate

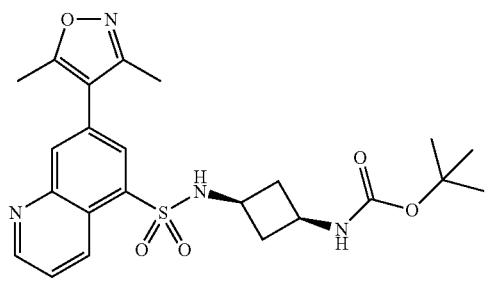 [SMILES: Cc1noc(C)c1-c1cc(S(=O)(=O)N[C@H]2C[C@@H](NC(=O)OC(C)(C)C)C2)c2cccnc2c1]

This compound was prepared according to the procedure in Example 3 above.
$C_{23}H_{28}N_4O_5S$. 473.1 (M+1).

Example 29

Preparation of N-cyclopentyl-7-(3,5-dimethylisoxazol-4-yl)-3-(1H-imidazol-1-yl)-2-oxo-1,2-dihydroquinoline-5-sulfonamide

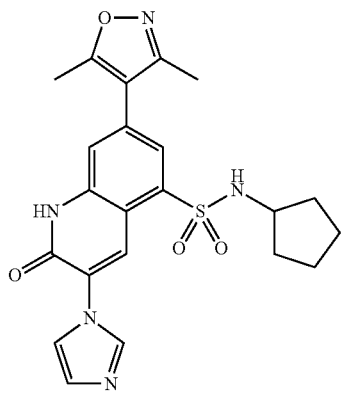 [SMILES: Cc1noc(C)c1-c1cc(S(=O)(=O)NC2CCCC2)c2cc(-n3ccnc3)c(=O)[nH]c2c1]

$C_{22}H_{23}N_5O_4S$. 454.1 (M+1). $^1$H NMR (DMSO) δ 12.96 (s, 1H), 9.15 (s, 1H), 8.80 (s, 1H), 8.30 (d, J=8.0 Hz, 1H), 8.01 (s, 1H), 7.80 (s, 1H), 7.70 (m, 2H), 3.46 (m, 1H), 2.50 (s, 3H), 2.31 (s, 3H), 1.60-1.25 (m, 8H).

Example 30

Preparation of N-cyclopentyl-7-(3,5-dimethylisoxazol-4-yl)-2-oxo-3-(1H-pyrazol-1-yl)-1,2-dihydroquinoline-5-sulfonamide

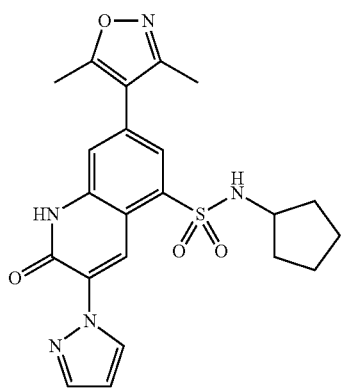 [SMILES: Cc1noc(C)c1-c1cc(S(=O)(=O)NC2CCCC2)c2cc(-n3cccn3)c(=O)[nH]c2c1]

$C_{22}H_{23}N_5O_4S$. 454.1 (M+1).

Example 31

Preparation of 7-(3,5-dimethylisoxazol-4-yl)-N-((1R,2S)-2-hydroxycyclopentyl)quinoline-5-sulfonamide

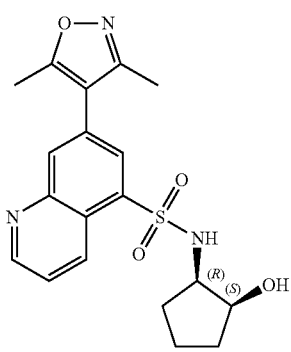

This compound was prepared according to the procedure in Example 3 above.

$C_{19}H_{21}N_3O_4S$. 388.1 (M+1). $^1$H NMR (DMSO) δ 9.12 (d, J=8 Hz, 1H), 9.02 (dd, J=4 and 2 Hz, 1H), 8.24 (s, 1H), 8.15 (d, J=2 Hz, 1H), 7.92 (d, J=8 Hz, 1H), 7.70 (dd, J=8 and 4 Hz, 1H), 3.64 (m, 1H), 3.36 (m, 1H), 2.46 (s, 3H), 2.29 (s, 3H), 1.6-1.2 (m, 7H).

Example 32

Preparation of 7-(3,5-dimethylisoxazol-4-yl)-N-((1R,2R)-2-hydroxycyclopentyl)quinoline-5-sulfonamide

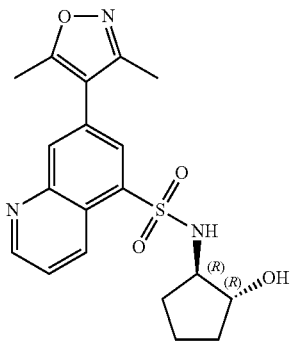

This compound was prepared according to the procedure in Example 3 above.

$C_{19}H_{21}N_3O_4S$. 388.1 (M+1). $^1$H NMR (DMSO) δ 9.07 (m, 2H), 8.27 (s, 1H), 8.20 (d, J=2 Hz, 1H), 8.10 (d, J=8 Hz, 1H), 7.74 (dd, J=8 and 4 Hz, 1H), 3.73 (m, 1H), 3.29 (m, 1H), 2.49 (s, 3H), 2.33 (s, 3H), 1.8-1.2 (m, 7H).

Example 33

Preparation of 7-(3,5-dimethylisoxazol-4-yl)-N-((1S,2R)-2-hydroxycyclopentyl)quinoline-5-sulfonamide

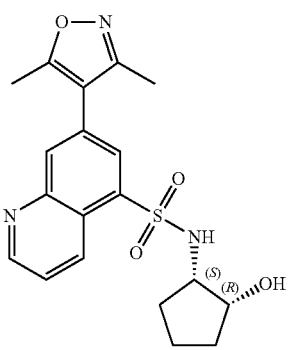

This compound was prepared according to the procedure in Example 3 above.

$C_{19}H_{21}N_3O_4S$. 388.1 (M+1). $^1$H NMR (DMSO) δ 9.12 (d, J=8 Hz, 1H), 9.03 (dd, J=4 and 2 Hz, 1H), 8.24 (d, J=1 Hz, 1H), 8.15 (d, J=2 Hz, 1H), 7.92 (d, J=8 Hz, 1H), 7.78 (dd, J=8 and 4 Hz, 1H), 3.64 (m, 1H), 3.35 (m, 1H), 2.48 (s, 3H), 2.29 (s, 3H), 1.6-1.2 (m, 7H).

Example 34

Preparation of (1R,2R)—N-cyclopentyl-2-(7-(3,5-dimethylisoxazol-4-yl)quinoline-5-sulfonamido)cyclopentanecarboxamide

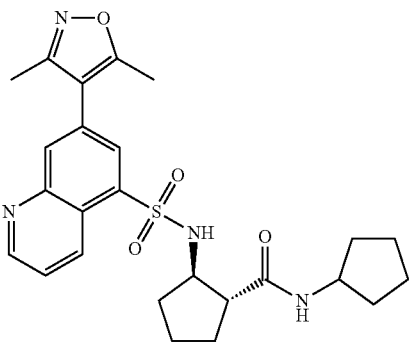 [SMILES: Cc1noc(C)c1-c1cc(S(=O)(=O)N[C@@H]2CCC[C@H]2C(=O)NC2CCCC2)c2cccnc2c1]

This compound was prepared according to the procedure in Example 3 above.

$C_{25}H_{30}N_4O_4S$. 483.1 (M+1). $^1$H NMR (DMSO) l 9.04 (m, 2H), 8.24 (m, 2H), 8.08 (d, J=2 Hz, 1H), 7.73 (dd, J=8 and 4

Hz, 1H), 7.30 (d, J=8 Hz, 1H), 3.82 (m, 1H), 3.47 (m, 1H), 2.53 (s, 3H), 2.33 (s, 3H), 1.8-0.7 (m, 15H).

Example 35

Preparation of 5-(benzylthio)-7-chloroquinoxaline

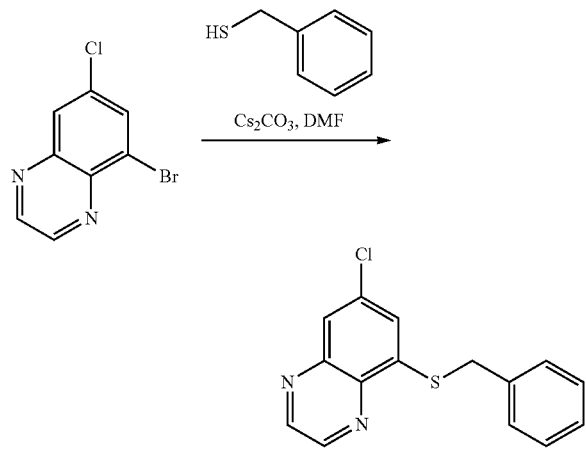

Benzyl mercaptan (0.51 g, 4.1 mmol) was added dropwise to a mixture of 5-bromo-7-chloroquinoxaline (1 g, 4.1 mmol), cesium carbonate (1.6 g, 4.92 mmol) at 0° C. in DMF (25 ml) under nitrogen. The reaction mixture was allowed to warm to room temperature, stirred for 2 hours and partitioned between ethyl acetate and water. The organic phase was washed with brine, dried with sodium sulfate and concentrated. Purification by column chromatography gave 5-(benzylthio)-7-chloroquinoxaline (rf=0.39 in 9:1 hexanes/ethyl acetate) as a yellow solid. The undesired regioisomer elutes afterwards (rf=0.27 in 9:1 hexanes/ethyl acetate).

Example 36

Preparation of 7-chloro-N-cyclopentylquinoxaline-5-sulfonamide

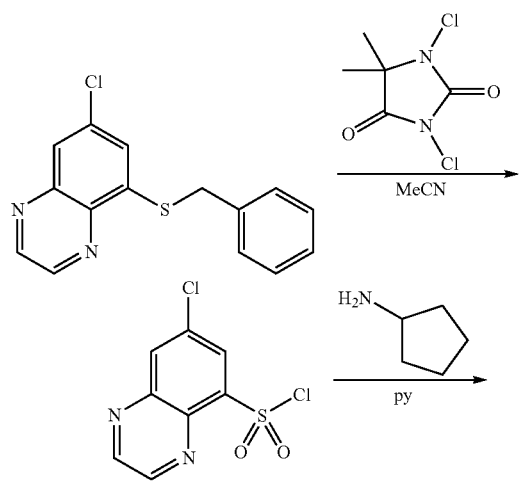

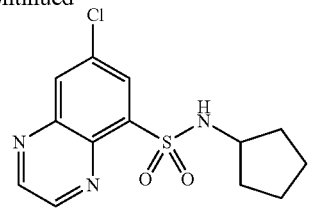

Solid 1,3-dichloro-5,5-dimethylimidazolidine-2,4-dione (0.293 g, 1.5 mmol) was added to an ice cold suspension of 5-(benzylthio)-7-chloroquinoxaline (0.214 g, 0.748 mmol) in acetonitrile (5 mL), acetic acid (0.179 mL, 2.99 mM) and water (0.053 mL, 2.99 mM). The reaction mixture was allowed to warm to room temperature and stirred for 1 hour before being partitioned between brine and ethyl acetate. The organic layer was dried using sodium sulfate and evaporated. The crude sulfonyl chloride (0.26 g, rf 0.42 in 9:1 hexanes/ethyl acetate) was used without further purification in the next step.

To a solution of cyclopentyl amine (0.134 mg, 1.6 mmol) in pyridine (5 ml) was added a solution of 7-chloroquinoxaline-5-sulfonyl chloride (0.26 g, 0.748 mmol, crude) in DCM (5 mL) at 0° C. The reaction was stirred at room temperature for 15 minutes before being partitioned between brine and ethyl acetate. The organic layer was washed with brine and dried over sodium sulfate. Purification on silica gel (rf=0.38 in 1:1 hexanes/ethyl acetate) afforded 7-chloro-N-cyclopentylquinoxaline-5-sulfonamide as an off-white powder.

Example 37

Preparation of N-cyclopentyl-7-(3,5-dimethylisoxazol-4-yl)quinoxaline-5-sulfonamide

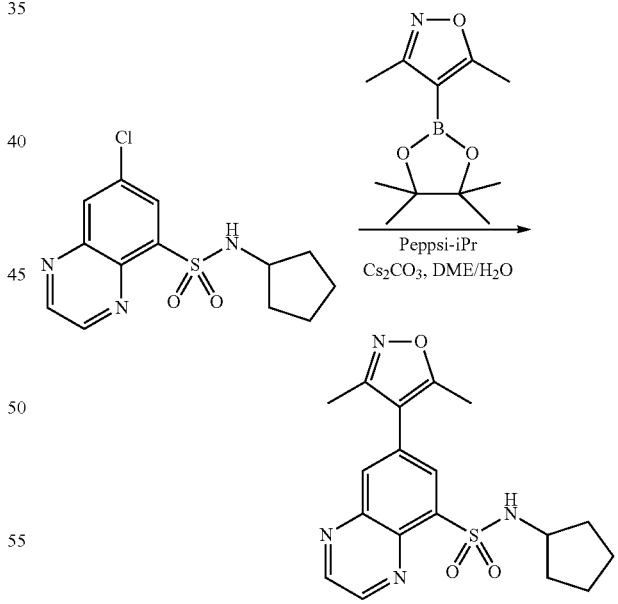

To a mixture of 7-chloro-N-cyclopentylquinoxaline-5-sulfonamide (0.07 g, 0.22 mmol), 3,5-dimethylisoxazole-4-boronic acid pinacol ester (0.15 g, 0.66 mM, Aldrich catalogue number 643882), Peppsi-iPr (0.014 g, 0.022 mM, Aldrich catalogue number 669032) and cesium carbonate (0.143 g, 0.44 mM) under nitrogen was added dimethoxyethane (3 mL) and water (1 mL). The reaction mixture was heated to 90° C. for 1 hour. The mixture is partitioned between water and ethyl acetate, the aqueous phase is discarded and the products are purified by silica gel (rf=0.36 in 1:1 hexanes/ethyl acetate) to give N-cyclopentyl-7-(3,5-dimethylisoxazol-4-yl)quinoxaline-5-sulfonamide as an off-white solid.

C₁₈H₂₀N₄O₃S. 373.1 (M+1). ¹H NMR (CDCl₃) δ 9.02 (d, J=1.7 Hz, 1H), 8.98 (d, J=1.7 Hz, 1H), 8.43 (d, J=2.4 Hz, 1H), 8.21 (d, J=1.7 Hz, 1H), 5.80 (d, J=6.4 Hz, 1H), 3.65 (m, 1H), 2.55 (s, 3H), 2.41 (s, 3H), 1.72-1.44 (m, 8H).

Example 38

Preparation of 5-(N-cyclopentylsulfamoyl)-7-(3,5-dimethylisoxazol-4-yl)quinoxaline 1-oxide

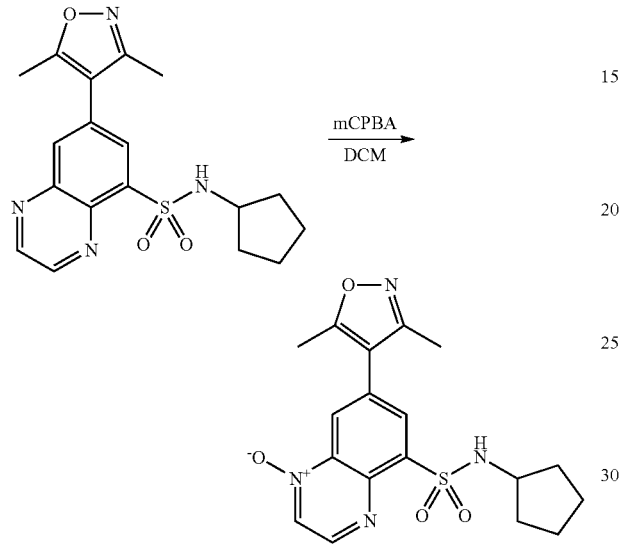

A mixture of N-cyclopentyl-7-(3,5-dimethylisoxazol-4-yl)quinoxaline-5-sulfonamide (0.069 g, 0.18 mmol) and mCPBA (max 77% by weight, 0.083 g, 0.37 mM) in dichloromethane (3 mL) was stirred at room temperature for 2 hours. Additional mCPBA (0.166 g, 0.74 mM) was added and the reaction stirred for 16 hours at room temperature. Volatiles were removed under reduced pressure and the crude product purified by preparatory HPLC (5-95% MeCN/H₂O, 0.1% TFA) to afford the product as a white solid.

C₁₈H₂₀N₄O₄S. 387.5 (M−1). ¹H NMR (CDCl₃) δ 9.04 (d, J=1.8 Hz, 1H), 8.96 (d, J=1.8 Hz, 1H), 8.43 (d, J=1.5 Hz, 1H), 8.23 (d, J=1.5 Hz, 1H), 5.84 (d, J=6.6 Hz, 1H), 3.65 (m, 1H), 2.56 (s, 3H), 2.43 (s, 3H), 1.72-1.28 (m, 8H).

Example 39

Preparation of N-cyclopentyl-7-(3,5-dimethylisoxazol-4-yl)-2-oxo-1,2-dihydroquinoxaline-5-sulfonamide

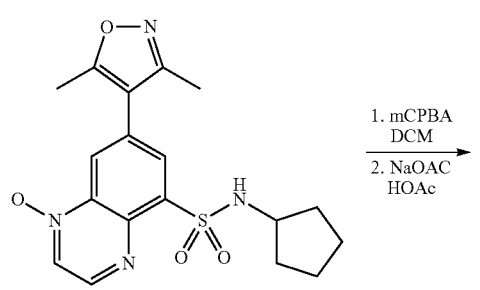

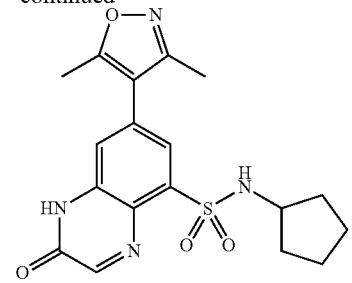

5-(N-cyclopentylsulfamoyl)-7-(3,5-dimethylisoxazol-4-yl)quinoxaline 1-oxide was dissolved in POCl₃ and heated to reflux for 1 hour. After cooling to room temperature, volatiles were removed under reduced pressure and dissolved in acetic acid (4 ml). Sodium acetate (100 mg) was added and the solution stirred for 4 hours. Volatiles were removed under reduced pressure and the crude product was purified by preparatory HPLC (5-95% MeCN/H₂O, 0.1% TFA) to afford the product as a white solid.

C₁₈H₂₀N₄O₄S. 389.02 (M+1). ¹H NMR (CDCl₃) δ 8.17 (s, 1H), 7.81 (s, 1H), 7.50 (s, 1H), 5.95 (d, J=7.2 Hz, 1H), 3.61 (q, J=6.4 Hz, 1H), 2.49 (s, 3H), 2.34 (s, 3H), 1.78-1.27 (m, 8H).

Example 40

Preparation of N-cyclopentyl-7-(3,5-dimethylisoxazol-4-yl)-2-oxo-3-(pyridin-3-yl)-1,2-dihydroquinoline-5-sulfonamide

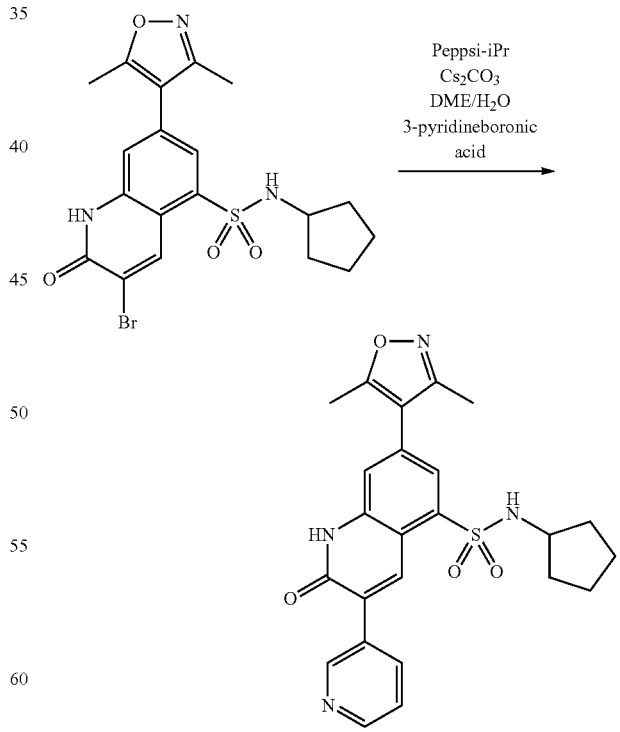

A mixture of 3-bromo-N-cyclopentyl-7-(3,5-dimethylisoxazol-4-yl)-2-oxo-1,2-dihydroquinoline-5-sulfonamide (45 mg, 0.1 mmol), 3-pyridine boronic acid (25 mg, 0.2 mmol), cesium carbonate (100 mg, 0.3 mmol), Peppsi-iPr (4 mg, 5 mol %), dimethoxyethane (2 mL) and water (1 mL) was stirred at 100° C. for 2 hours. The reaction mixture was concentrated before being purified by preparative HPLC to give N-cyclopentyl-7-(3,5-dimethylisoxazol-4-yl)-2-oxo-3-(pyridin-3-yl)-1,2-dihydroquinoline-5-sulfonamide as a yellow powder.

$C_{24}H_{24}N_4O_4S$. 465.1 (M+1).

Example 41

Preparation of N-cyclopentyl-7-(3,5-dimethylisoxazol-4-yl)-3-((2-morpholinoethyl)amino)-2-oxo-1,2-dihydroquinoline-5-sulfonamide

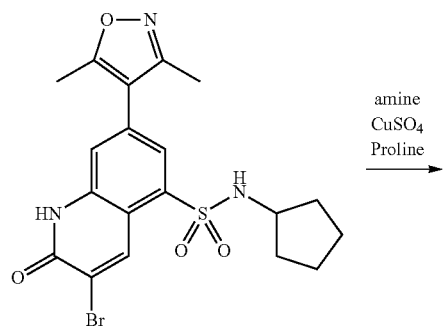

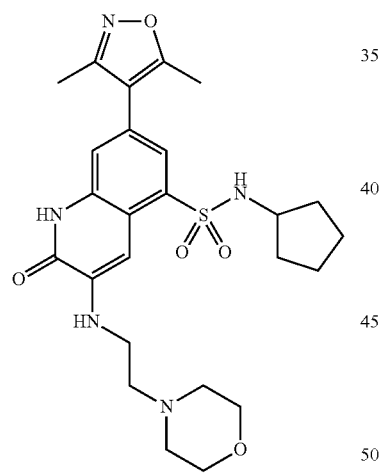

A mixture of 3-bromo-N-cyclopentyl-7-(3,5-dimethylisoxazol-4-yl)-2-oxo-1,2-dihydroquinoline-5-sulfonamide (20 mg, 0.04 mmol), 2-morpholinoethanamine (0.2 mL), CuSO$_4$ (7 mg, 1 equiv), proline (5 mg, 1 equiv) and methoxyethanol (1 mL) was stirred at 130° C. for 2 hours. The reaction mixture was cooled and purified by preparative HPLC to give N-cyclopentyl-7-(3,5-dimethylisoxazol-4-yl)-3-(2-morpholinoethylamino)-2-oxo-1,2-dihydroquinoline-5-sulfonamide, TFA salt as a pale yellow powder.

$C_{25}H_{33}N_5O_5S$. 516.1 (M+1). $^1$H NMR (DMSO) δ 12.29 (s, 1H), 9.60 (br, 1H), 7.98 (d, J=7.2 Hz, 1H), 7.62 (s, 1H), 7.47 (s, 1H), 7.17 (s, 1H), 6.69 (br, 1H), 4.1-3.1 (m, 13H), 2.44 (s, 3H), 2.25 (s, 3H), 1.6-1.3 (m, 8H).

Example 42

Preparation of N-cyclopentyl-7-(3,5-dimethylisoxazol-4-yl)-3-(4-fluorophenyl)-2-oxo-1,2-dihydroquinoline-5-sulfonamide

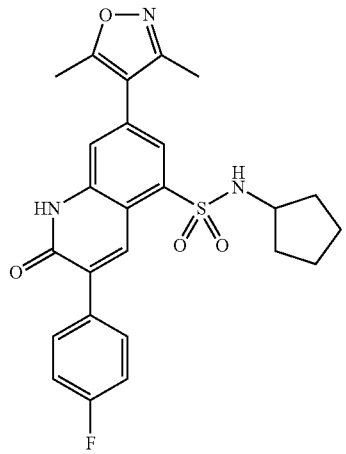 [SMILES: Cc1noc(C)c1-c1cc(S(=O)(=O)NC2CCCC2)c2cc(-c3ccc(F)cc3)c(=O)[nH]c2c1]

This compound was prepared according to the procedure in Example 40 above.

$C_{25}H_{24}FN_3O_4S$. 482.1 (M+1).

Example 43

Preparation of N-cyclopentyl-7-(3,5-dimethylisoxazol-4-yl)-2-oxo-3-(pyridin-3-yl)-1,2-dihydroquinoline-5-sulfonamide

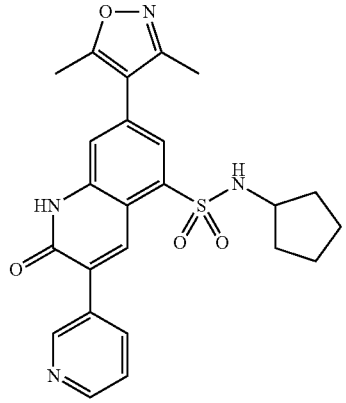 [SMILES: Cc1noc(C)c1-c1cc(S(=O)(=O)NC2CCCC2)c2cc(-c3cccnc3)c(=O)[nH]c2c1]

This compound was prepared according to the procedure in Example 40 above.

$C_{24}H_{24}N_4O_4S$. 465.1 (M+1). $^1$H NMR (DMSO) δ 12.44 (s, 1H), 8.98 (s, 1H), 8.78 (s, 1H), 8.67 (d, J=4.0 Hz, 1H), 8.30

(m, 2H), 7.72 (s, 1H), 7.64 (s, 1H), 7.61 (m, 1H), 3.52 (m, 1H), 2.51 (s, 3H), 2.33 (s, 3H), 1.7-1.2 (m, 8H).

Example 44

Preparation of N-cyclopentyl-3-(1,2-dimethyl-1H-imidazol-5-yl)-7-(3,5-dimethylisoxazol-4-yl)-2-oxo-1,2-dihydroquinoline-5-sulfonamide

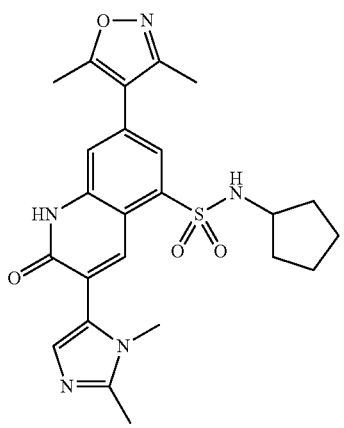 [SMILES: Cc1noc(C)c1-c1cc(S(=O)(=O)NC2CCCC2)c2cc(-c3cnc(C)n3C)c(=O)[nH]c2c1]

This compound was prepared according to the procedure in Example 40 above.

$C_{24}H_{27}N_5O_4S$. 482.1 (M+1).

Example 45

Preparation of N-cyclopentyl-7-(3,5-dimethylisoxazol-4-yl)-2-oxo-3-(pyridin-2-yl)-1,2-dihydroquinoline-5-sulfonamide

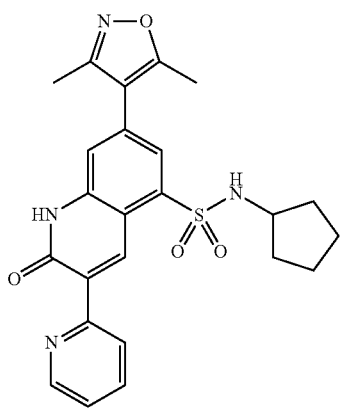 [SMILES: Cc1noc(C)c1-c1cc(S(=O)(=O)NC2CCCC2)c2cc(-c3ccccn3)c(=O)[nH]c2c1]

This compound was prepared according to the procedure in Example 40 above.

$C_{24}H_{24}N_4O_4S$. 465.1 (M+1).

Example 46

Preparation of N-cyclopentyl-7-(3,5-dimethylisoxazol-4-yl)-2-oxo-3-(pyrimidin-2-yl)-1,2-dihydroquinoline-5-sulfonamide

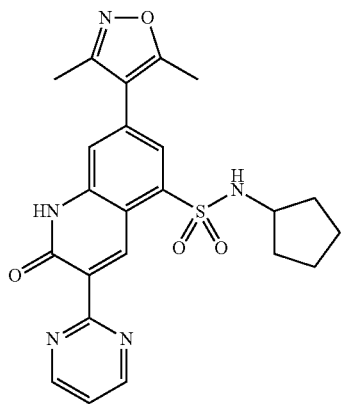 [SMILES: Cc1noc(C)c1-c1cc(S(=O)(=O)NC2CCCC2)c2cc(-c3ncccn3)c(=O)[nH]c2c1]

This compound was prepared according to the procedure in Example 40 above.

$C_{23}H_{23}N_5O_4S$. 466.1 (M+1).

Example 47

Preparation of N-((1S,2S,4R)-bicyclo[2.2.1]heptan-2-yl)-7-(3,5-dimethylisoxazol-4-yl)quinoline-5-sulfonamide

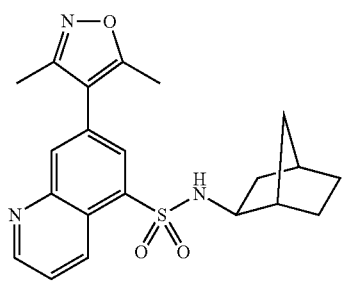 [SMILES: Cc1noc(C)c1-c1cc(S(=O)(=O)NC2CC3CCC2C3)c2cccnc2c1]

This compound was prepared according to the procedure in Example 3 above.

$C_{21}H_{23}N_3O_3S$. 398.1 (M+1).

Example 48

Preparation of N-(3,3-dimethylcyclopentyl)-7-(3,5-dimethylisoxazol-4-yl)quinoline-5-sulfonamide

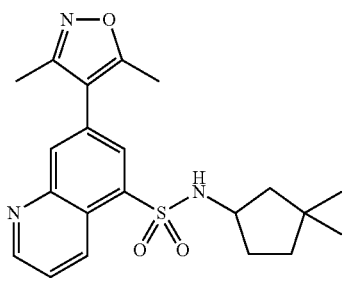 [SMILES: Cc1noc(C)c1-c1cc(S(=O)(=O)NC2CCC(C)(C)C2)c2cccnc2c1]

This compound was prepared according to the procedure in Example 3 above.

$C_{21}H_{25}N_3O_3S$. 400.1 (M+1).

Example 49

Preparation of 7-(3,5-dimethylisoxazol-4-yl)-N-(8-methyl-8-azabicyclo[3.2.1]octan-3-yl)quinoline-5-sulfonamide

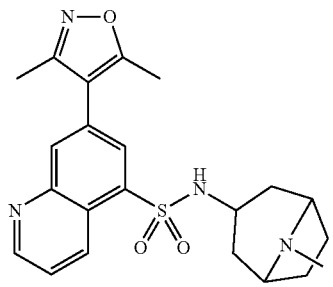 [SMILES: Cc1noc(C)c1-c1cc(S(=O)(=O)NC2CC3CCC(C2)N3C)c2cccnc2c1]

This compound was prepared according to the procedure in Example 3 above.

$C_{22}H_{26}N_4O_3S$. 427.1 (M+1).

Example 50

Preparation of 3-amino-N-cyclopentyl-7-(3,5-dimethylisoxazol-4-yl)-2-oxo-1,2-dihydroquinoline-5-sulfonamide

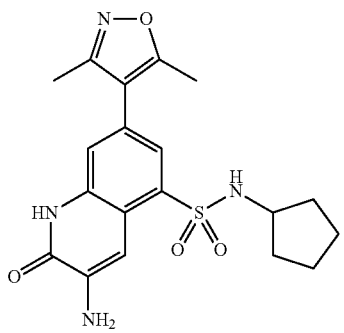 [SMILES: Cc1noc(C)c1-c1cc(S(=O)(=O)NC2CCCC2)c2cc(N)c(=O)[nH]c2c1]

This compound was prepared according to the procedure in Example 41 above.

$C_{19}H_{22}N_4O_4S$. 403.1 (M+1). $^1$H NMR (DMSO) δ 12.11 (s, 1H), 7.75 (d, J=7.2 Hz, 1H), 7.54 (m, 2H), 7.43 (s, 1H), 5.95 (br, 2H), 3.53 (m, 1H), 2.43 (s, 3H), 2.25 (s, 3H), 1.7-1.3 (m, 8H).

Example 51

Preparation of N-cyclopentyl-7-(3,5-dimethylisoxazol-4-yl)-3-morpholino-2-oxo-1,2-dihydroquinoline-5-sulfonamide

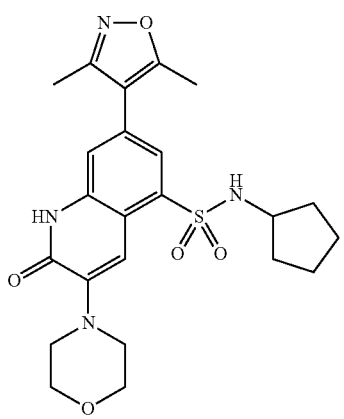 [SMILES: Cc1noc(C)c1-c1cc(S(=O)(=O)NC2CCCC2)c2cc(N3CCOCC3)c(=O)[nH]c2c1]

This compound was prepared according to the procedure in Example 41 above.

$C_{23}H_{28}N_4O_5S$. 473.1 (M+1).

Example 52

Preparation of N-cyclopentyl-7-(3,5-dimethylisoxazol-4-yl)-2-oxo-3-(piperazin-1-yl)-1,2-dihydroquinoline-5-sulfonamide

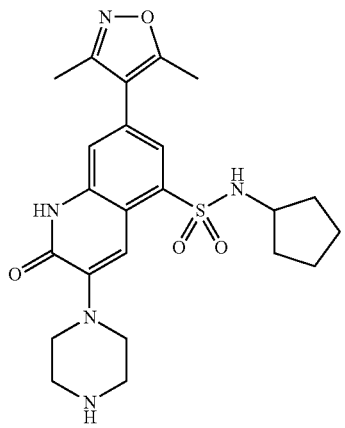 [SMILES: Cc1noc(C)c1-c1cc(S(=O)(=O)NC2CCCC2)c2cc(N3CCNCC3)c(=O)[nH]c2c1]

This compound was prepared according to the procedure in Example 41 above.

$C_{23}H_{29}N_5O_5S$. 472.1 (M+1). $^1$H NMR (DMSO) δ 12.25 (s, 1H), 8.75 (br, 2H), 8.12 (d, J=7.2 Hz, 1H), 7.75 (s, 1H), 7.64 (s, 1H), 7.53 (s, 1H), 3.6-3.6 (m, 9H), 2.46 (s, 3H), 2.26 (s, 3H), 1.6-1.3 (m, 8H).

Example 53

Preparation of N-cyclopentyl-7-(3,5-dimethylisoxazol-4-yl)-3-((2-hydroxyethyl)amino)-2-oxo-1,2-dihydroquinoline-5-sulfonamide

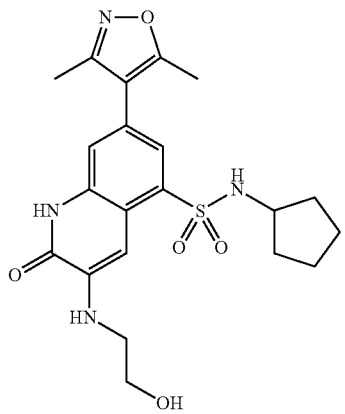 [SMILES: Cc1noc(C)c1-c1cc(S(=O)(=O)NC2CCCC2)c2cc(NCCO)c(=O)[nH]c2c1]

This compound was prepared according to the procedure in Example 41 above.

$C_{21}H_{26}N_4O_5S$. 447.1 (M+1). $^1$H NMR (DMSO) δ 12.20 (s, 1H), 7.93 (d, J=7.2 Hz, 1H), 7.60 (s, 1H), 7.45 (s, 1H), 7.16 (s,

1H), 6.12 (br, 1H), 3.68 (t, J=6.4 Hz, 2H), 3.50-3.30 (m, 3H), 2.44 (s, 3H), 2.25 (s, 3H), 1.60-1.20 (m, 8H).

Example 54

Preparation of N-cyclopentyl-7-(3,5-dimethylisoxazol-4-yl)-3-((2-methoxyethyl)amino)-2-oxo-1,2-dihydroquinoline-5-sulfonamide

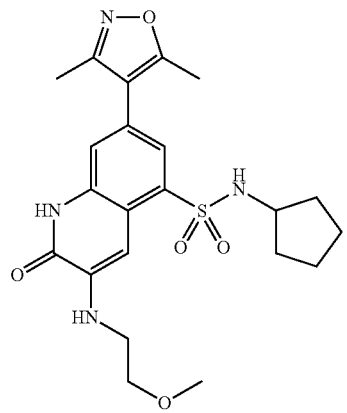 [SMILES: COCCNc1cc2c(S(=O)(=O)NC3CCCC3)cc(-c3c(C)noc3C)cc2[nH]c1=O]

This compound was prepared according to the procedure in Example 41 above.

$C_{22}H_{28}N_4O_5S$. 461.1 (M+1). $^1$H NMR (DMSO) δ 12.20 (s, 1H), 7.95 (d, J=7.2 Hz, 1H), 7.60 (d, J=1.6 Hz, 1H), 7.44 (d, J=1.6 Hz, 1H), 7.17 (s, 1H), 6.06 (t, J=5.6 Hz, 1H), 3.60 (t, J=6.0 Hz, 2H), 3.44 (m, 3H), 3.30 (s, 3H), 2.42 (s, 3H), 2.23 (s, 3H), 1.6-1.2 (m, 8H).

Example 55

Preparation of N-cyclopentyl-7-(3,5-dimethylisoxazol-4-yl)-2-oxo-3-(pyrrolidin-1-yl)-1,2-dihydroquinoline-5-sulfonamide

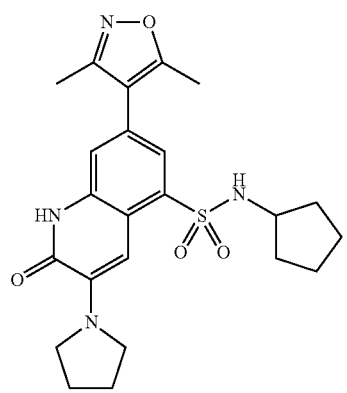 [SMILES: Cc1noc(C)c1-c1cc(S(=O)(=O)NC2CCCC2)c2cc(N3CCCC3)c(=O)[nH]c2c1]

This compound was prepared according to the procedure in Example 41 above.

$C_{23}H_{28}N_4O_4S$. 457.1 (M+1).

Example 56

Preparation of N-cyclopentyl-7-(3,5-dimethylisoxazol-4-yl)-2-oxo-3-(piperidin-1-yl)-1,2-dihydroquinoline-5-sulfonamide

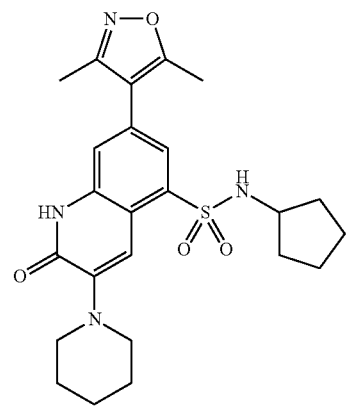 [SMILES: Cc1noc(C)c1-c1cc(S(=O)(=O)NC2CCCC2)c2cc(N3CCCCC3)c(=O)[nH]c2c1]

This compound was prepared according to the procedure in Example 41 above.

$C_{24}H_{30}N_4O_4S$. 471.1 (M+1).

Example 57

Preparation of N-cyclopentyl-3-(dimethylamino)-7-(3,5-dimethylisoxazol-4-yl)-2-oxo-1,2-dihydroquinoline-5-sulfonamide

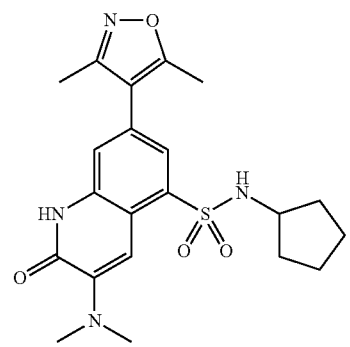 [SMILES: Cc1noc(C)c1-c1cc(S(=O)(=O)NC2CCCC2)c2cc(N(C)C)c(=O)[nH]c2c1]

This compound was prepared according to the procedure in Example 41 above.

$C_{21}H_{26}N_4O_4S$. 431.1 (M+1).

Example 58

Preparation of N-cyclopentyl-7-(3,5-dimethylisoxazol-4-yl)-3-(methylamino)-2-oxo-1,2-dihydroquinoline-5-sulfonamide

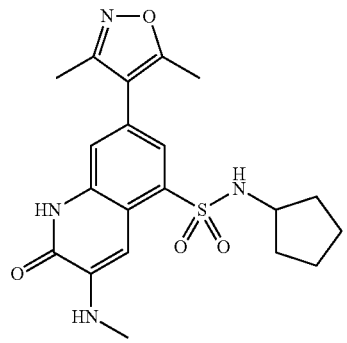 [SMILES: CNc1cc2c(S(=O)(=O)NC3CCCC3)cc(-c3c(C)noc3C)cc2[nH]c1=O]

This compound was prepared according to the procedure in Example 41 above.

$C_{20}H_{24}N_4O_4S$. 417.1 (M+1).

Example 59

Preparation of N-cyclopentyl-7-(3,5-dimethylisoxazol-4-yl)-2-oxo-3-(2-oxooxazolidin-3-yl)-1,2-dihydroquinoline-5-sulfonamide

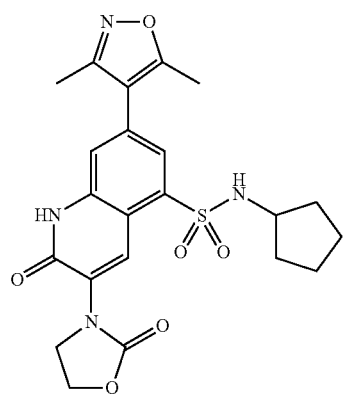 [SMILES: Cc1noc(C)c1-c1cc(S(=O)(=O)NC2CCCC2)c2cc(N3CCOC3=O)c(=O)[nH]c2c1]

$C_{22}H_{24}N_4O_6S$. 473.1 (M+1).

Example 60

Preparation of N-cyclopentyl-7-(3,5-dimethylisoxazol-4-yl)-3-(4-methylpiperazin-1-yl)-2-oxo-1,2-dihydroquinoline-5-sulfonamide

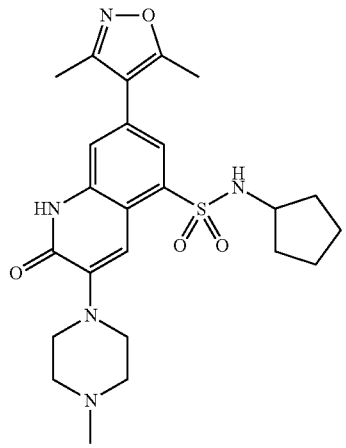 [SMILES: Cc1noc(C)c1-c1cc(S(=O)(=O)NC2CCCC2)c2cc(N3CCN(C)CC3)c(=O)[nH]c2c1]

This compound was prepared according to the procedure in Example 41 above.

$C_{24}H_{31}N_5O_4S$. 486.1 (M+1).

Example 61

Preparation of N-cyclopentyl-7-(3,5-dimethylisoxazol-4-yl)-3-((1-methylpiperidin-4-yl)amino)-2-oxo-1,2-dihydroquinoline-5-sulfonamide

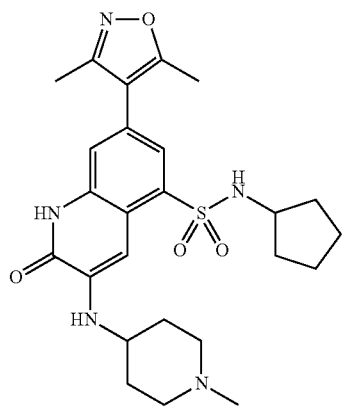 [SMILES: Cc1noc(C)c1-c1cc(S(=O)(=O)NC2CCCC2)c2cc(NC3CCN(C)CC3)c(=O)[nH]c2c1]

This compound was prepared according to the procedure in Example 41 above.

$C_{25}H_{33}N_5O_4S$. 500.1 (M+1). $^1$H NMR (DMSO) ~2.5:1 mixture of syn/anti isomers of TFA salt. Major isomer: δ 12.30 (s, 1), 9.60 (br, 1H), 7.88 (d, J=7.2 Hz, 1H), 7.60 (s, 1H), 7.46 (s, 1H), 7.24 (s, 1H), 6.25 (br, 1H), 2.82 (m, 3H), 2.44 (s, 3H), 2.25 (s, 3H), 4.0-3.0, 2.3-1.2, (m, 18H).

Example 62

Preparation of N-cyclopentyl-7-(3,5-dimethylisoxazol-4-yl)-2-oxo-3-((pyridin-3-ylmethyl)amino)-1,2-dihydroquinoline-5-sulfonamide

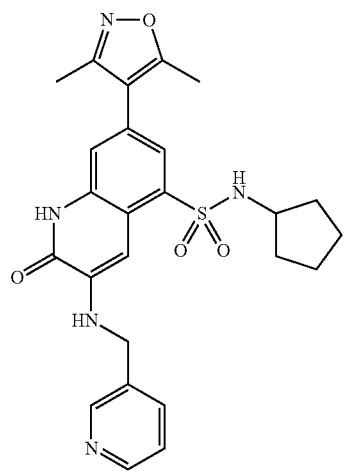 [SMILES: Cc1noc(C)c1-c1cc(S(=O)(=O)NC2CCCC2)c2cc(NCc3cccnc3)c(=O)[nH]c2c1]

This compound was prepared according to the procedure in Example 41 above.

$C_{25}H_{27}N_5O_4S$. 494.1 (M+1).

Example 63

Preparation of N-cyclopropyl-7-(3,5-dimethylisoxazol-4-yl)-2-oxo-1,2-dihydroquinoline-5-sulfonamide

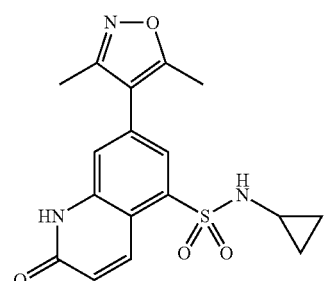

This compound was prepared according to the procedure in Example 9 above.

$C_{17}H_{17}N_3O_4S$. 360.1 (M+1).

Example 64

Preparation of 5-(N-cyclopentylsulfamoyl)-7-(3,5-dimethylisoxazol-4-yl)-2-oxo-1,2-dihydroquinoline-3-carboxamide

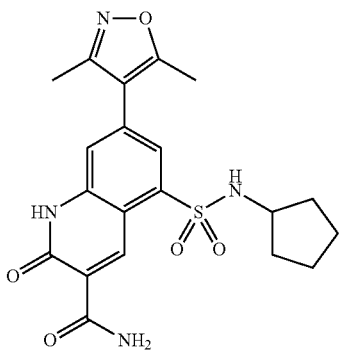 [SMILES: Cc1noc(C)c1-c1cc(S(=O)(=O)NC2CCCC2)c2cc(C(N)=O)c(=O)[nH]c2c1]

$C_{20}H_{22}N_4O_5S$. 431.1 (M+1).

Example 65

Preparation of 5-(N-cyclopentylsulfamoyl)-7-(3,5-dimethylisoxazol-4-yl)-2-oxo-1,2-dihydroquinoline-3-carboxylic acid

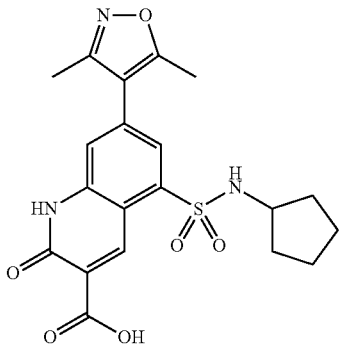 [SMILES: Cc1noc(C)c1-c1cc(S(=O)(=O)NC2CCCC2)c2cc(C(=O)O)c(=O)[nH]c2c1]

$C_{20}H_{21}N_3O_6S$. 432.1 (M+1).

Example 66

Preparation of 5-(N-cyclopentylsulfamoyl)-7-(3,5-dimethylisoxazol-4-yl)-N,N-dimethyl-2-oxo-1,2-dihydroquinoline-3-carboxamide

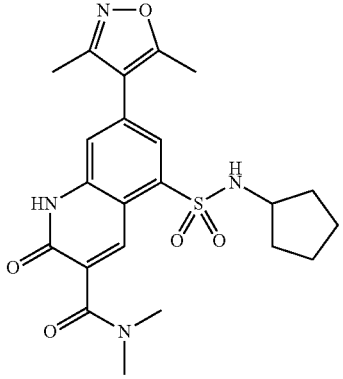 [SMILES: Cc1noc(C)c1-c1cc(S(=O)(=O)NC2CCCC2)c2cc(C(=O)N(C)C)c(=O)[nH]c2c1]

$C_{22}H_{26}N_4O_5S$. 459.1 (M+1).

Example 67

Preparation of N-cyclopentyl-3-((cyclopropylmethyl)amino)-7-(3,5-dimethylisoxazol-4-yl)-2-oxo-1,2-dihydroquinoline-5-sulfonamide

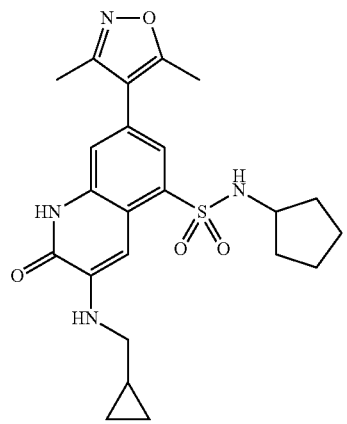 [SMILES: Cc1noc(C)c1-c1cc(S(=O)(=O)NC2CCCC2)c2cc(NCC3CC3)c(=O)[nH]c2c1]

This compound was prepared according to the procedure in Example 41 above.

$C_{23}H_{28}N_4O_4S$. 457.1 (M+1).

Example 68

Preparation of N-cyclopentyl-7-(3,5-dimethylisoxazol-4-yl)-3-(isopropylamino)-2-oxo-1,2-dihydroquinoline-5-sulfonamide

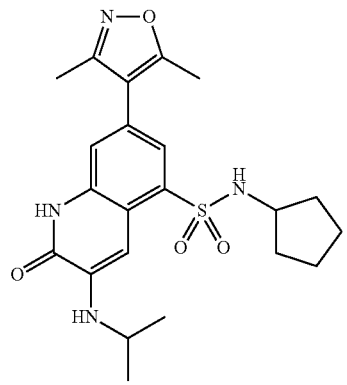 [SMILES: Cc1noc(C)c1-c1cc(S(=O)(=O)NC2CCCC2)c2cc(NC(C)C)c(=O)[nH]c2c1]

This compound was prepared according to the procedure in Example 41 above.

$C_{22}H_{28}N_4O_4S$. 445.1 (M+1).

Example 69

Preparation of 3-((2-aminoethyl)amino)-N-cyclopentyl-7-(3,5-dimethylisoxazol-4-yl)-2-oxo-1,2-dihydroquinoline-5-sulfonamide

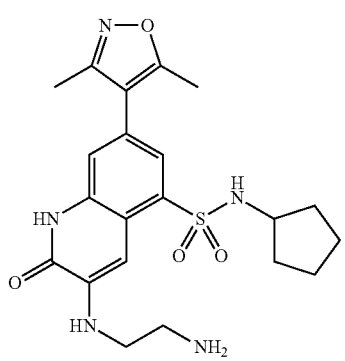 [SMILES: Cc1noc(C)c1-c1cc(S(=O)(=O)NC2CCCC2)c2cc(NCCN)c(=O)[nH]c2c1]

This compound was prepared according to the procedure in Example 41 above.

$C_{21}H_{27}N_5O_4S$. 446.1 (M+1). $^1$H NMR (DMSO) δ 12.27 (s, 1H), 7.97 (d, J=7.2 Hz, 1H), 7.81 (br, 3H), 7.61 (s, 1H), 7.47 (s, 1H), 7.16 (s, 1H), 6.55 (br, 1H), 3.49 (m, 3H), 3.15 (m, 2H), 2.44 (s, 3H), 2.25 (s, 3H), 1.6-1.3 (m, 8H).

Example 70

Preparation of N-cyclopentyl-3-((2,2-difluoroethyl)amino)-7-(3,5-dimethylisoxazol-4-yl)-2-oxo-1,2-dihydroquinoline-5-sulfonamide

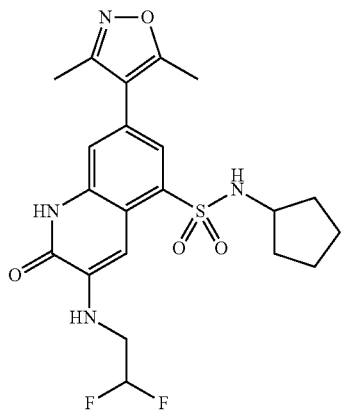 [SMILES: Cc1noc(C)c1-c1cc(S(=O)(=O)NC2CCCC2)c2cc(NCC(F)F)c(=O)[nH]c2c1]

This compound was prepared according to the procedure in Example 41 above.

$C_{21}H_{24}F_2N_4O_4S$. 467.1 (M+1).

Example 71

Preparation of 7-(3,5-dimethylisoxazol-4-yl)-N-((1R, 2R)-2-hydroxycyclopentyl)-2-oxo-1,2-dihydroquinoline-5-sulfonamide

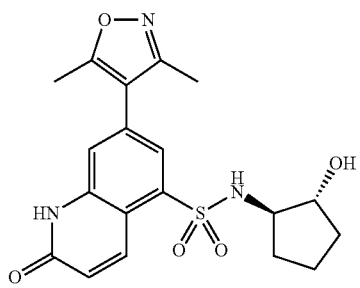 [SMILES: Cc1noc(C)c1-c1cc(S(=O)(=O)N[C@@H]2CCC[C@H]2O)c2ccc(=O)[nH]c2c1]

This compound was prepared according to the procedure in Example 9 above.

$C_{19}H_{21}N_3O_5S$. 404.1 (M+1).

Example 72

Preparation of 7-(3,5-dimethylisoxazol-4-yl)-N-((1R, 2R)-2-hydroxycyclopentyl)-3-((2-methoxyethyl)amino)-2-oxo-1,2-dihydroquinoline-5-sulfonamide

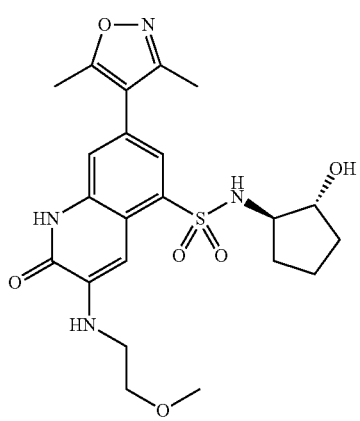 [SMILES: COCCNc1cc2c(S(=O)(=O)N[C@@H]3CCC[C@H]3O)cc(-c3c(C)noc3C)cc2[nH]c1=O]

This compound was prepared according to the procedure in Example 41 above.

$C_{22}H_{28}N_4O_6S$. 477.1 (M+1). $^1$H NMR (DMSO) δ 12.21 (s, 1H), 7.91 (d, J=7.2 Hz, 1H), 7.64 (s, 1H), 7.45 (s, 1H), 7.18 (s, 1H), 6.06 (br, 1H), 4.60 (br, 1H), 3.76 (m, 1H), 3.60 (m, 2H), 3.5-3.2 (m, 6H), 2.44 (s, 3H), 2.25 (s, 3H), 1.8-1.2 (m, 6H).

Example 73

Preparation of N-cyclopentyl-3-((2-(dimethylamino)ethyl)amino)-7-(3,5-dimethylisoxazol-4-yl)-2-oxo-1,2-dihydroquinoline-5-sulfonamide

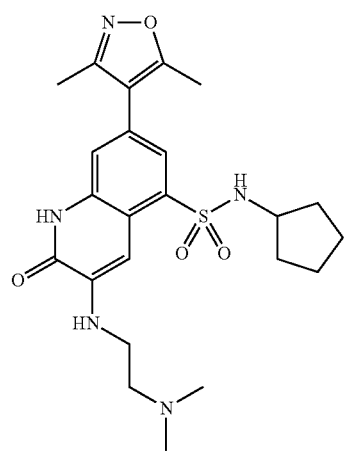 [SMILES: Cc1noc(C)c1-c1cc(S(=O)(=O)NC2CCCC2)c2cc(NCCN(C)C)c(=O)[nH]c2c1]

This compound was prepared according to the procedure in Example 41 above.

$C_{23}H_{31}N_5O_4S$. 474.1 (M+1). $^1$H NMR (DMSO) δ 12.28 (s, 1H), 9.34 (br, 1H), 8.0 (m, 1H), 7.62 (s, 1H), 7.47 (s, 1H), 7.16 (s, 1H), 6.70 (t, J=6.0 Hz, 1H), 3.7-3.2 (m, 5H), 2.85 (m, 6H), 2.44 (s, 3H), 2.25 (s, 3H), 1.6-1.3 (m, 8H).

Example 74

Preparation of N-cyclopentyl-7-(3,5-dimethylisoxazol-4-yl)-2-oxo-3-((2-(pyrrolidin-1-yl)ethyl)amino)-1,2-dihydroquinoline-5-sulfonamide

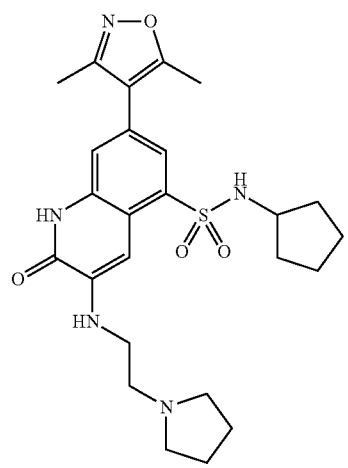 [SMILES: Cc1noc(C)c1-c1cc(S(=O)(=O)NC2CCCC2)c2cc(NCCN3CCCC3)c(=O)[nH]c2c1]

This compound was prepared according to the procedure in Example 41 above.

$C_{25}H_{33}N_5O_4S$. 500.1 (M+1).

Example B1

$K_d$ Determination of Inhibitors Binding to BRD4 Domain 1 and Domain 2

The binding of small molecule inhibitors to either BRD4 domain 1 or domain 2 were determined using the Epic, high-throughput, label-free platform (Corning, Lowell, Mass.). The Epic instrument incorporates an evanescent waveguide sensor within each well of its proprietary 384-well microplates. Direct binding of inhibitors to BRD4 immobilized onto the microplate well surface can be detected by exposing the waveguide to a broadband light source. The resulting resonant wavelength shift (measured in picometers (pm)) is proportional to the mass bound to the surface. Epic biochemical plates (Corning, Lowell, Mass.) were activated by adding 15 μl/well of 200 mM EDC and 50 mM Sulfo-NHS (Pierce Thermo Scientific, Rockford, Ill.) and incubated for 60 minutes at room temperature. Plates were washed three times with MilliQ water and dried by centrifugation (1 minute at 400 rpm). BRD4 immobilization was accomplished by resuspending the protein at a concentration of 150 μg/ml in 20 mM HEPES (pH 7) and adding 10 μl/well. The resulting Epic plates were incubated overnight at 4° C. and subsequently blocked with 150 mM borate buffer (pH 9.2) supplemented with 200 mM ethanolamine (Sigma) for 15 minutes, and washed three times with assay buffer (50 mM HEPES (pH7.4, 150 mM NaCl, 0.01% Tween20, 2% DMSO). Assay buffer (15 μL/well) was added and after 2 hours of incubation, a baseline read was taken to determine the amount of BRD4 immobilized. Compound/Inhibitor was added to each well in a tripling dilution series with a starting concentration of 20 μM and each compound concentration was dosed in quadruplicate. Binding of compound/inhibitor to BRD4 was allowed to reach equilibrium (about 1 hr) before a second read was taken. Compound/inhibitor binding was determined by calculating difference between the baseline (first read) and second read. The resulting binding response was fitted to a single site binding isotherm in order to determine an equilibrium dissociation constant ($K_d$). Values reported in Table 1 were rounded to the nearest whole number.

What is claimed is:

1. A compound of Formula I

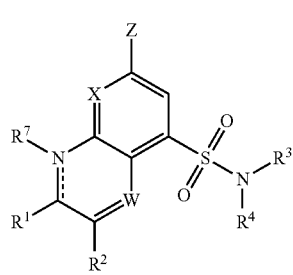

Formula I wherein
R$^1$ is selected from the group consisting of hydrogen, halo, C$_{1-4}$ haloalkyl, unsubstituted or substituted C$_{1-4}$ alkyl, unsubstituted or substituted C$_{3-8}$ cycloalkyl, unsubstituted or substituted C$_{3-8}$ heterocycloalkyl, NR$^{1a}$R$^{1b}$, OR$^{1c}$, and oxo;
  wherein each R$^{1a}$ and R$^{1b}$ is independently selected from the group consisting of hydrogen, unsubstituted or substituted C$_{1-4}$ alkyl, unsubstituted or substituted C$_{3-8}$ cycloalkyl, and unsubstituted or substituted C$_{3-8}$ heterocycloalkyl;
  or R$^{1a}$ and R$^{1b}$ and the nitrogen atom to which they are attached join to form unsubstituted or substituted C$_{3-12}$ heterocycloalkyl, wherein the unsubstituted or substituted C$_{3-12}$ heterocycloalkyl has 1 to 3 heteroatoms selected from the group consisting of O, N, and S;
  wherein R$^{1c}$ is unsubstituted or substituted C$_{1-4}$ alkyl;
R$^2$ is selected from the group consisting of hydrogen, halo, C$_{1-4}$ haloalkyl, cyano, NR$^{2a}$R$^{2b}$, carboxyl, C(O)NR$^{2a}$R$^{2b}$, OR$^{2c}$, unsubstituted or substituted C$_{1-6}$ alkyl, unsubstituted or substituted C$_{3-12}$ cycloalkyl, unsubstituted or substituted C$_{3-12}$ heterocycloalkyl, unsubstituted or substituted C$_{3-12}$ aryl, and unsubstituted or substituted C$_{3-12}$ heteroaryl;
  wherein each R$^{2a}$, R$^{2b}$ and R$^{2c}$ is independently selected from the group consisting of hydrogen, C$_{1-4}$ haloalkyl, unsubstituted or substituted C$_{1-6}$ alkyl, unsubstituted or substituted C$_{3-12}$ cycloalkyl, and unsubstituted or substituted C$_{3-12}$ heterocycloalkyl;
  or R$^{2a}$ and R$^{2b}$ and the nitrogen atom to which they are attached join to form unsubstituted or substituted C$_{3-12}$ heterocycloalkyl or unsubstituted or substituted C$_{3-12}$ heteroaryl; wherein the unsubstituted or substituted C$_{3-12}$ heterocycloalkyl or the unsubstituted or substituted C$_{3-12}$ heteroaryl has 1 to 3 heteroatoms selected from the group consisting of O, N, and S;
W is N or CR$^w$;
  wherein R$^w$ is independently selected from the group consisting of hydrogen, C$_{1-4}$ haloalkyl, unsubstituted or substituted C$_{1-4}$ alkyl, and unsubstituted or substituted C$_{1-4}$ alkoxy;
X is N or CR$^x$;
  wherein Rx is independently selected from the group consisting of hydrogen, halogen, C$_{1-4}$ haloalkyl, unsubstituted or substituted C$_{1-4}$ alkyl, and unsubstituted or substituted C$_{1-4}$ alkoxy;
R$^3$ is selected from the group consisting of hydrogen, and unsubstituted or substituted C$_{1-4}$ alkyl;
R$^4$ is selected from the group consisting of hydrogen, C$_{1-8}$ haloalkyl, unsubstituted or substituted C$_{1-8}$ alkyl, unsubstituted or substituted C$_{3-8}$ cycloalkyl, unsubstituted or substituted C$_{3-12}$ heterocycloalkyl, and unsubstituted or substituted C$_{3-12}$ heteroaryl;
  or R$^3$ and R$^4$ and the nitrogen atom to which they are attached join to form unsubstituted or substituted C$_{3-12}$ heterocycloalkyl or unsubstituted or substituted C$_{3-12}$ heteroaryl;
    wherein the unsubstituted or substituted C$_{3-12}$ heterocycloalkyl or the unsubstituted or substituted C$_{3-12}$ heteroaryl has 1 to 3 heteroatoms selected from the group consisting of O, N, and S;
R$^7$ is hydrogen or absent; and
Z is selected from the group consisting of unsubstituted or substituted isoxazolyl, and unsubstituted or substituted pyrazolyl,
or a pharmaceutically acceptable salt thereof.

2. The compound of claim 1, or a pharmaceutically acceptable salt thereof, wherein R$^1$ is selected from the group consisting of hydrogen, oxo, CHF$_2$, chloro, methoxy, unsubstituted amino,

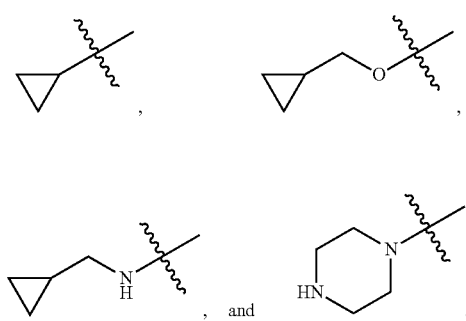

3. The compound of claim 2, or a pharmaceutically acceptable salt thereof, wherein $R^1$ is hydrogen or oxo.

4. The compound of claim 1, or a pharmaceutically acceptable salt thereof, wherein $R^2$ is selected from the group consisting of hydrogen, bromo, cyano, unsubstituted amino,

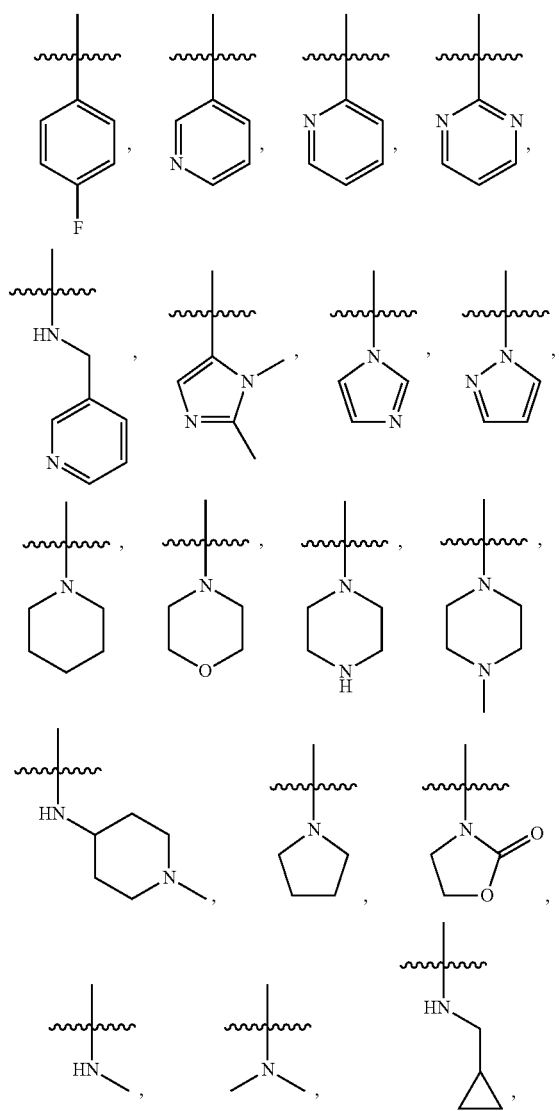

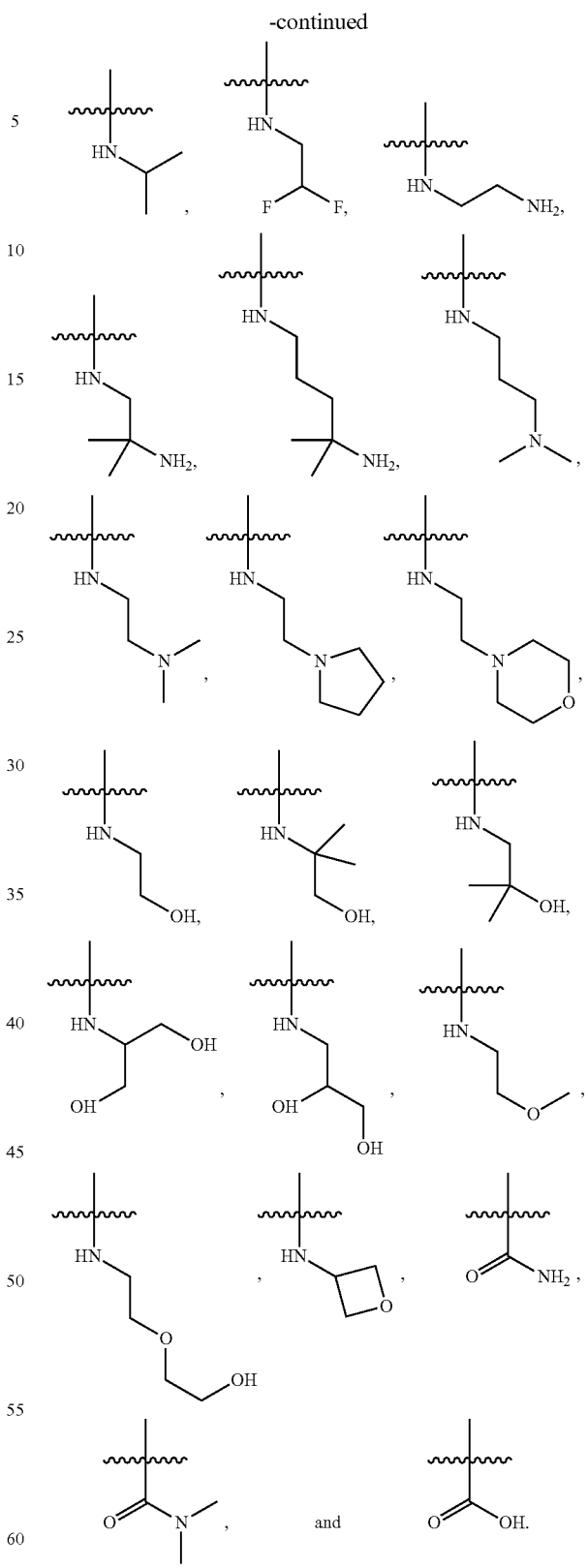

5. The compound of claim 1, or a pharmaceutically acceptable salt thereof, wherein $R^2$ is hydrogen.

6. The compound of claim 1, or a pharmaceutically acceptable salt thereof, wherein $R^3$ is hydrogen or methyl.

7. The compound of claim 1, or a pharmaceutically acceptable salt thereof, wherein
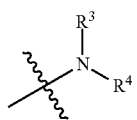
is selected from the group consisting of:
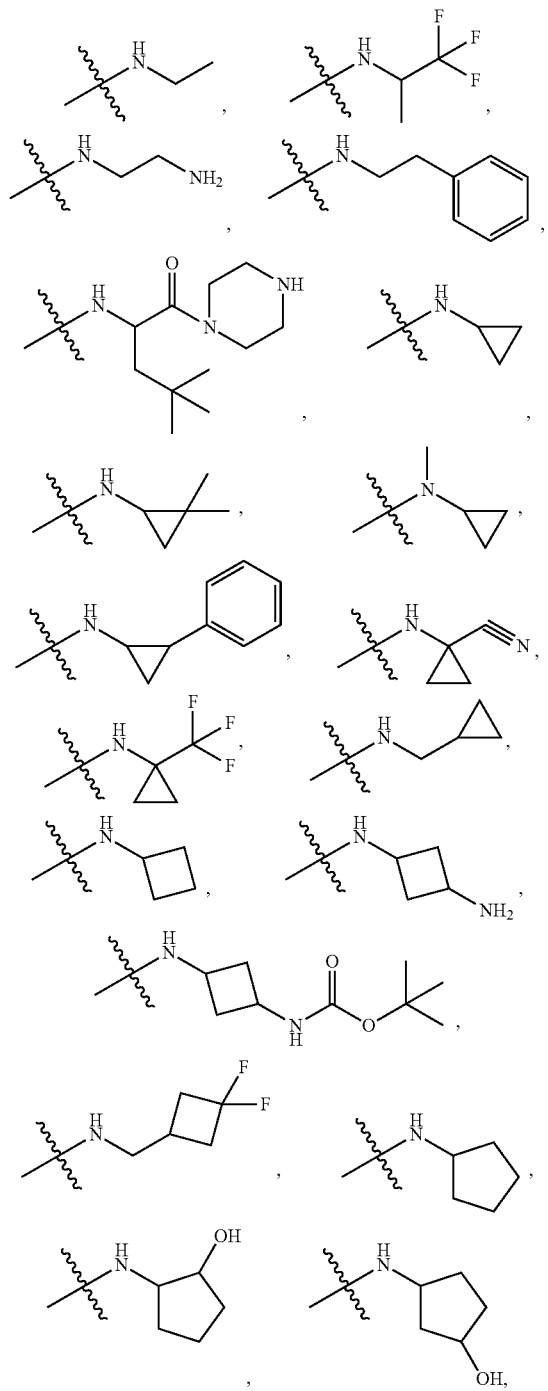
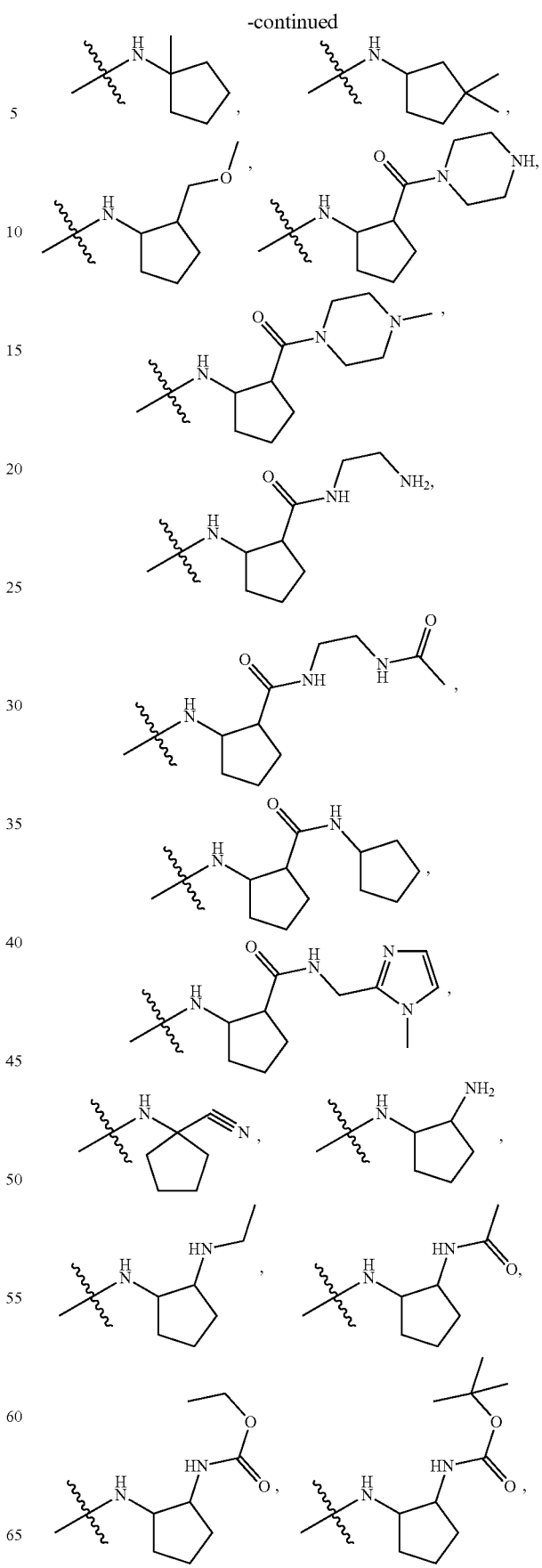

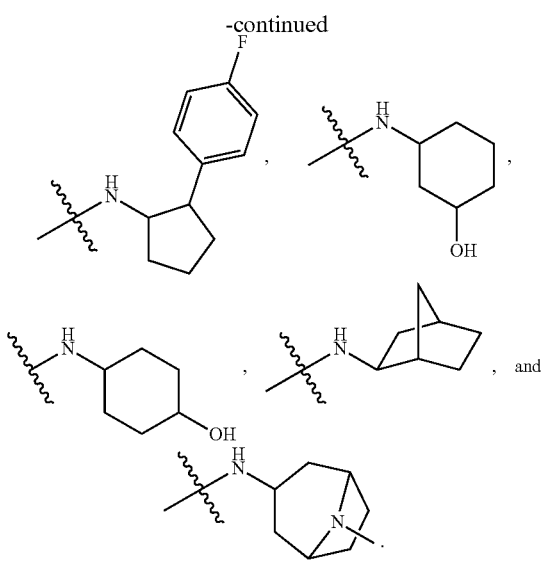

8. The compound of claim 1, or a pharmaceutically acceptable salt thereof, wherein $R^3$ and $R^4$ and the nitrogen atom to which they are attached join to form $C_{3-12}$ heterocycloalkyl or $C_{3-12}$ heteroaryl;

wherein the $C_{3-12}$ heterocycloalkyl or the $C_{3-12}$ heteroaryl has 1 to 3 heteroatoms independently selected from O and N; and wherein the $C_{3-12}$ heterocycloalkyl or the $C_{3-12}$ heteroaryl is unsubstituted, or substituted with 1 to 3 substituents independently selected from halo, unsubstituted $C_{1-4}$ alkyl, and oxo.

9. The compound of claim 1, wherein the compound is a compound of Formula IA

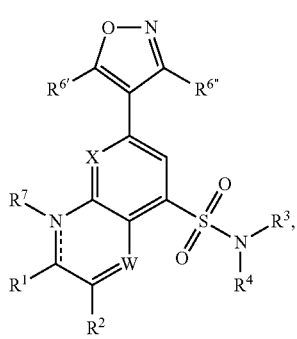

Formula IA wherein $R^1$, $R^2$, W, X, $R^3$, $R^4$, and $R^7$ are as defined in Formula I; and each $R^{6'}$ and $R^{6''}$ is independently selected from the group consisting of unsubstituted $C_{1-4}$ alkyl, $CH_2OR^{6a}$, and $CH_2NR^{6b}R^{6c}$;

wherein each $R^{6a}$, $R^{6b}$, and $R^{6c}$ is independently selected from the group consisting of hydrogen, $C_{1-4}$ haloalkyl, unsubstituted $C_{1-4}$ alkyl, and acetyl, or a pharmaceutically acceptable salt thereof.

10. The compound of claim 9, or a pharmaceutically acceptable salt thereof, wherein each $R^{6'}$ and $R^{6''}$ is methyl.

11. The compound of claim 1, wherein the compound is a compound of Formula IC:

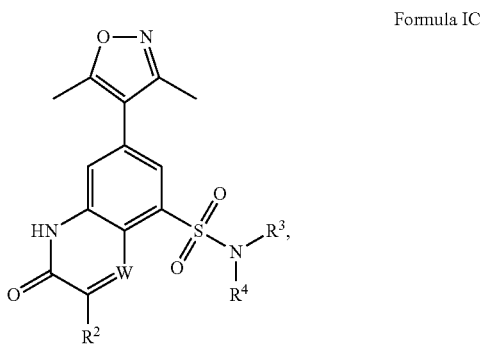

Formula IC wherein:
$R^2$ and W are as defined in Formula I;
$R^3$ is hydrogen; and
$R^4$ is selected from the group consisting of unsubstituted or substituted $C_{1-4}$ alkyl, $C_{1-8}$ haloalkyl, and unsubstituted or substituted $C_{3-8}$ cycloalkyl
or a pharmaceutically acceptable salt thereof.

12. The compound of claim 11, or a pharmaceutically acceptable salt thereof, wherein W is $CR^w$, wherein $R^w$ is hydrogen.

13. The compound of claim 1, or a pharmaceutically acceptable salt thereof, wherein the compound is selected from the group consisting of:
N-cyclopentyl-7-(3,5-dimethylisoxazol-4-yl)quinoline-5-sulfonamide;
N-cyclopentyl-2-(difluoromethyl)-7-(3,5-dimethylisoxazol-4-yl)quinoline-5-sulfonamide;
2-chloro-N-cyclopentyl-7-(3,5-dimethylisoxazol-4-yl)quinoline-5-sulfonamide;
N-cyclopentyl-2-cyclopropyl-7-(3,5-dimethylisoxazol-4-yl)quinoline-5-sulfonamide;
N-cyclopentyl-2-((cyclopropylmethyl)amino)-7-(3,5-dimethylisoxazol-4-yl)quinoline-5-sulfonamide;
N-cyclopentyl-2-(cyclopropylmethoxy)-7-(3,5-dimethylisoxazol-4-yl)quinoline-5-sulfonamide;
N-cyclopentyl-7-(3,5-dimethylisoxazol-4-yl)-2-oxo-1,2-dihydroquinoline-5-sulfonamide;
N-cyclopropyl-7-(3,5-dimethylisoxazol-4-yl)quinoline-5-sulfonamide;
N-cyclopropyl-7-(3,5-dimethylisoxazol-4-yl)-N-methylquinoline-5-sulfonamide;
N-cyclobutyl-7-(3,5-dimethylisoxazol-4-yl)quinoline-5-sulfonamide;
N-((3,3-difluorocyclobutyl)methyl)-7-(3,5-dimethylisoxazol-4-yl)quinoline-5-sulfonamide;
7-(3,5-dimethylisoxazol-4-yl)-N-((1R,2S)-2-phenylcyclopropyl)quinoline-5-sulfonamide;
7-(3,5-dimethylisoxazol-4-yl)-N-((1R,2R)-2-(4-fluorophenyl)cyclopentyl)quinoline-5-sulfonamide;
N-(cyclopropylmethyl)-7-(3,5-dimethylisoxazol-4-yl)quinoline-5-sulfonamide;
N-cyclopentyl-7-(3,5-dimethylisoxazol-4-yl)-2-methoxyquinoline-5-sulfonamide;
2-amino-N-cyclopentyl-7-(3,5-dimethylisoxazol-4-yl)quinoline-5-sulfonamide;
8-chloro-N-cyclopentyl-7-(3,5-dimethylisoxazol-4-yl)quinoline-5-sulfonamide;

7-(3,5-dimethylisoxazol-4-yl)-N-((1S,3R)-3-hydroxycyclopentyl)quinoline-5-sulfonamide;

7-(3,5-dimethylisoxazol-4-yl)-N-((1R,3S)-3-hydroxycyclohexyl)quinoline-5-sulfonamide;

7-(3,5-dimethylisoxazol-4-yl)-N-((1r,4r)-4-hydroxycyclohexyl)quinoline-5-sulfonamide;

3-bromo-N-cyclopentyl-7-(3,5-dimethylisoxazol-4-yl)-2-oxo-1,2-dihydroquinoline-5-sulfonamide;

7-(3,5-dimethylisoxazol-4-yl)-N-((1R,2S)-2-hydroxycyclopentyl)quinoline-5-sulfonamide;

7-(3,5-dimethylisoxazol-4-yl)-N-(1-methylcyclopentyl)quinoline-5-sulfonamide;

tert-butyl(1s,3s)-3-(7-(3,5-dimethylisoxazol-4-yl)quinoline-5-sulfonamido)cyclobutylcarbamate 7-(3,5-dimethylisoxazol-4-yl)-N-((1R,2R)-2-hydroxycyclopentyl)quinoline-5-sulfonamide;

7-(3,5-dimethylisoxazol-4-yl)-N-((1S,2R)-2-hydroxycyclopentyl)quinoline-5-sulfonamide;

N-cyclopentyl-7-(3,5-dimethylisoxazol-4-yl)-3-(4-fluorophenyl)-2-oxo-1,2-dihydroquinoline-5-sulfonamide;

N-cyclopentyl-7-(3,5-dimethylisoxazol-4-yl)-2-oxo-3-(pyridin-3-yl)-1,2-dihydroquinoline-5-sulfonamide;

N-cyclopentyl-3-(1,2-dimethyl-1H-imidazol-5-yl)-7-(3,5-dimethylisoxazol-4-yl)-2-oxo-1,2-dihydroquinoline-5-sulfonamide;

3-cyano-N-cyclopentyl-7-(3,5-dimethylisoxazol-4-yl)-2-oxo-1,2-dihydroquinoline-5-sulfonamide;

N-cyclopentyl-7-(3,5-dimethylisoxazol-4-yl)-3-(1H-imidazol-1-yl)-2-oxo-1,2-dihydroquinoline-5-sulfonamide;

N-cyclopentyl-7-(3,5-dimethylisoxazol-4-yl)-2-oxo-3-(1H-pyrazol-1-yl)-1,2-dihydroquinoline-5-sulfonamide;

N-((1S,3S)-3-aminocyclobutyl)-7-(3,5-dimethylisoxazol-4-yl)quinoline-5-sulfonamide;

(1R,2R)—N-cyclopentyl-2-(7-(3,5-dimethylisoxazol-4-yl)quinoline-5-sulfonamido)cyclopentanecarboxamide;

N-cyclopentyl-7-(3,5-dimethylisoxazol-4-yl)-2-oxo-3-(pyridin-2-yl)-1,2-dihydroquinoline-5-sulfonamide;

N-cyclopentyl-7-(3,5-dimethylisoxazol-4-yl)-2-oxo-3-(pyrimidin-2-yl)-1,2-dihydroquinoline-5-sulfonamide;

N-((1S,2S,4R)-bicyclo[2.2.1]heptan-2-yl)-7-(3,5-dimethylisoxazol-4-yl)quinoline-5-sulfonamide;

N-(3,3-dimethylcyclopentyl)-7-(3,5-dimethylisoxazol-4-yl)quinoline-5-sulfonamide;

7-(3,5-dimethylisoxazol-4-yl)-N-(8-methyl-8-azabicyclo[3.2.1]octan-3-yl)quinoline-5-sulfonamide;

3-amino-N-cyclopentyl-7-(3,5-dimethylisoxazol-4-yl)-2-oxo-1,2-dihydroquinoline-5-sulfonamide;

(1R,2R)-2-(7-(3,5-dimethylisoxazol-4-yl)quinoline-5-sulfonamido)-N-((1-methyl-1H-imidazol-2-yl)methyl)cyclopentanecarboxamide;

(1S,2R)-2-(7-(3,5-dimethylisoxazol-4-yl)quinoline-5-sulfonamido)-N-((1-methyl-1H-imidazol-2-yl)methyl)cyclopentanecarboxamide;

N-cyclopentyl-7-(3,5-dimethylisoxazol-4-yl)-2-(piperazin-1-yl)quinoline-5-sulfonamide;

tert-butyl((1R,2R)-2-(7-(3,5-dimethylisoxazol-4-yl)quinoline-5-sulfonamido)cyclopentyl)carbamate;

N-((1R,2R)-2-aminocyclopentyl)-7-(3,5-dimethylisoxazol-4-yl)quinoline-5-sulfonamide;

7-(3,5-dimethylisoxazol-4-yl)-N-((1R,2R)-2-(piperazine-1-carbonyl)cyclopentyl)quinoline-5-sulfonamide;

7-(3,5-dimethylisoxazol-4-yl)-2-oxo-N-phenethyl-1,2-dihydroquinoline-5-sulfonamide;

N-(1-cyanocyclopropyl)-7-(3,5-dimethylisoxazol-4-yl)quinoline-5-sulfonamide;

7-(3,5-dimethylisoxazol-4-yl)-N-((1R,2S)-2-(piperazine-1-carbonyl)cyclopentyl)quinoline-5-sulfonamide;

N-((1S,2R)-2-(7-(3,5-dimethylisoxazol-4-yl)quinoline-5-sulfonamido)cyclopentyl)acetamide;

N-(1-cyanocyclopentyl)-7-(3,5-dimethylisoxazol-4-yl)quinoline-5-sulfonamide;

7-(3,5-dimethylisoxazol-4-yl)-N-((1R,2S)-2-(ethylamino)cyclopentyl)quinoline-5-sulfonamide;

ethyl((1S,2R)-2-(7-(3,5-dimethylisoxazol-4-yl)quinoline-5-sulfonamido)cyclopentyl)carbamate;

N-cyclopentyl-7-(3,5-dimethylisoxazol-4-yl)-3-morpholino-2-oxo-1,2-dihydroquinoline-5-sulfonamide;

N-cyclopentyl-7-(3,5-dimethylisoxazol-4-yl)-2-oxo-3-(piperazin-1-yl)-1,2-dihydroquinoline-5-sulfonamide;

N-cyclopentyl-7-(3,5-dimethylisoxazol-4-yl)-3-((2-hydroxyethyl)amino)-2-oxo-1,2-dihydroquinoline-5-sulfonamide;

N-cyclopentyl-7-(3,5-dimethylisoxazol-4-yl)-3-((2-methoxyethyl)amino)-2-oxo-1,2-dihydroquinoline-5-sulfonamide;

N-cyclopentyl-7-(3,5-dimethylisoxazol-4-yl)-2-oxo-3-(pyrrolidin-1-yl)-1,2-dihydroquinoline-5-sulfonamide;

N-cyclopentyl-7-(3,5-dimethylisoxazol-4-yl)-2-oxo-3-(piperidin-1-yl)-1,2-dihydroquinoline-5-sulfonamide;

N-cyclopentyl-3-(dimethylamino)-7-(3,5-dimethylisoxazol-4-yl)-2-oxo-1,2-dihydroquinoline-5-sulfonamide;

N-cyclopentyl-7-(3,5-dimethylisoxazol-4-yl)-3-(methylamino)-2-oxo-1,2-dihydroquinoline-5-sulfonamide;

7-(3,5-dimethylisoxazol-4-yl)-N-((1R,2S)-2-(methoxymethyl)cyclopentyl)quinoline-5-sulfonamide;

N-cyclopentyl-7-(3,5-dimethylisoxazol-4-yl)-2-oxo-3-(2-oxooxazolidin-3-yl)-1,2-dihydroquinoline-5-sulfonamide;

N-cyclopentyl-7-(3,5-dimethylisoxazol-4-yl)-3-(4-methylpiperazin-1-yl)-2-oxo-1,2-dihydroquinoline-5-sulfonamide;

N-cyclopentyl-7-(3,5-dimethylisoxazol-4-yl)-3-((1-methylpiperidin-4-yl)amino)-2-oxo-1,2-dihydroquinoline-5-sulfonamide;

N-cyclopentyl-7-(3,5-dimethylisoxazol-4-yl)-2-oxo-3-((pyridin-3-ylmethyl)amino)-1,2-dihydroquinoline-5-sulfonamide;

N-cyclopropyl-7-(3,5-dimethylisoxazol-4-yl)-2-oxo-1,2-dihydroquinoline-5-sulfonamide;

5-(N-cyclopentylsulfamoyl)-7-(3,5-dimethylisoxazol-4-yl)-2-oxo-1,2-dihydroquinoline-3-carboxamide;

5-(N-cyclopentylsulfamoyl)-7-(3,5-dimethylisoxazol-4-yl)-2-oxo-1,2-dihydroquinoline-3-carboxylic acid;

7-(3,5-dimethylisoxazol-4-yl)-N-((1R,2R)-2-(4-methylpiperazine-1-carbonyl)cyclopentyl)quinoline-5-sulfonamide;

(1R,2R)—N-(2-aminoethyl)-2-(7-(3,5-dimethylisoxazol-4-yl)quinoline-5-sulfonamido)cyclopentanecarboxamide;

(1R,2R)—N-(2-acetamidoethyl)-2-(7-(3,5-dimethylisoxazol-4-yl)quinoline-5-sulfonamido)cyclopentanecarboxamide;

N-(2-aminoethyl)-7-(3,5-dimethylisoxazol-4-yl)quinoline-5-sulfonamide;

5-(N-cyclopentylsulfamoyl)-7-(3,5-dimethylisoxazol-4-yl)-N,N-dimethyl-2-oxo-1,2-dihydroquinoline-3-carboxamide;

N-cyclopentyl-3-((cyclopropylmethyl)amino)-7-(3,5-dimethylisoxazol-4-yl)-2-oxo-1,2-dihydroquinoline-5-sulfonamide;

N-cyclopentyl-7-(3,5-dimethylisoxazol-4-yl)-3-(isopropylamino)-2-oxo-1,2-dihydroquinoline-5-sulfonamide;
3-((2-aminoethyl)amino)-N-cyclopentyl-7-(3,5-dimethylisoxazol-4-yl)-2-oxo-1,2-dihydroquinoline-5-sulfonamide;
N-cyclopentyl-3-((2,2-difluoroethyl)amino)-7-(3,5-dimethylisoxazol-4-yl)-2-oxo-1,2-dihydroquinoline-5-sulfonamide;
N-cyclopropyl-7-(3,5-dimethylisoxazol-4-yl)-2-(piperazin-1-yl)quinoline-5-sulfonamide;
(S)—N-(4,4-dimethyl-1-oxo-1-(piperazin-1-yl)pentan-2-yl)-7-(3,5-dimethylisoxazol-4-yl)quinoline-5-sulfonamide;
7-(3,5-dimethylisoxazol-4-yl)-N-((1R,2R)-2-hydroxycyclopentyl)-2-oxo-1,2-dihydroquinoline-5-sulfonamide;
N-(2,2-dimethylcyclopropyl)-7-(3,5-dimethylisoxazol-4-yl)quinoline-5-sulfonamide;
7-(3,5-dimethylisoxazol-4-yl)-N-(1-(trifluoromethyl)cyclopropyl)quinoline-5-sulfonamide;
7-(3,5-dimethylisoxazol-4-yl)-N-((1R,2R)-2-hydroxycyclopentyl)-3-((2-methoxyethyl)amino)-2-oxo-1,2-dihydroquinoline-5-sulfonamide;
N-cyclopentyl-7-(3,5-dimethylisoxazol-4-yl)quinoxaline-5-sulfonamide;
N-cyclopentyl-7-(3,5-dimethylisoxazol-4-yl)-2-oxo-1,2-dihydroquinoxaline-5-sulfonamide;
N-cyclopentyl-3-((2-(dimethylamino)ethyl)amino)-7-(3,5-dimethylisoxazol-4-yl)-2-oxo-1,2-dihydroquinoline-5-sulfonamide;
N-cyclopentyl-7-(3,5-dimethylisoxazol-4-yl)-2-oxo-3-((2-(pyrrolidin-1-yl)ethyl)amino)-1,2-dihydroquinoline-5-sulfonamide;
N-cyclopentyl-7-(3,5-dimethylisoxazol-4-yl)-3-((2-morpholinoethyl)amino)-2-oxo-1,2-dihydroquinoline-5-sulfonamide;
N-cyclopentyl-7-(3,5-dimethylisoxazol-4-yl)-3-(2-(2-hydroxyethoxy)ethyl)amino)-2-oxo-1,2-dihydroquinoline-5-sulfonamide;
N-cyclopentyl-3-((1,3-dihydroxypropan-2-yl)amino)-7-(3,5-dimethylisoxazol-4-yl)-2-oxo-1,2-dihydroquinoline-5-sulfonamide;
N-cyclopentyl-3-((2,3-dihydroxypropyl)amino)-7-(3,5-dimethylisoxazol-4-yl)-2-oxo-1,2-dihydroquinoline-5-sulfonamide;
3-((3-aminopropyl)amino)-N-cyclopentyl-7-(3,5-dimethylisoxazol-4-yl)-2-oxo-1,2-dihydroquinoline-5-sulfonamide;
N-cyclopentyl-3-((3-(dimethylamino)propyl)amino)-7-(3,5-dimethylisoxazol-4-yl)-2-oxo-1,2-dihydroquinoline-5-sulfonamide;
N-cyclopentyl-7-(3,5-dimethylisoxazol-4-yl)-3-(oxetan-3-ylamino)-2-oxo-1,2-dihydroquinoline-5-sulfonamide;
N-cyclopentyl-7-(3,5-dimethylisoxazol-4-yl)-3-(1-hydroxy-2-methylpropan-2-yl)amino)-2-oxo-1,2-dihydroquinoline-5-sulfonamide;
N-cyclopentyl-7-(3,5-dimethylisoxazol-4-yl)-3-((2-hydroxy-2-methylpropyl)amino)-2-oxo-1,2-dihydroquinoline-5-sulfonamide;
3-((2-amino-2-methylpropyl)amino)-N-cyclopentyl-7-(3,5-dimethylisoxazol-4-yl)-2-oxo-1,2-dihydroquinoline-5-sulfonamide; and
(R)-7-(3,5-dimethylisoxazol-4-yl)-N-(1,1,1-trifluoropropan-2-yl)quinoline-5-sulfonamide.

14. A pharmaceutical composition comprising a compound of claim 1, or a pharmaceutically acceptable salt thereof; and at least one pharmaceutically acceptable carrier.

15. A method of treating a subject having a disease or condition responsive to the inhibition of a bromodomain, comprising administering a therapeutically effective amount of a compound of claim 1, or a pharmaceutically acceptable salt thereof, wherein the disease or condition is a solid tumor or a lymphoma.

16. The method of claim 15, wherein the bromodomain is bromodomain-containing protein 4 (BRD4).

17. The method of claim 15, wherein the subject is a human.

18. The method of claim 15, wherein the compound is administered orally.

* * * * *